(12) United States Patent
Serhan et al.

(10) Patent No.: US 8,722,654 B2
(45) Date of Patent: May 13, 2014

(54) LIPOXIN ANALOGS AS NOVEL INHIBITORS OF ANGIOGENESIS

(75) Inventors: Charles N. Serhan, Needham, MA (US); Reza Dana, Cambridge, MA (US); Yiping Jin, Malden, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 115 days.

(21) Appl. No.: 13/106,450

(22) Filed: May 12, 2011

(65) Prior Publication Data

US 2014/0094519 A1    Apr. 3, 2014

Related U.S. Application Data

(60) Continuation-in-part of application No. 11/837,657, filed on Aug. 13, 2007, which is a continuation of application No. 11/222,458, filed on Sep. 8, 2005, now Pat. No. 8,008,282, which is a division of application No. 10/615,361, filed on Jul. 8, 2003, now abandoned, which is a division of application No. 10/086,609, filed on Mar. 1, 2002, now Pat. No. 6,627,658.

(60) Provisional application No. 60/272,931, filed on Mar. 2, 2001.

(51) Int. Cl.
*A01N 43/00* (2006.01)
*A61K 31/33* (2006.01)

(52) U.S. Cl.
USPC ............................................ 514/183

(58) Field of Classification Search
USPC ............................................ 514/183
See application file for complete search history.

(56) References Cited

U.S. PATENT DOCUMENTS

| | | | |
|---|---|---|---|
| 4,560,514 A | 12/1985 | Samuelsson et al. | |
| 4,576,758 A | 3/1986 | Morris | |
| 4,780,281 A | 10/1988 | Marnett et al. | |
| 5,049,681 A | 9/1991 | Sato | |
| 5,079,261 A | 1/1992 | Serhan et al. | |
| 5,322,699 A | 6/1994 | Wright et al. | |
| 5,441,951 A | 8/1995 | Serhan | |
| 5,648,512 A | 7/1997 | Serhan | |
| 5,650,435 A | 7/1997 | Madara et al. | |
| 5,750,354 A | 5/1998 | Simchowitz et al. | |
| 5,837,283 A | 11/1998 | McDonald | |
| 6,048,897 A | 4/2000 | Serhan | |
| 6,100,296 A | 8/2000 | Madara et al. | |
| 6,177,468 B1 | 1/2001 | Madara et al. | |
| 6,316,648 B1 | 11/2001 | Serhan | |
| 6,329,425 B1 | 12/2001 | Madara et al. | |
| 6,387,953 B1 | 5/2002 | Serhan | |
| 6,627,658 B2 | 9/2003 | Serhan et al. | |
| 6,645,978 B1 * | 11/2003 | Gamache et al. | 514/310 |
| 6,653,493 B2 | 11/2003 | Serhan et al. | |
| 2002/0168361 A1 | 11/2002 | Kelly | |
| 2004/0053998 A1 | 3/2004 | Serhan et al. | |

FOREIGN PATENT DOCUMENTS

| | | |
|---|---|---|
| JP | 62-198677 | 9/1987 |
| JP | 63-88153 | 4/1988 |
| JP | 1-228994 | 9/1989 |
| JP | 3-227922 | 10/1991 |
| WO | WO 94/29262 | 12/1994 |
| WO | WO 95/01179 | 1/1995 |
| WO | WO 98/11049 | 3/1998 |
| WO | WO 00/54767 | 9/2000 |
| WO | WO 00/55109 | 9/2000 |
| WO | WO 01/70664 | 9/2001 |

OTHER PUBLICATIONS

Clish et. al. (P.N.A.S (1999) 96:8247-8252).*
Takano, T. et al., Neutrophil-meidated Changes in Vascular Permeability are Inhibited by Topical Application of Aspirin-triggered 15-epi-lipoxin A4 and Novel Lipoxin B4 Stable Analogues:, J. Clin. Invest., vol. 101, No. 4, 1998, pp. 819-826.
Dahlen, S-E. et al., "Lipoxins and Other Lipoxygenase Products with Relevance to Inflammatory Reactions in the Lung", Annals of the New York Academy of Sciences, Advances in the Understanding and Treatment of Asthma (no date available), pp. 262-273.
Corey, E.J. et al., "On the Synthesis and Structure of Lipoxin B", Tetrahedron Letters, vol. 26, No. 16, 1985, pp. 1919-1922.
P. Krishnan, "The Scientific Study of Herbal Wound Healing Therapies: Current State of Play", Current Anesthesia & Critical Care (2006) 17,21-27.
Ganz T., et al., "Antimicrobial Peptides of Phagocytes and Epithelia", Seminars in Hematology, Oct. 1997, vol. 34, No. 4, pp. 343-354. XP009009059.

(Continued)

*Primary Examiner* — Marcos Sznaidman
(74) *Attorney, Agent, or Firm* — Fulbright & Jaworski LLP; Scott D. Rothenberger

(57) ABSTRACT

The present invention is generally drawn to novel isolated therapeutic agents, termed lipoxins, generated from the interaction between a dietary omega-6 polyunsaturated fatty acid (PUFA) such as arachidonic acid (AA), oxygenases and the analgesic aspirin (ASA). Surprisingly, careful isolation of compounds generated from the combination of components in an appropriate environment provide di- and tri-hydroxy containing derivatives of AA containing compounds having unique structural and physiological properties. The present invention therefore provides for many new useful therapeutic di- and tri-hydroxy derivatives of AA (lipoxins, aspirin-triggered epi-lipoxins) that diminish, prevent, or eliminate NV, hemangiogenesis and/or angiogenic condition(s) of corneal tissue. The present invention also provides methods of use, methods of preparation, and packaged pharmaceuticals for use as medicaments for the compounds disclosed throughout the specification.

2 Claims, 16 Drawing Sheets

(56) References Cited

OTHER PUBLICATIONS

Elsbach P. et al., "Role of the Bactericidal/Permeability-Increasing Protein in Host Defense", Current Opinion in Immunology, Feb. 1998, vol. 10, No. 1, pp. 45-49, XP002238031.

Canny Geraldine et al., "Lipid Mediator-Induced Expression of Bactericidal/Permeability-Increasing Protein (BPI) in Human Mucosal Epithelial", Proceedings of the National Academy of Sciences of the United States of America, Mar. 2002, vol. 99, No. 6, pp. 3902-3907, XP002238032.

Levy Ofer, "Therapeutic Potential of the Bactericidal/Permeability-Increasing Protein", Expert Opinion of Investigational Drugs, Feb. 2002, vol. 11, No. 2, pp. 159-167, XP001147178.

Levy Ofer, "A Neutrophil-Derived Anti-Infective Molecule: Bactericidal/Permeability-Increasing Protein", Antimicrobial Agents and Chemotherapy, United States Nov. 2000, pp. 2925-2931, XP002238033.

Levy Ofer, "Antimicrobial Proteins and Peptides of Blood: Templates for Novel Antimicrobial Agents", Blood, Oct. 15, 2000, vol. 96, No. 8, pp. 2664-2672, XP002238034 European Search Report 5 pgs.

Samuelsson, B., "An Elucidation of Arachidonic Acid Cascade Discovery of Prostaglandins, Thromboxane and Leukotrienes", Drugs, vol. 33, Supp. 1, 1987, pp. 209.

Nash, S. et al., "Effects of Polymorphonuclear Leukocyte Transmigration on the Barrier Function of Cultured Intestinal Epithelial Monolayers", J. Clin. Invest., vol. 80, 1987, pp. 1104-1113.

Popov, G. K., et al., "Effect of Lipoxin B on Colony-Forming Ability of Human Peripheral Blood Mononuclears in a Diffusion Chamber", Chelyabinsk Medical Institute, Department of Pathophysiology and Section of Human Cardiovascular Pathology. Translated from Byulleten' Eksperimenta' noi Biologii i Meditsiny, vol. 107, No. 1, 1989, pp. 80-83.

Nicolaou, K.C., et al., "Identification of a novel 7-cis-11-trans-lipoxin A4 generated by human neutrophils: total synthesis, spasmogenic activities and comparison with other geometric isomers of lipoxins A4 and B4", Biochimica et Biophysica Acts, No. 1003, 1989, pp. 44-53.

Nicolaou, K.C. et al., "Total Synthesis of Novel Geometric Isomers of Lipoxin A4 and Lipoxin B4", Reprinted from The Journal of Organic Chemistry, vol. 54, 1989, pp. 5527-5535.

Nlgam, S., et al., "Lipoxin A4 and Lipoxin B4 Stimulate the Release but Not the Oxgenation of Arachidonic Acid in Human Neutrophils: Dissociation Between Lipid Remodeling and Adhesion", Journal of Cellular Physiology, vol. 143, 1990, pp. 512-523.

Fiore, S., et al., "The Lipoxin Biosynthetic Circuit and Their Actions with Human Neutrophils", Advances in Experimental Medicine and Biology, vol. 314, 1991, pp. 109-132.

Pettitt, T.R., et al. "Synthesis of Lipoxins and Other Lipoxygenase Products by Macrophages from the Rainbow Trout, Oncorhynchus mykiss", The Journal of Biological Chemistry, vol. 266, No. 14, 1991, pp. 8720-8726.

Parkos, C.A., et al., "Neutrophil Migration across a Cultured Intestinal Epithelium", J. Clin. Invest., vol. 88, 1991, pp. 1605-1612.

Lee, T.H., et al. "Inhibition of Leukotriene B4-Induced Neutrophil Migration by Lipoxin A4: Structure-Function Relationships", Biochemical and Biophysical Research Communications, vol. 180, No. 3, 1991, pp. 1416-1421.

Serhan, C., "Lipoxins: Eicosanoids Carrying Intra- and Intercellular Messages", Journal of Bioenergetics and Biomembranes, vol. 23, No. 1, 1991, pp. 105-122.

Brady, H.R., et al., "Leukotrienes stimulate neutrophil adhesion to mesangial cells: modulation with lipoxins", American Journal Physiology, vol. 259, 1990, pp. F809-F815.

Nicolaou, K.C., et al., "Lipoxins and Related Eicosanoids: Biosynthesis, Biological Properties, and Chemical Synthesis", Angew. Chem. Int. Ed. Engl., vol. 30, 1991, pp. 1100-1116.

Badr, K.F., "15-Lipoxygenase products as leukotriene antagonists: Therapeutic potential in glomerulonephritis", Kidney international, vol. 42, Supp. 38, 1991, pp. S101-S108.

Fiore, S., et al., "Lipoxin Recognition Sites", The Journal of Biological Chemistry, vol. 267, No. 23, 1992, pp. 16168-16176.

Parkos, C.A., et al., "Neutrophil Migration Across a Cultured Epithelial Monolayer Elicits a Biphasic Resistance Response Representing Sequential Effects on Transcellular and Paracellular Pathways", The Journal of Cell Biology, vol. 117, No. 4, 1992, pp. 757-764.

Noelle, R.J. "A 39-kDa protein on activated helper T cells binds CD40 and transduces the signal for cognate activation of B cells", Proc. Natl. Acad. Sci. USA, vol. 89, 6991 pp. 6550-6554.

Madara, J.L., et al., "A Simple Approach to Measurement of Electrical Parameters of Cultured Epithelia Monolayers: Use in Assessing Neutrophil-Epithelial Interactions", J. Tiss. Cult. Meth., vol. 14, 1992, pp. 209-216.

Kathoh, T., et al., "Renal hemodynamic actions of lipoxins in rats: a comparative physiological study", American Journal Physiology, vol. 263, 1992, pp. F436-F442.

Folkman, J., et al., "Angiogensis", J. Biol. Chem., 267, 1992, pp. 10931-10934.

Lederman, S. et al., "Identification of a Novel Surface Protein on Activated CD4+ T Cells That Induces Contact-dependent B Cell Differentiation (Help)", J. Exp. Med., vol. 175, 1992, pp. 1091-1101.

Hia, T.A., et al. "Cyclooxygenase Gene Expression in Inflammation and Angiogensis". Annals N.Y. Acad. Sci., vol. 696, 1993, pp. 197-204.

Madara, J.L., et al. "5'-Adenosine Monophosphate is the Neutrophil-dervied Paracrine Factor that Elicits Chloride Secretion from T84 Intestinal Epithelial Cell Monolayers", J. Clin. Invest., vol. 91, 1993, pp. 2320-2325.

Fiore, S. et al., "Induction of Functional Lipoxin A4 Receptors in HL-60 Cells", Blood, vol. 9, No. 12, 1993, pp. 3395-3403.

Mizukami, Y. et al., "ω-Hydroxylation of lipoxin B4 by human neutrophil microsomes: identification of ω-hydroxy metabolite of lipoxin B4 and catalysis by leukotriene B4 ω-hydroxylase (cytochrome P-450LTBω)", Biochimica et Biophysics Acta, No. 1168, 1993, pp. 87-93.

Claria, J. et al., "Aspirin triggers previously undescribed bioactive eicosanoids by Human endothelial cell-leukocyte interactions", Proc. Natl. Acad. Sci. USA 92, No. 21, 1995, pp. 9475-9479.

Marshall, N.J. et al., "A Critical Assessment of the Use of Microculture Tetrazolium Assys to Measure Cell Growth and Function", Growth Regulation, 5, 1995, pp. 69-84.

Folkman, J., "Angiogensis in cancer, vascular, rheumatorid and other disease", Nature Medicine, vol. 1. No. 1,1995, pp. 27-31.

Marcus, A.J., "Aspirin as Prophylaxis Against Colorectal Cancer", New Eng. J. Med., vol. 333, No. 10, 1995, pp. 636-638.

Colville-Nash, P.R., et al, "The Pharmacological Modulation of Angiogensis in Chronic Granulomatous Inflammation", J. Pharmacol., vol. 274, No. 3, 1995, pp. 1463-1472.

Maddox, J.F., et al., "Lipoxin A4 and B4 Are Potent Stimuli for Human Monocyte Migration and Adhesion: Selective Inactivation by Dehydrogenation and Reduction", J. Exp. Med., vol. 183, 1996, pp. 137-146.

Stoltz, R.A. et al., "The role of NF-κB in the angiogenic response to coronary microvessel endothelial cells", Proc. Natl. Acad. Sci. USA, vol. 93, 1996, pp. 2832-2837.

Claria, J. et al., "Aspirin-Triggered Lipoxins (15-epi-LX) Are Generated by the Human Lung Adenocarcinoma Cell Line (A549)-Neutrophil Interactions and Are Potentin Inhibitors of Cell Proliferation", Molecular Medicine, vol. 2, No. 5, 1996, pp. 583-596.

Papayianni, A. et al., "Lipoxin A4 and B4 Inhibit Leukotriene-Stimulated Interactions of Human Neutrophils and Endothelial Cells", J. Immunology, vol. 156, 1996, pp. 2264-2272.

Romano, M. et al, "Activation of Human Monocytes and the Acute Monocytic Leukemia Cell Line (THP-1) by Lipoxins Involves Unique Signaling Pathways for Lipoxin A4 Versus Lipoxin B4", J. Immunology, vol. 157, 1996, pp. 2149-2154.

Serhan, C., "Lipoxins and Novel Aspirin-Triggered 15-epi-Lipoxins (ATL): A Jungle of Cell-Cell Interactions or a Therapeutic Opportunity?", Prostaglandins, vol. 53, No. 2, 1997, pp. 107-137.

(56) References Cited

OTHER PUBLICATIONS

Takano, T. et al., "Aspirin-Triggered 15-epi-Lipoxin A4 (LXA4) and LXA4 Stable Analogs are Potent Inhibitors of Acute Inflammation: Evidence for Anti-inflammatory Receptors", *J. Exp. Med.*, vol. 185, No. 9, 1997, pp. 1693-1704.
Hoper, M.M., et al., "Prostaglandins Induce Vascular Endothelial Growth Factor in a Human Monocytic Cell Line and Rate Lungs via cAMP", *Am. J. Respir. Cell. Mol. Biol.*, vol. 17, 1997, pp. 748-756.
Gronert, K. et al, "Characterization of Human Neutrophil and Endothelial Cell Ligand-Operated Extracellular Acidification Rate by Microphysiometry: Impact of Reoxygenation", *J. Pharmacol. Exp. Therap.*, vol. 285, No. 1, 1998, pp. 252-260.
Maddox, J. F. et al., "Lipoxin B4 regulates human monocyte/neutrophil adherence and motility: design of stable lipoxin B4 analogs with increased biologic activity", *The FASEB Journal*, vol. 12, 1998, pp. 487-494.
Gewirtz, A.T. et al., "Pathogen-induced Chemokine Secretion from Model Intestinal Epithelium is Inhibited by Lipoxin A4 Analogs", *J. Clin. Invest.*, vol. 101, No. 9, 1998, pp. 1860-1869.
Chiang, N. et al., "Aspirin-Triggered 15-epi-Lipoxin A4 (ATL) Generation by Human leukocytes and Murine Peritonitis Exudates: Development of a Specific 15-epi-LXA4, ELISA1", *J. Pharmacol. Exp. Therap.*, vol. 287, No. 2, 1998, pp. 779-790.
Serhan, C., "Lipoxins and Aspirin-Triggered 15-epi-Lipoxins", *Inflammation: Basic Principles and Clinical Correlates*, $3^{rd}$ ed. 1999, pp. 373-385.
Arenberg, D.A. et al, "Angiogensis", *Inflammation: Basic Principles and Clinical Correlates*, $3^{rd}$ ed. 1999, pp. 851-864.
Gupta, K. et al., "VEGF Prevents Apoptosis of Human Microvascular Endothelial Cells via Opposing Effectson MAPK/ERK and SAPK/JNK Signaling", *Experimental Cell Research*, vol. 247, No. 2, 1999, pp. 495-504.
Kelavkar, U.P. et al., "Effects of mutant p53 expression on human 15-lipoxygenase-promoter activity and murine 12/15-lipoxygenase gene expression: Evidence that 15-lipoxygenase is a mutator gene", *Proc. Natl. Acad. Sci. USA*, vol. 96, 1999, pp. 4378-4383.
Eliceiri, B.P. et al., "The role of αv integrins during angiogenesis: insights into potential mechanisms of action and clinical development", *J. Clin. Invest*, vol. 103, No. 9, 1999, pp. 1227-1230.
Hachicha, M. et al., "Lipoxin (LX) A4 and Aspirin-Triggered 15-epi-LXA4 Inhibit Tumor Necrosis Factor 1α-initiated Neutrophil Responses and Trafficking: Regulators of Cytokine-Chemokine Axis", *J. Exp. Med.*, vol. 189. No. 12, 1999, pp. 1923-1929.
Clish, C.B. et al., "Local and systemic delivery of a stable aspirin-triggered lipoxin prevents neutrophil recruitment in vivo", *Proc. Natl. Acad. Sci. USA*, vol. 96, 1999, pp. 8247-8252.
Munger, K.A. et al., "Transfection of rat kidney with human 15-lipoxygenase suppresses inflammation and preserves function in experimental glomerulonephritis", *Proc. Natl. Acad. Sci. USA*, vol. 96, No. 23, 1999, pp. 13375-13380.
Masferrer, J.L., et al, "COX-2 Inhibitors A New Class of Antiangiogenic Agents", *Annals. N.Y. Acad. Sci.*, vol. 889. 1999, pp. 84-86.
Jones, M.K. et al., "Inhibition of angiogenesis by nonsteroidal anti-inflammatory drugs: Insight into mechanisms and Implications for cancer growth and ulcer healing", *Nature Medicine*, vol. 5, No. 12, 1999, pp. 1418-1423.
Serhan, C.N. et al., "Formation of Endogenous "Antiinflammatory" Lipid Mediators by Transcellular Biosynthesis", *Am. J. Respir. Crit. Care Med.*, vol. 161, 2000, pp. S95-S101.
Sodin-Semrl, S. et al., "Lipoxin A4 Inhibits IL-1B-Induced IL-6, IL-8, and Matrix Metalloproteinase-3 Production in Human Synovial Fibroblasts and Enhances Synthesis of Tissue Inhibitors of metalloproteinases", *J. Immunolog.*, vol. 164, No. 5, 2000, pp. 2660-2666.
Sanak, M. et al., "Aspirin-tolerant asthmatics generate more lipoxins than aspirin-intolerant asthmatics", *Eur. Respir. J.*, vol. 16, 2000, pp. 44-49.
Nie, D. et al., "Eicosanoid regulation of angiogenesis: role of endothelial arachidonate 12-lipoxygenase", *Blood*, vol. 95. No. 7, 2000, pp. 2304-2311.
McMahon, B. et al., "Lipoxin A4 Antagonizes the Mitogenic Effects of Leukotriene D4 in Human Renal Mesangial Cells", *J. Biolog. Chem.*, vol. 275. No. 36, 2000, pp. 27566-27575.
Vane, J., "Aspirin and other anti-inflammatory drugs", *Thorax*, vol. 55, Supp. 2, 2000, pp. S3-S9.
Chiang, N. et al., "Lipoxin A4 Receptor", *Cytokine Reference*, Academic Press, London, 2001, pp. 2199-2233.
Gronert, K. et al., "Short Communication Selectivity of Recombinant Human Leukotriene D4, Leukotriene B4, and Lipoxin A4 Receptors with Aspirin-Triggered 15-epi-LXA4 and Regulation of Vascular and Inflammatory Responses", *Am. J. Pathol.*, vol. 159, No. 1, 2001, pp. 3-9.
Stacker, S.A. et al., "VEGF-D promotes the metastatic spread of tumor cells via the lymphatics", *Nature Medicine*, vol. 7, No. 2, 2001, pp. 186-191.
Skobe, M. et al., "Induction of tumor lymphangiogenesis by VEGF-C promotes breast cancer metastasis", *Nature Medicine*, vol. 7, No. 2, 2001, pp. 192-198.
Makinen, T. et al., "Inhibition of lymphangiogenesis with resulting lymphedema in transgenic mice expressing soluble VEGF receptor-3", *Nature Medicine*, vol. 7, No. 2, 2001, pp. 199-205.
Serhan, C.N. et al., "Unorothox routes to prostanoid formation: new twists in cyclooygenase-initiated pathways", *J. Clin. Invest.*, vol. 107, No. 12, 2001, pp. 1481-1489.
Serhan, C. et al., "Design of Lipoxin A4 Stable Analogs that Block Transmigration and Adhesion of Human Neutrophils", *Biochemistry*, vol. 34 No. 44, 1995, pp. 14609-14615.
Maddox, J.F. et al., "Lipoxin A4 Stable Analogs are Potent Mimetics that Stimulate Human Monocytes and THP-1 Cells via a G-protein-linked Lipoxin A4 Receptor", *The Journal of Biological Chemistry*, vol. 272 No. 11, 1997, pp. 6972-6978.
XP008017720, I. Fierro et al., "A Novel Inhibitor of Angiogenesis: Aspirin-Triggered 15-R Lipoxin A4", FASEB Journal, vol. 15, No. 5, 2001, pp. A949.
XP002244851, C.N. Serhan, et al., "Current Inflammation Research Series: Molecular and Cellular Basis of Inflammation", Humana Press Inc., 1999, pp. xii-338p.
Ather et al., Wound Management-Developments in Treatment Options, European Dermatology Review, 2006, 59-60.
Kramer, Effect of Zpovidone-Iodine on Wound Healing: A Review, Jourlan of Vascular Nursing, 1999, 27-17-21.

\* cited by examiner

LIPOXIN ANALOGS AS NOVEL INHIBITORS OF ANGIOGENESIS

CROSS REFERENCE TO RELATED APPLICATION(S)

This application is a Continuation-in-Part of U.S. Utility application Ser. No. 11/837,657, filed Aug. 13, 2007, which is a Continuation of U.S. patent application Ser. No. 11/222,458, filed Sep. 8, 2005, which is a Divisional of U.S. patent application Ser. No. 10/615,361, filed Jul. 8, 2003, which is a Divisional of U.S. patent application Ser. No. 10/086,609, filed Mar. 1, 2002, now U.S. Pat. No. 6,627,658, which claims benefit to U.S. Provisional Application No. 60/272,931, filed Mar. 2, 2001, entitled "A Novel Inhibitor of Angiogenesis: Aspirin-Triggered-15R Lipoxin $A_4$", the contents of which are incorporated herein by reference.

STATEMENT REGARDING FEDERALLY SPONSORED RESEARCH

The work leading to this invention was supported in part by Department of Defense Grant W81XWH-07-2-0038, NIH R01-EY 12963, NIH/NCRR P20 RR20753Planning Grant For Research on Blinding Eye Diseases, NIH GM38675 and P50 DE0169191 and National Institute of Health Grant Nos. GM38765 and P01-DE13499. The U.S. Government therefore may have certain rights in the invention.

FIELD OF THE INVENTION

The present invention relates to previously unknown therapeutic agents derived from novel signaling and biochemical pathways that use arachidonic acid (AA), which are polyunsaturated fatty acids (PUFAs, omega-6) as precursors to the production of bioactive novel endogenous products that control physiologic events in inflammation and resolution in vascular endothelial reactions and neural systems (brain). More specifically, the present invention relates to di- and trihydroxy potent bioactive products termed "Lipoxins", which are derived from polyunsaturated fatty acids. In addition, therapeutic stable analogs of lipoxins that enhance their biologic properties are described that can be used to expedite resolution by inhibiting the proinflammatory amplification of leukocyte entry.

BACKGROUND OF THE INVENTION

The normal cornea has no blood or lymphatic vessels. This feature is essential for corneal transparency and optimal visual performance, and contributes to the immunologic privilege of the cornea.

Neovascularization (NV) is a common complication secondary to various corneal diseases, including infection, degeneration, trauma and stem cell deficiency-induced insults. NV is also strongly associated with graft failure after corneal transplantation. Additionally, corneal NV as a result of viral or chlamydial (trachoma) infection is a leading cause of visual impairment worldwide.

Corneal NV is a complex response to a number of stimuli, and involves a sequence of coordinated cellular and molecular mechanisms. Dilation of the existing limbal vessels followed by adhesion and diapedesis of leukocytes, such as neutrophils and macrophages, and migration and proliferation of vascular endothelial cells (EC), in large part mediated by VEGF, are all important factors in NV pathogenesis (1,2,3).

Limited therapeutics are available to topically treat inflammation in the cornea that are also able to regulate unwanted neovascularization of the corneal tissue. Current anti-inflammatories for topical treatments in the eye, i.e., applied directly to the cornea, include steroids, which are well appreciated by the clinical community to have long-term deleterious side effects. Such side effects include well-known complications such as cataracts, infection and glaucoma.

Angiogenesis is a fundamental process by which new capillaries are formed from existing blood vessels. This process plays important roles in physiological events such as formation of the corpus luteum, development of the embryo and wound healing, including recovery from both myocardial ischemia and peptic ulcer (1). Unregulated growth of blood vessels can contribute to tissue injury in a large number of diseases such as arthritis, diabetes, and tumor progression (2). Endothelial cells are normally quiescent and are activated during the angiogenic response. Upon stimulation, endothelial cells can degrade their basement membrane and proximal extracellular matrix, migrate directionally, then divide and organize into functional capillaries invested by a new basal lamina (3).

There is a growing body of evidence demonstrating that the angiogenic switch is regulated by the net balance between positive and negative regulators of new capillary growth (2). Persistence of neovascularization requires a pro-angiogenic environment, with the expression of angiogenic factors outweighing that of angiostatic factors. A range of peptides can influence this balance, including mitogenic factors such as vascular endothelial growth factor (VEGF) (3), nonmitogenic factors (selected cytokines, CXC chemokines), and internal peptide fragments of angiostatin and endostatin (3). Certain eicosanoids also have potent biologic actions on vascular endothelial cells. In rabbits, $PGE_2$, $PGR_{2\alpha}$, and prostacylin ($PGI_2$) stimulate angiogenesis where prostaglandin E series, in particular $PGE_1$, is most potent. $PGE_2$ is a potent inducer of VEGF expression in synovial fibroblasts. In addition to its known vasodilator and antiplatelet properties, $PGI_2$ can also induce VEGF gene expression and protein synthesis (4).

It was recently reported that 12-lipoxygenase activity and one of its products, 12(S)-HETE, is required for angiogenic responses (5), and that P450-derived 12R-HETE stimulates angiogenesis via NF-kB (6). The cyclooxygenase-2 (COX-2) gene in endothelial cells is rapidly upregulated by several growth factors as well as inducers of angiogenesis (7). Along these lines, results using three different endothelial cell models show that COX-2 is an essential component of angiogenesis, at least in vitro (8). Nonsteroidal anti-inflammatory drugs such as aspirin (ASA) have been implicated in the prevention of certain cancers such as lung and colon cancer (9, 10) that might be related to ASA's ability to reduce angiogenesis (7).

A need therefore exists, for compositions and methods to prevent angiogenesis that are directed toward the disease process, such that angiogenesis is prevented or inhibited physiologically. A need also exists for compositions and methods that induce angiogenesis in tissue that is lacking the requisite or essential physiological requirements for sustainability. Further, A need exists for an improved understanding of neovascularization as well as the isolation and preparation of bioactive agents that can serve to eliminate or diminish NV pathogenesis, especially associated with the cornea.

BRIEF SUMMARY OF THE INVENTION

The present invention, in one embodiment, is drawn to isolated therapeutic agents generated from the interaction between a dietary omega-6 PUFA, such as arachidonic acid, an oxygenase, such as cyclooxygenase-II (COX-2), and an analgesic, such as aspirin (ASA). Surprisingly, careful and challenging isolation of previously unknown and unappreciated compounds are generated from exudates by the combination of components in an appropriate environment to provide di- and tri-hydroxy AA derivatives having unique structural and physiological properties. The present invention therefore provides for many new useful therapeutic di- and tri-hydroxy derivatives of AA, lipoxins, that diminish, prevent, or eliminate NV, hemangiogenesis or angiogenic conditions associated with corneal tissue.

Lipoxins, such as ATLa (15-epi-16-(p-fluorophenoxy)-$LXA_4$ methyl ester) are novel anti-inflammatory lipid mediators derived from omega-6 fatty acid arachidonic acid. At the local site of inflammation, aspirin treatment enhances AA conversion to 15R-oxygenated products including ATLa that carry potent anti-inflammatory signals. Surprisingly, lipoxins (such as those identified throughout the specification) such as ATLa protected against, reduced or inhibited the development of NV, hemangiogenesis and/or angiogenesis, in a well appreciated experimental mouse model.

The beneficial effect was reflected by decreased generation or elimination of neovascularization. Thus, the novel endogenous lipid mediators termed "lipoxins", such as ATLa counterregulate leukocyte-mediated tissue injury and pro-inflammatory gene expression. These findings show a novel endogenous mechanism that may underlie the beneficial actions of omega-6 AA and provides new approaches for the treatment of undesirable NV, hemangiogenesis or angiogenic conditions in the cornea.

In one aspect, lipoxins, epi-lipoxins, lipoxin analogs and epi-lipoxin analogs useful as therapeutic agents for treatment of the maladies described throughout this specification have the formulae encompassed by U.S. Pat. Nos. 4,560,514, 5,441,951, 5,648,512, 5,650,435, 6,048,897, 6,627,658 and 6,670,396, the contents of which are incorporated herein by reference in their entirety.

Another embodiment of the present invention is directed to pharmaceutical compositions of the novel compounds described throughout the specification useful to treat undesirable NV, hemangiogenesis or angiogenic conditions in cornea tissue.

The present invention also provides methods to treat various disease states and conditions described throughout the specification, including for example, neovascularization.

The present invention further provides various methods to prepare the novel compounds described throughout the specification.

The present invention also provides packaged pharmaceuticals that contain the novel di- and tri-hydroxy AA (lipoxin) derivatives described throughout the specification for use in treatment with various conditions associated with NV, hemangiogenesis or angiogenic conditions associated with corneal tissue.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the drawings and detailed description are to be regarded as illustrative in nature and not restrictive.

BRIEF DESCRIPTION OF THE DRAWINGS

The invention will be more fully understood from the following detailed description taken in conjunction with the accompanying drawings, in which:

FIG. 4B, Cedar wood oil histology of air pouch. Carmine dye vascular casts were made in day-6 air pouch from mice treated locally with vehicle, ATL-1 (10 µg), VEGF (1 µg) or VEGF plus ATL-1. Tissue was fixed in ethanol and cleared in cedarwood oil.

FIG. 10A, VEGF ligand species (VEGF-A, VEGF-C, VEGF-D) and FIG. 10B VEGFRs (VEGFR2 and VEGFR3) were tested by real-time PCR and normalized to GAPDH mRNA. Values are expressed as fold change over the normal control cornea. Results represent the mean (±SEM) of three samples per group (each sample consisted of 2 pooled corneas), and the data are representative of two independent experiments (* $P<0.05$,  $P<0.001$, * $P<0.0005$, vs vehicle-treated group, t-test).

FIG. 11A, In a masked fashion, corneal NV was scored biomicroscopically with a slit-lamp using a grid system. Values are expressed as the mean (±SEM) of 6 corneas. FIG. 11B, Whole corneal tissues were harvested on day 14 and double-stained with anti-CD31 (green) and anti-LYVE-1 (red) for epifluorescence microscopy (20× magnification). FIG. 11C, The density of blood vessels ($CD31^{high}$/LYVE-1$^-$) or lymphatic vessels ($CD31^{low}$LYVE-1$^{high}$) covering the cornea was analyzed. Values are expressed as the mean (±SEM) of 6 corneas of per treatment group (** $P<0.001$ vs vehicle-treated group, t-test), and the data are representative of two independent experiments.

DETAILED DESCRIPTION

Figure 1:
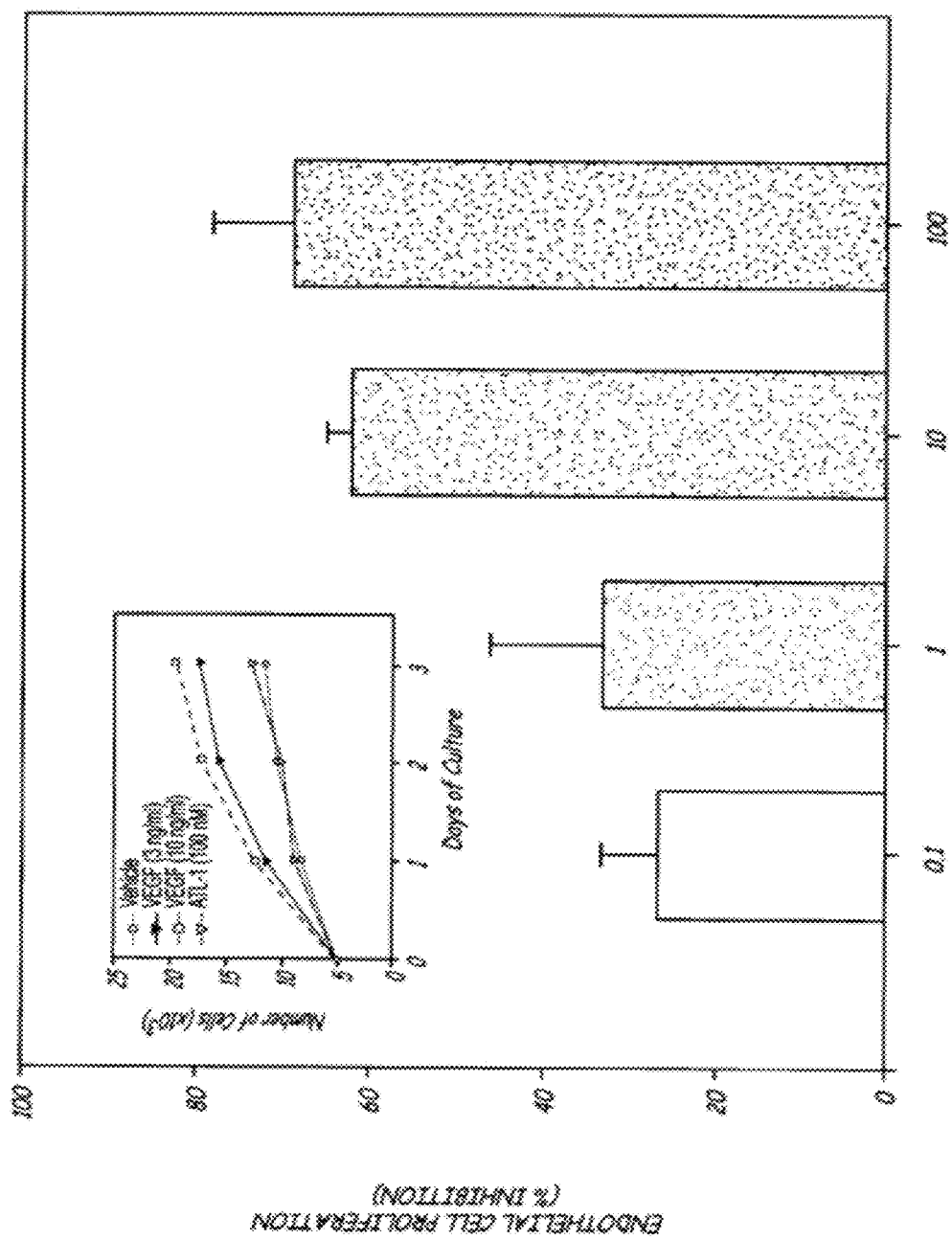
FIG. 1 demonstrates that ATL-1 inhibits VEGF-stimulated HUVEC proliferation. HUVEC ($5\times10^3$) were plated in 96-well culture plates and cell proliferation was stimulated with 3 ng/ml VEGF. Three days after treatment, cell numbers were measured using MTT assay. Results are expressed as percent inhibition of proliferation relative to vehicle and represent mean±SE for four independent experiments performed in triplicate. Inset: Representative experiment showing the time course of cell proliferation induced by 3 ng/ml (filled triangle) or 10 ng/ml (filled square) VEGF. Vehicle (open circles) and ATL-1 (100 nM) (open triangle).

The features and other details of the invention will now be more particularly described and pointed out in the claims. It will be understood that the particular embodiments of the invention are shown by way of illustration and not as limitations of the invention. The principle features of this invention can be employed in various embodiments without departing from the scope of the invention.

In the specification and in the claims, the terms "including" and "comprising" are open-ended terms and should be interpreted to mean "including, but not limited to . . . . " These terms encompass the more restrictive terms "consisting essentially of" and "consisting of:

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

Abbreviations used throughout the present application include the following and are included here for convenience.

ALX, the human $LXA_4$ receptor;
AA, arachidonic acid;
ASA, aspirin;
ATL, aspirin-triggered 15-epi-LX, 15 R-LX;
ATLa, 15-epi-16-(para-fluoro)-phenoxy-lipoxin $A_4$ methyl ester;
ATLa, aspirin triggered lipoxin $A_4$;

ATL-1,15-epi-16-(para-fluoro)-phenoxy-lipoxin $A_4$,
BV, blood vessels;
COX, cyclooxygenase;
EC, endothelial cells;
DSS, dextran sodium sulfate;
GC-MS, gas chromatography-mass spectrometry;
HA, hemoangiogenesis or hemangiogenesis;
HETE, hydroxyeicosatetraenoic acid;
HUVEC, human umbilical vein endothelial cells;
IL, interleukin;
LA, lymphangiogenesis;
LC-UV-MS-MS, liquid chromatography-UV diode array detector-tandem mass spectrometry;
LO, lipoxygenase;
LT, leukotriene;
LV, lymphatic vessels;
LX, lipoxins;
$LXA_4$, lipoxin $A_4$, 5S,6R,15S-trihydroxy-7,9,13-trans-11-cis-eicosatetraenoic acid;
15-epi-$LXA_4$, 5S,6R,15R-trihydroxy-7,9,13-trans-11-cis-eicosatetraenoic acid;
15-R/S-methyl, $LXA_4$, 5S,6R,15R/S-trihydroxy-15-methyl-7,9,13-trans-11-cis-eicosatetraenoic acid, methyl ester;
$LXB_4$, 5S,14R,15S-trihydroxy-6,8,12-trans-10-cis-eicosatetraenoic acid;
MPO, myeloperoxidase;
MTT, 3-(4,5-dimethylthiazol-2-yl)-2,5-diphenyltetrazolium;
NV, neovascularization;
PBS, phosphate buffered saline;
PDA, photodiode array detector;
PG, prostaglandin;
PMN, neutrophils;
PUFA, polyunsaturated fatty acids;
VEGF, vascular endothelial growth factor.

It is to be understood, that throughout the present specification, reference is often made to the therapeutic compounds of the inventions as esters, for example, ATL-1 as a carboxylic ester, i.e., methyl ester. However, all pharmaceutically acceptable salts, esters, amides, and prodrugs, including the carboxylic acid, are considered within the scope of the invention for the $LXA_4$, ATL and $LXB_4$ compounds. For convenience, this terminology has been minimized throughout the description but should be considered as part of the invention. Additionally, it should be understood that the terms $LXA_4$, 15-epi-$LXA_4$ and 15-R/S-methyl, $LXA_4$ also include all pharmaceutically acceptable salts, esters, amides, prodrugs and carboxylic acids.

Additionally, the hydroxyl(s) of ATLs, $LXA_4$s, and $LXB_4$s can be protected by various protecting groups, such as those known in the art. An artisan skilled in the art can readily determine which protecting group(s) can be useful for the protection of the hydroxyl group(s). Standard methods are known in the art and are more fully described in literature. For example, suitable protecting groups can be selected by the skilled artisan and are described in Green and Wuts, "Protecting Groups in Organic Synthesis", John Wiley and Sons, 1991, the teachings of which are incorporated herein by reference. Preferred protecting groups include TMS or TIPPS groups, and preferably acetate or proprionate groups.

For example, one or more hydroxyl groups can be treated with a mild base, such as triethylamine in the presence of an acid chloride or silyl chloride to facilitate a reaction between the hydroxyl ion and the halide. Alternatively, an alkyl halide can be reacted with the hydroxyl ion (generated by a base such as lithium diisopropyl amide) to facilitate ether formation.

It should also be understood that not all hydroxyl groups need be protected. One, two or all three hydroxyl groups can be protected. This can be accomplished by the stoichiometric choice of reagents used to protect the hydroxyl groups. Methods known in the art can be used to separate the mono, di- or tri-protected hydroxy compounds, e.g., HPLC, LC, flash chromatography, gel permeation chromatography, crystallization, distillation, etc.

One advantage of protecting one or more hydroxyl groups of ATL, $LXA_4$, or $LXB_4$ compounds, e.g., via acetates, is the ability to delay the complete metabolic uptake of the compound(s). This is one means by which the compound(s) can remain active over a prolonged period of time as the subject's body slowly removes the protecting group from the hydroxyl under normal physiological conditions. Additionally, by protecting one or more of the hydroxyl groups of these compounds, hydrolysis of the protecting group allows the medication to enter the biochemical pathway of the subject prior to degradation of the parent, unprotected, compound.

Methods to prepare lipoxin analogs (ATLs, $LXA_4$s, or $LXB_4$s) are known in the art. For example, U.S. Pat. Nos. 4,576,758, 4,560,514, 5,079,261, 5,049,681, 5,441,951, 5,648,512, 5,650,435, 6,048,897, 6,100,296, 6,177,468 and 6,316,648 and Japanese Patent Nos. 3,227,922, 63,088,153, 62,198,677 and 1,228,994 describe approaches to prepare lipoxin analogs. Publications by K. C. Nicolaou et al. include approaches to various lipoxin compounds. (For example see, Nicolaou, K. C. et al. Biochim. Biophys. Acta 1003:44-53; Nicolaou, K. C. et al. J. Org. Chem. 54:5527-5535; and Nicolaou, K. C. Angew. Chem. Int. Ed. Engl. 30:1100-1116. Additional literature references for the preparation of lipoxin analogs include Takano, T., S. Fiore, J. F. Maddox, H. R. Brady, N. A. Petasis, and C. N. Serhan. 1997. Aspirin-triggered 15-epi-lipoxin $A_4$ and $LXA_4$ stable analogs are potent inhibitors of acute inflammation: Evidence for anti-inflammatory receptors. *J. Exp. Med.* 185:1693-1704 and Serhan, Charles N., Maddox, Jane F., Petasis, Nicos A., Akritopoulou-Zanze, Irini, Papayianni, Aikaterina, Brady, Hugh R., Colgan, Sean P., and Madara, James L. (1995), Biochemistry, 34, pp. 14609-14614.

Aspirin's therapeutic mechanism of action includes inhibition of COX-derived prostanoids (10). It was discovered that COX-2, when acetylated by ASA, blocks the ability of COX-2 to generate prostanoids, yet this enzyme remains active in endothelial cells, epithelial cells and mononuclear cells and initiates the biosynthesis of new products of cell-cell interactions or transcellular biosynthesis termed aspirin-triggered-15-epi-lipoxins (ATLs) (11). These novel endogenous lipid mediators are the carbon 15 epimers of LX that carry their 15 alcohol in the R configuration compared to their native lipoxin (LX) counterparts and appear to mimic most if not all endogenous LX bioactivities.

To date the actions of ATLs appear to be most relevant in regulating inflammatory responses, since they are generated during cell-cell interactions that can involve, for example, endothelial cells-neutrophils in vivo (12), and display potent inhibitory actions in several key and strategic events in inflammation (12-14). Both LX and ATL actions include inhibiting adhesion and transmigration of neutrophils, and hence can serve as counterregulatory signals to limit and/or regulate leukocyte accumulation that are potentially operative in the dampening and resolution of inflammatory sites (14). Since LX are rapidly generated and inactivated in the local microenvironment, to investigate these actions in vivo, stable analogs of both lipoxins, i.e., $LXA_4$ and ATL were designed that enhance bioavailabilities and these natural compounds bioactivities compared to their native products

(14) and also proved to be ~100 times the potency of ASA (13). The present invention establishes that $LXA_4s$ and ATLs can regulate angiogenesis, a previously unknown and surprising application of these compounds. For example, using a metabolically more stable ATL synthetic analog [15-epi-16-(para-fluoro)-phenoxy-lipoxin $A_4$ (denoted ATL-1)], ATLs and $LXA_4$ compounds, including, 15-epi-$LXA_4$ or 15-R/S-methyl, $LXA_4$ and $LXA_4$ proved to be potent angiostatic eicosanoid in vivo, identifying a new activity for these endogenous mediators that is in sharp contrast to the actions of other eicosanoids and is relevant in several human diseases.

In one aspect, the present invention pertains to methods for the prevention, diminishment or inhibition of angiogenesis. The method is accomplished by the administration of an effective amount of $LXA_4$ and analogs thereof, such as 15-R/S methyl, $LXA_4$, and pharmaceutically acceptable salts, esters, amides or prodrugs thereof, to a subject in need thereof. As a consequence of the action of the therapeutic agent, angiogenesis is prevented, reduced or inhibited in the subject. More specifically, the therapeutic agents can be used in the treatment of the disease states and conditions of the angiogenic disease processes as described below. More specifically, the $LXA_4$ and ATL therapeutic compounds described throughout the specification can be used for the treatment of restenosis, solid tumor tissue growth, neovascularization, e.g., retinal tissue, and reducing blood supply to tissue required to support new growth of tissue in a subject.

In another aspect, the present invention also pertains to methods for the prevention, reduction or inhibition of angiogenesis in tissue of a subject. The method is accomplished by the administration of an effective amount of an aspirin triggered lipoxin (ATL) (15-epi-$LXA_4$, such as 15-epi-16-(para-fluoro)-phenoxy-lipoxin $A_4$ (ATL-1)), and pharmaceutically acceptable salts, esters, amides or prodrugs thereof, to a subject in need thereof. As a consequence of the action of the therapeutic agent, angiogenesis is prevented or inhibited in the subject.

The invention thus provides for a method for the general inhibition of angiogenesis in tissue, and thereby inhibits or prevent events in the tissue which depend upon angiogenesis. Generally, the method comprises administering to the tissue a composition comprising an angiogenesis-inhibiting amount of, for example, ATL-1, $LXA_4$, 15-epi-$LXA_4$ or 15-R/S-methyl, $LXA_4$.

Lymphangiogenesis, an important initial step in tumor metastasis and transplant sensitization, is mediated by the action of VEGF-C and -D on VEGFR3. Lymphangiogenesis is the structural organization of the lymphatic vessels and their growth.

As used herein, the term "angiogenesis" means the formation of new blood vessels into a tissue or organ. Under normal physiological conditions, humans or animals only undergo angiogenesis in very specific restricted situations. For example, angiogenesis is associated with wound healing, fetal and embryonal development and formation of the corpus luteum, endometrium and placenta. The biochemical aspects of angiogenesis are associated with a highly regulated system of angiogenic stimulators and inhibitors. Controlled angiogenesis has been found to be altered in certain disease states and, in many cases, the pathological damage associated with the disease is related to the uncontrolled angiogenesis.

Angiogenesis, the outgrowth of new from preexisting blood vessels, is an important pathogenic aspect of tumor growth, chronic inflammatory diseases, and most blinding ocular conditions. To clearly separate angiogenesis from the process of lymphangiogenesis, it should be understood that blood vascular angiogenesis is referred to as hemangiogenesis (HA). In recent years, much has been learned about the stimulators and inhibitors of HA and lymphangiogenesis, and members of the VEGF family have emerged as prime mediators of both processes. The VEGF growth factor family consists of five members that bind to and activate three distinct receptors. VEGF-A binds to VEGFR1 and VEGFR2, and placental growth factor (P1GF) and VEGF-B bind only to VEGFR1. VEGF-C and VEGF-D bind to VEGFR2 and VEGFR3.

VEGF-A has emerged as the family member principally responsible for normal vasculogenesis and HA. The direct effects of VEGF-A on vascular endothelial cells are mediated principally via VEGFR2 ligation, while, until recently, VEGFR1 was thought to mediate mainly inhibitory or decoy functions. VEGF-A also plays a predominant role in diverse forms of pathological angiogenesis, including those requisite for the rapid growth of solid tumors. For this reason many antiangiogenic agents currently in development for the treatment of cancers have targeted VEGF-A or VEGFR2.

In contrast to HA, lymphangiogenesis is thought to be mediated mainly by the binding of VEGF-C and -D to their high-affinity receptor, VEGFR3. Like HA, lymphangiogenesis has gained much attention recently as an important initial step in tumor pathogenesis. It has been shown that intra- and/or peritumoral lymphangiogenesis increases the risk for metastasis both in animal models and in human tumors. The release of the lymphangiogenic growth factors VEGF-C and -D has been linked to a circulating subfraction of CD14+, VEGFR3-expressing monocytes that are recruited to and activated at the site of tumor growth.

The bioprocesses of controlled and uncontrolled angiogenesis are thought to occur in a similar manner. Endothelial cells and pericytes, surrounded by a basement membrane, form capillary blood vessels. Erosion of the basement membrane promotes angiogenesis by enzymes released by endothelial cells and leukocytes. The endothelial cells, which line the lumen of blood vessels, then break through the basement membrane. Angiogenic stimulants induce the endothelial cells to migrate through the eroded basement membrane. The migrating cells form an offshoot from the parent blood vessel, where the endothelial cells undergo mitosis and proliferate. The endothelial offshoots can merge with each other to form capillary loops, creating a new blood vessel. In the disease state, prevention of angiogenesis could avert the damage caused by the invasion of the new microvascular system.

Persistent, unregulated angiogenesis can occur in a multiplicity of disease states, tumor metastasis and abnormal growth by endothelial cells and supports the pathological damage seen in these conditions. The diverse pathological states created due to unregulated angiogenesis have been grouped together as angiogenic dependent or angiogenic associated diseases. The present invention provides therapies that are directed to control the angiogenic processes thus leading to the abrogation or mitigation of these diseases. With the exception of traumatic wound healing, corpus leuteum formation and embryogenesis, it is believed that angiogenesis processes are associated with undesired, and often life threatening, disease processes and therefore, the use of the present therapeutic methods are selective for the disease, i.e., angiogenesis, and do not have deleterious side effects.

Lipoxins are lipid mediators generated from an essential polyunsaturated fatty acid that is the first dual anti-inflammatory and pro-resolving signals identified in the resolution phase of inflammation. Here the potential of aspirin-triggered lipoxin(LX)$A_4$ analog (ATLa) was investigated in regulating angiogenesis in a corneal neovascularization (NV) murine system in vivo, in which sutures or micropellets containing IL-1β or VEGF-A were placed.

It was determined that the receptors for LXA$_4$ and ALX/Fpr-rs2 were each expressed by the epithelium, stromal fibroblasts, and CD11b$^+$ cells, in both normal and inflamed corneas. Mice were treated with ATLa subconjunctivally (100 ng/10 µl) at 48 h intervals. The control NV group was treated with vehicle only. ATLa-treated eyes had reduced numbers of infiltrating neutrophils and macrophages. The mRNA expression levels of TNF-α, IL-1α, IL-1β, VEGF, VEGF-C, and VEGFR2 were significantly reduced after treatment with these lipid mediators, compared to the control group. Animals treated with these mediators had significantly suppressed suture-induced or IL-1β-induced hemoangiogenesis (HA), but not lymphangiogenesis. Interestingly, ATLa treatment significantly suppressed VEGF-A-induced HA.

These results suggest that ATLa reduces inflammatory corneal HA by early regulation of resolution mechanisms in innate immune responses. In addition, ATLa directly inhibits VEGF-A-mediated angiogenesis and is a potent inhibitor of NV among this new genus of dual anti-inflammatory and pro-resolving lipid mediators.

The following angiogenic diseases can be treated according to the present invention by use of the afore-mentioned ATLs, such as ATL-1 or LXA$_4$s such as 15-R/S-methyl, LXA$_4$. These angiogenic diseases include, but are not limited to, the following:

One example of a disease mediated by angiogenesis is ocular neovascular disease. This disease is characterized by invasion of new blood vessels into the structures of the eye such as the retina or cornea. It is perhaps, one of the most common causes of blindness and is involved in over twenty eye diseases. For example, in age-related macular degeneration, the associated visual problems are caused by an ingrowth of choroidal capillaries through defects in Bruch's membrane with proliferation of fibrovascular tissue beneath the retinal pigment epithelium. Angiogenic damage is also associated with diabetic retinopathy, retinopathy of prematurity, corneal graft rejection, neovascular glaucoma and retrolental fibroplasia. Other diseases associated with corneal neovascularization include, but are not limited to, Vitamin A deficiency, contact lens overwear, atopic keratitis, superior limbic keratitis, epidemic keratoconjunctivitis, pterygium keratitis sicca, sjogrens, acne rosacea, lipid degeneration, chemical burns, bacterial ulcers, fungal ulcers, phylectenulosis, syphilis, Mycobacteria infections, Herpes simplex infections, Herpes zoster infections, Wegeners sarcoidosis, Scleritis, Steven's Johnson syndrome, periphigoid radial keratotomy, protozoan infections, Kaposi sarcoma, Mooren ulcer, Terrien's marginal degeneration, marginal keratolysis, rheumatoid arthritis, systemic lupus, polyarteritis, trauma, and corneal graph rejection.

Diseases associated with retinal/choroidal neovascularization include, but are not limited to, diabetic retinopathy, vein occlusion, artery occlusion, carotid obstructive disease, chronic uveitis/vitritis, mycobacterial infections, Lyme's disease, systemic lupus erythematosis, macular degeneration, sickle cell anemia, sarcoid, syphilis, pseudoxanthoma elasticum, Pagets disease, retinopathy of prematurity, Eales disease, Bests disease, myopia, optic pits, Stargarts disease, pars planitis, chronic retinal detachment, hyperviscosity syndromes, toxoplasmosis, Bechets disease, infections causing a retinitis or choroiditis, presumed ocular histoplasmosis, trauma and post-laser complications. Other diseases include, but are not limited to, diseases associated with rubeosis and diseases caused by the abnormal proliferation of fibrovascular or fibrous tissue including all forms of proliferative vitreoretinopathy.

The present invention provides that lipoxins, such as ATLa, significantly reduce neutrophil and macrophage infiltration, accompanied by down-regulation in the expression of inflammatory cytokines and angiogenic growth factors and receptors. Moreover, these changes have a significantly greater effect in reducing hemoangiogenesis (HA) than lymphangiogenesis (LA).

An even more prevalent disease in which angiogenesis is believed to be involved is rheumatoid arthritis. For example, the blood vessels in the synovial lining of the joints undergo angiogenesis. In addition to forming new vascular networks, the endothelial cells release factors and reactive oxygen species that lead to pannus growth and cartilage destruction. It is believed that the factors involved in angiogenesis can actively contribute to, and help maintain, the chronically inflamed state of rheumatoid arthritis.

It is believed that factors associated with angiogenesis can also have a role in osteoarthritis. The activation of the chondrocytes by angiogenic-related factors contributes to the destruction of the joint. At a later stage, the angiogenic factors can promote new bone formation. The present invention provides therapeutic intervention that prevents the bone destruction and can halt the progress of the disease and provide relief for persons suffering with arthritis.

Both ulcerative colitis and Crohn's disease are known to have histological changes with the ingrowth of new blood vessels into the inflamed tissues. Bartonellosis, can result in a chronic stage that is characterized by proliferation of vascular endothelial cells. An even more insidious pathological role associated with angiogenesis is found in arteriosclerosis. The plaquing of the lumen of blood vessels has been shown to have angiogenic stimulatory activity.

A frequent angiogenic disease of childhood is hemangioma. Generally, the tumors associated with the disease are benign and regress without intervention. In more severe cases, the tumors grow and create clinical complications. Systemic forms of hemangiomas, the hemangiomatoses, have a high mortality rate. Therapy-resistant hemangiomas exist that cannot be treated with therapeutics currently in use.

Angiogenesis is also responsible for damage found in hereditary diseases such as Osler-Weber-Rendu disease, or hereditary hemorrhagic telangiectasia. These diseases are characterized by multiple small angiomas, tumors of blood or lymph vessels. The angiomas are found in the skin and mucous membranes, often accompanied by epistaxis (nosebleeds) or gastrointestinal bleeding and sometimes with pulmonary or hepatic arteriovenous fistula.

Of great concern is the disease state(s) associated with cancer(s). Often times, the cancer is associated with angiogenesis and is identified by solid tumor formation and metastasis. Angiogenic factors are associated with several solid tumors such as neuroblastoma, rhabdomyosarcomas, retinoblastoma, Ewing sarcoma, and osteosarcoma. It is known that a tumor cannot expand without a blood supply to provide nutrients and remove cellular wastes. Tumors in which angiogenesis is important include solid tumors, and benign tumors such as acoustic neuroma, neurofibroma, trachoma and granulomas. Prevention or inhibition of angiogenesis could prevent or halt the growth of these tumors and the subsequent degenerative condition due to the presence of the tumor.

Angiogenesis has also been associated with blood-born tumors including leukemias, any of the various acute or chronic neoplastic diseases of bone marrow in which unrestrained proliferation of white blood cells occurs, usually accompanied by anemia, impaired blood clotting, and enlargement of the lymph nodes, liver, and spleen. It is believed that angiogenesis is significant as a causative factor in the abnormalities in the bone marrow that give rise to leukemia-like tumors.

Angiogenesis is important in two stages of tumor metastasis. The first stage where angiogenesis stimulation is important is in the vascularization of the tumor which allows tumor cells to enter the blood stream and to circulate throughout the body. Once the tumor cells leave the primary site, and find a secondary metastasis site, angiogenesis must occur before the new tumor can grow and expand. Therefore, prevention of angiogenesis could prevent metastasis of tumors and contain the neoplastic growth at the primary site.

In a related embodiment, the present invention can be used in combination with other therapies such as conventional chemotherapy directed against solid tumors and metastases. ATLs, such as ATL-1 or $LXA_4$s, such as 15-R/S-methyl, $LXA_4$, can be administered during or after chemotherapy. In a preferred embodiment, the drug should be administered when the tumor tissue is responding to the toxic assault when vascular tissue is being reorganized to supply blood and nutrients to the tumor tissue. Additionally, the use of ATLs, such as ATL-1 or $LXA_4$s can be used as a phrophylatic treatment after surgical removal of a tumor to prevent angiogenesis from occurring at the treatment site.

Knowledge of the role of angiogenesis in the maintenance and metastasis of tumors has led to a prognostic indicator for breast cancer. The amount of neovascularization found in the primary tumor was determined by counting the microvessel density in the area of the most intense neovascularization in invasive breast carcinoma. A high level of microvessel density was found to correlate with tumor recurrence. Control of angiogenesis by therapeutic means could possibly lead to cessation of the recurrence of the tumors.

Angiogenesis is also involved in normal physiological processes such as reproduction and wound healing. Angiogenesis is an important step in ovulation and also in implantation of the blastula after fertilization. Prevention of angiogenesis could be used to induce amenorrhea, to block ovulation or to prevent implantation by the blastula.

In wound healing, excessive repair or fibroplasia can be a detrimental side effect of surgical procedures and can be caused or exacerbated by angiogenesis. Adhesions are a frequent complication of surgery and lead to problems such as small bowel obstruction.

Restenosis is a process of smooth muscle cell (SMC) migration and proliferation at the site of percutaneous transluminal coronary angioplasty which hampers the success of angioplasty. The migration and proliferation of SMC's during restenosis can be considered a process of angiogenesis which is inhibited by the present methods. Therefore, the invention also contemplates inhibition, reduction or prevention of restenosis by inhibiting, reducing or preventing angiogenesis according to the present methods in a subject following angioplasty procedures. For inhibition or prevention of restenosis, an ATL, such as ATL-1 or an $LXA_4$, such as 15-R/S-methyl, $LXA_4$, can be administered, preferably via intravenous injection, several days before the operation or after the angioplasty procedure for from about 2 to about 28 days, and more typically for about the first 14 days following the procedure.

The term "subject" as used herein refers to any living organism in which an angiogenic response is elicited. The term subject includes, but is not limited to, humans, nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be covered.

The term "mammal" as used herein refers to a living organism capable of eliciting an immune response to an antigen. The term subject includes, but is not limited to, nonhuman primates such as chimpanzees and other apes and monkey species, sheep, pigs, goats, horses, dogs, cats, mice, rats and guinea pigs, and the like.

The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. These can include cations based on the alkali and alkaline earth metals, such as sodium, lithium, potassium, calcium, magnesium and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See, for example, Berge S. M., et al., "Pharmaceutical Salts," J. Pharm. Sci., 1977; 66:1-19 which is incorporated herein by reference).

The term "prodrug" refers to compounds that are rapidly transformed in vivo to yield the parent compound of the above formulae, for example, by hydrolysis in blood. A thorough discussion is provided in T. Higuchi and V. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987, both of which are hereby incorporated by reference. As used herein, a prodrug is a compound that, upon in vivo administration, is metabolized or otherwise converted to the biologically, pharmaceutically or therapeutically active form of the compound. To produce a prodrug, the pharmaceutically active compound is modified such that the active compound will be regenerated by metabolic processes. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, once a pharmaceutically active compound is identified, those of skill in the pharmaceutical art generally can design prodrugs of the compound [see, e.g., Nogrady (1985) Medicinal Chemistry A Biochemical Approach, Oxford University Press, New York, pages 388-392]. Conventional procedures for the selection and preparation of suitable prodrug derivatives are described, for example, in "Design of Prodrugs," ed. H. Bundgaard, Elsevier, 1985. Suitable examples of prodrugs include methyl, ethyl and glycerol esters of the corresponding acid.

The compounds of the invention can be formulated into pharmaceutical compositions as described, vide infra. In a preferred embodiment, the compound can be administered over an extended period of time in a sustained release composition. Sustained release compositions are known in the art and one skilled in the art can formulate an acceptable composition based on generally recognized parameters in the art. In a most preferred embodiment, the glycerol ester can be used in the treatment of inflammatory conditions, described herein, in sustained release compositions, i.e., a transdermal patch, as known in the art. Suitable methods to prepare a transdermal patch can be found in U.S. Pat. No. 5,814,599, 5,846,974 or 4,201,211, the contents of which are incorporated herein by reference. More particularly, the compounds can be delivered transdermally using the types of patch technologies available from Ciba-Geigy Corporation and Alza Corporation. The administration of the pharmaceutical compositions of the present invention can be intermittent, or at a gradual, continuous, constant or controlled rate to a warm-blooded animal, such as a human being. In addition, the time of day and the number of times per day that the pharmaceutical formulation is administered can vary. Administration preferably is such that the active ingredients of the pharmaceutical formulation interact with the inflammatory condition.

A "therapeutically effective amount" is an amount of an ATL, such as ATL-1 or an $LXA_4$, such as 15-R/S-methyl, $LXA_4$, sufficient to produce a measurable inhibition, reduction or prevents angiogenesis in the tissue being treated, i.e., an angiogenesis-inhibiting amount. Inhibition of angiogenesis can be measured in situ by immunohistochemistry or by other methods known to one skilled in the art such as measurement by FAC analysis that monitors P-selectin or VEGF receptors. See also FIGS. 4 and 5.

More specifically, the pharmaceutical compositions of the invention can include a "therapeutically effective amount" or a "prophylactically effective amount" of an antiangiogenic of the invention. A "therapeutically effective amount" refers to an amount effective, at dosages and for periods of time necessary, to achieve the desired therapeutic result, e.g., a diminishment, reduction or prevention of angiogenic factors associated with various disease states or conditions. A therapeutically effective amount of the antiangiogenic can vary according to factors such as the disease state, age, sex, and weight of the individual, and the ability of the antiangiogenic to elicit a desired response in the individual. A therapeutically effective amount is also one in which any toxic or detrimental effects of the antibody or antibody portion are outweighed by the therapeutically beneficial effects.

A "prophylactically effective amount" refers to an amount effective, at dosages and for periods of time necessary, to achieve the desired prophylactic result, i.e. prevent. Typically, since a prophylactic dose is used in subjects prior to or at an earlier stage of disease, the prophylactically effective amount will be less than the therapeutically effective amount.

Dosage regimens can be adjusted to provide the optimum desired response (e.g., a therapeutic or prophylactic response). For example, a single bolus can be administered, several divided doses can be administered over time or the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of an antiangiogenic of the invention is 0.1-20 mg/kg, more preferably 1-10 mg/kg. It is to be noted that dosage values can vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

While it is possible for a compound of the present invention to be administered alone, it is preferable to administer the compound as a pharmaceutical composition.

The invention features an article of manufacture that contains packaging material and a lipoxin analog formulation contained within the packaging material. This formulation contains an at least one lipoxin and the packaging material contains a label or package insert indicating that the formulation can be administered to the subject to treat one or more conditions as described herein, in an amount, at a frequency, and for a duration effective to treat or prevent such condition(s). Such conditions are mentioned throughout the specification and are incorporated herein by reference. Suitable lipoxins are described herein.

More specifically, the invention features an article of manufacture that contains packaging material and at least one lipoxin contained within the packaging material. The packaging material contains a label or package insert indicating that the formulation can be administered to the subject to asthma in an amount, at a frequency, and for a duration effective treat or prevent symptoms associated with such disease states or conditions discussed throughout this specification.

The antiangiogenic compounds of the invention, e.g., an ATL, such as ATL-1 or an $LXA_4$, such as 15-R/S-methyl, $LXA_4$, can be incorporated into pharmaceutical compositions suitable for administration to a subject. Typically, the pharmaceutical composition comprises an antiangiogenic of the invention and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In some instances, it can be beneficial to include isotonic agents, for example, sugars, polyalcohols such as mannitol, sorbitol, or sodium chloride in the composition. Pharmaceutically acceptable carriers can further comprise minor amounts of auxiliary substances such as wetting or emulsifying agents, preservatives or buffers, which enhance the shelf life or effectiveness of the antiangiogenic.

Additionally, the mono-, di- and/or tri-protected alcohols of the compounds of the invention provide for sustained release of the inhibitory/preventative compound. For example, the tri-acyl analogs of the invention provide for such a sustained release of the hydrolyzed tri-hydroxy alcohol(s). The triacylated analogs are thus de-esterified in the blood of the subject.

The antiangiogenics/antineovascular compounds of the invention can be incorporated into a pharmaceutical composition suitable for parenteral administration. Other suitable buffers include but are not limited to, sodium succinate, sodium citrate, sodium phosphate or potassium phosphate. Sodium chloride can be used to modify the toxicity of the solution at a concentration of 0-300 mM (optimally 150 mM for a liquid dosage form). Cryoprotectants can be included for a lyophilized dosage form, principally 0-10% sucrose (optimally 0.5-1.0%). Other suitable cryoprotectants include trehalose and lactose. Bulking agents can be included for a lyophilized dosage form, principally 1-10% mannitol (optimally 2-4%). Stabilizers can be used in both liquid and lyophilized dosage forms, principally 1-50 mM L-Methionine (optimally 5-10 mM). Other suitable bulking agents include glycine, arginine, can be included as 0-0.05% polysorbate-80 (optimally 0.005-0.01%). Additional surfactants include but are not limited to polysorbate 20 and BRIJ surfactants.

The compositions of this invention can be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans. The preferred mode of administration is parenteral (e.g., intravenous, subcutaneous, intraperitoneal, intramuscular). In a preferred embodiment, the antiangiogenic/antineovascular compound is administered by intravenous infusion or injection. In another preferred embodiment, the antiangiogenic/antineovascular compound is administered by intramuscular or subcutaneous injection. In the most preferred embodiment, the antiangiogenic is administered orally.

Alternatively, a preferred embodiment includes the use of the compounds of the invention in eye-drop solutions. This provides for application to the ease to inhibit or prevent ocular diseases such as glaucoma. Generally, the active ingredient, i.e., the compounds of the invention, would be dissolved in an aqueous solution that can be applied directly to the eye.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antigen, antibody or antibody portion) in the required amount in an appropriate solvent with one or a combination of ingredients enumerated above, as required, followed by filtered sterilization.

Generally, dispersions are prepared by incorporating the active compound into a sterile vehicle that contains a basic dispersion medium and the required other ingredients from those enumerated above. In the case of sterile, lyophilized powders for the preparation of sterile injectable solutions, the preferred methods of preparation are vacuum drying and spray-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The antiangiogenic/antineovascular compounds of the present invention can be administered by a variety of methods known in the art. As will be appreciated by the skilled artisan, the route and/or mode of administration will vary depending upon the desired results. In certain embodiments, the active compound can be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

In certain embodiments, an antiangiogenic/antineovascular compound of the invention can be orally administered, for example, with an inert diluent or an assimilable edible carrier. The compound (and other ingredients, if desired) can also be enclosed in a hard or soft shell gelatin capsule, compressed into tablets, or incorporated directly into the subject's diet. For oral therapeutic administration, the compounds can be incorporated with excipients and used in the form of ingestible tablets, buccal tablets, troches, capsules, elixirs, suspensions, syrups, wafers, and the like. To administer a compound of the invention by other than parenteral administration, it can be necessary to coat the compound with, or co-administer the compound with, a material to prevent its inactivation.

The present invention also provides for packaged pharmaceutical compositions useful in the prevention or inhibition of angiogenic, NV activity in a subject. The packaged pharmaceutical composition includes a container holding a therapeutically effective amount of at least one ATL, such as ATL-1 or an $LXA_4$, such as 15-R/S-methyl, $LXA_4$, or a pharmaceutically acceptable salt, esters, amide, or prodrug thereof and instructions for using the therapeutic compound for preventing, reducing or inhibiting angiogenic activity in the subject. Additionally, the present invention provides therapeutically effective amounts of packaged pharmaceutical compositions, e.g., ATL-1, $LXA_4$, 15-epi-$LXA_4$ or 15-R/S-methyl, $LXA_4$ or pharmaceutically acceptable salts, esters, amides, and prodrugs thereof, and instructions useful to treat, i.e., inhibit or prevent, solid tumor tissue growth from undergoing neovascularization, neovascularization from occurring, neovascularization from occurring in retinal tissue, restenosis from occurring following angioplasty in a tissue wherein smooth muscle cell migration occurs, or reducing blood supply to a tissue required to support new growth of new angiogenic tissue.

The present invention also provides angiogenic compounds that facilitate angiogenesis. Surprisingly, configurational isomers of $LXA_4$, $LXA_4$ analogs and ATL analogs, $LXB_4$ and $LXB_4$ analogs and pharmaceutically acceptable salts, esters, amides or prodrugs thereof, provide the opposite effects with regard to revascularization of tissue by the above-identified compounds of the invention. That is, it has been surprisingly discovered that $LXB_4$ and $LXB_4$ analogs have the ability to stimulate regeneration and ingrowth of vascular or epithelial tissue in tissues that are in need of such stimulation. This is especially important in tissue grafting, tissue engineering and prosthetic group sites of attachment. Therefore, the present invention provides methods of tissue regeneration, compounds for such application and packaged pharmaceuticals to accomplish such results.

For example, cardiovascular disease occurs as a consequence of the partial or complete blockage of vessels carrying blood in the coronary vascular system and in peripheral vasculature. Occlusion of the vessel can results in death of tissue previously nourished by the occluded vessels or inability of the vessels to transport sufficient blood supply to regions requiring high blood consumption and accompanying nutrients. Blood vessel occlusion can be partially compensated by the natural process of angiogenesis, in which new conduits are formed to replace the function of the impaired vessels. These new conduits are referred to as "collateral" vessels and can help in the restoration of blood flow to the deprived tissue, thereby constituting natural bypasses around the occluded vessels. However, some individuals for various reasons are unable to generate sufficient collateral vessels to manage the consequences of diminished blood flow from cardiovascular disease.

The $LXB_4$ compounds of the invention can be used to enhance the body's natural ability to repair itself by undergoing natural angiogenesis. As can be seen from the contents of the specification and Figures, vessel growth is stimulated by these unique compounds. This process and use of the present compounds can be utilized for the treatment of wounds. The $LXB_4$ compounds help stimulate the healing process, causing re-epithelialization and vascularization to occur.

"Alkyl" by itself or as part of another substituent refers to a saturated or unsaturated branched, straight-chain or cyclic monovalent hydrocarbon radical having the stated number of carbon atoms (i.e., C1-C6 means one to six carbon atoms) that is derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl, cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. Where specific levels of saturation are intended, the nomenclature "alkanyl," "alkenyl" and/or "alkynyl" is used, as defined below. In preferred embodiments, the alkyl groups are (C1-C6) alkyl.

"Alkanyl" by itself or as part of another substituent refers to a saturated branched, straight-chain or cyclic alkyl derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like. In preferred embodiments, the alkanyl groups are (C1-C6) alkanyl.

"Alkenyl" by itself or as part of another substituent refers to an unsaturated branched, straight-chain or cyclic alkyl having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like. In preferred embodiments, the alkenyl group is (C2-C6) alkenyl.

"Alkynyl" by itself or as part of another substituent refers to an unsaturated branched, straight-chain or cyclic alkyl having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like. In preferred embodiments, the alkynyl group is (C2-C6) alkynyl.

"Alkyldiyl" by itself or as part of another substituent refers to a saturated or unsaturated, branched, straight-chain or cyclic divalent hydrocarbon group having the stated number of carbon atoms (i.e., C1-C6 means from one to six carbon atoms) derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkyldiyl groups include, but are not limited to, methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkanyldiyl, alkenyldiyl and/or alkynyldiyl is used. Where it is specifically intended that the two valencies are on the same carbon atom, the nomenclature "alkylidene" is used. In preferred embodiments, the alkyldiyl group is (C1-C6) alkyldiyl. Also preferred are saturated acyclic alkanyldiyl groups in which the radical centers are at the terminal carbons, e.g., methandiyl (methano); ethan-1,2-diyl (ethano); propan-1,3-diyl (propano); butan-1,4-diyl (butano); and the like (also referred to as alkylenos, defined infra).

"Alkyleno" by itself or as part of another substituent refers to a straight-chain saturated or unsaturated alkyldiyl group having two terminal monovalent radical centers derived by the removal of one hydrogen atom from each of the two terminal carbon atoms of straight-chain parent alkane, alkene or alkyne. The locant of a double bond or triple bond, if present, in a particular alkyleno is indicated in square brackets. Typical alkyleno groups include, but are not limited to, methano; ethylenos such as ethano, etheno, ethyno; propylenos such as propano, prop[1]eno, propa[1,2]dieno, prop[1]yno, etc.; butylenos such as butano, but[1]eno, but[2]eno, buta[1,3]dieno, but[1]yno, but[2]yno, buta[1,3]diyno, etc.; and the like. Where specific levels of saturation are intended, the nomenclature alkano, alkeno and/or alkyno is used. In preferred embodiments, the alkyleno group is (C1-C6) or (C1-C3) alkyleno. Also preferred are straight-chain saturated alkano groups, e.g., methano, ethano, propano, butano, and the like.

"Heteroalkyl," Heteroalkanyl," Heteroalkenyl," Heteroalkynyl," Heteroalkyldiyl" and "Heteroalkyleno" by themselves or as part of another substituent refer to alkyl, alkanyl, alkenyl, alkynyl, alkyldiyl and alkyleno groups, respectively, in which one or more of the carbon atoms are each independently replaced with the same or different heteratoms or heteroatomic groups. Typical heteroatoms and/or heteroatomic groups which can replace the carbon atoms include, but are not limited to, —O—, —S—, —S—O—, —NR'—, —PH—, —S(O)—, —S(O)$_2$—, —S(O)NR'—, —S(O)$_2$NR'—, and the like, including combinations thereof, where each R' is independently hydrogen or (C1-C6) alkyl.

"Cycloalkyl" and "Heterocycloalkyl" by themselves or as part of another substituent refer to cyclic versions of "alkyl" and "heteroalkyl" groups, respectively. For heteroalkyl groups, a heteroatom can occupy the position that is attached to the remainder of the molecule. Typical cycloalkyl groups include, but are not limited to, cyclopropyl; cyclobutyls such as cyclobutanyl and cyclobutenyl; cyclopentyls such as cyclopentanyl and cyclopentenyl; cyclohexyls such as cyclohexanyl and cyclohexenyl; and the like. Typical heterocycloalkyl groups include, but are not limited to, tetrahydrofuranyl (e.g., tetrahydrofuran-2-yl, tetrahydrofuran-3-yl, etc.), piperidinyl (e.g., piperidin-1-yl, piperidin-2-yl, etc.), morpholinyl (e.g., morpholin-3-yl, morpholin-4-yl, etc.), piperazinyl (e.g., piperazin-1-yl, piperazin-2-yl, etc.), and the like.

"Acyclic Heteroatomic Bridge" refers to a divalent bridge in which the backbone atoms are exclusively heteroatoms and/or heteroatomic groups. Typical acyclic heteroatomic bridges include, but are not limited to, —O—, —S—, —S—O—, —NR'—, —PH—, —S(O)—, —S(O)$_2$—, —S(O)NR'—, —S(O)$_2$NR'—, and the like, including combinations thereof, where each R' is independently hydrogen or (C1-C6) alkyl.

"Parent Aromatic Ring System" refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, fluorene, indane, indene, phenalene, tetrahydronaphthalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexylene, indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, tetrahydronaphthalene, triphenylene, trinaphthalene, and the like, as well as the various hydro isomers thereof.

"Aryl" by itself or as part of another substituent refers to a monovalent aromatic hydrocarbon group having the stated number of carbon atoms (i.e., C5-C15 means from 5 to 15 carbon atoms) derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like, as well as the various hydro isomers thereof. In preferred embodiments, the aryl group is (C5-C15) aryl, with (C5-C10) being even more preferred. Particularly preferred aryls are cyclopentadienyl, phenyl and naphthyl.

"Arylaryl" by itself or as part of another substituent refers to a monovalent hydrocarbon group derived by the removal of one hydrogen atom from a single carbon atom of a ring system in which two or more identical or non-identical parent aromatic ring systems are joined directly together by a single bond, where the number of such direct ring junctions is one less than the number of parent aromatic ring systems involved. Typical arylaryl groups include, but are not limited to, biphenyl, triphenyl, phenyl-naphthyl, binaphthyl, biphenyl-naphthyl, and the like. Where the number of carbon atoms in an arylaryl group are specified, the numbers refer to the carbon atoms comprising each parent aromatic ring. For example, (C5-C15) arylaryl is an arylaryl group in which each aromatic ring comprises from 5 to 15 carbons, e.g., biphenyl, triphenyl, binaphthyl, phenylnaphthyl, etc. Preferably, each parent aromatic ring system of an arylaryl group is independently a (C5-C15) aromatic, more preferably a (C5-C10) aromatic. Also preferred are arylaryl groups in which all of the parent aromatic ring systems are identical, e.g., biphenyl, triphenyl, binaphthyl, trinaphthyl, etc.

"Biaryl" by itself or as part of another substituent refers to an arylaryl group having two identical parent aromatic systems joined directly together by a single bond. Typical biaryl groups include, but are not limited to, biphenyl, binaphthyl, bianthracyl, and the like. Preferably, the aromatic ring systems are (C5-C15) aromatic rings, more preferably (C5-C10) aromatic rings. A particularly preferred biaryl group is biphenyl.

"Arylalkyl" by itself or as part of another substituent refers to an acyclic alkyl group in which one of the hydrogen atoms bonded to a carbon atom, typically a terminal or sp$^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylakenyl and/or arylalkynyl is used. In preferred embodiments, the arylalkyl group is (C6-C21) arylalkyl, e.g., the alkanyl, alkenyl or alkynyl moiety of the arylalkyl group is (C1-C6) and the aryl moiety is (C5-C15). In particularly preferred embodiments the arylalkyl group is (C6-C13), e.g., the alkanyl, alkenyl or alkynyl moiety of the arylalkyl group is (C1-C3) and the aryl moiety is (C5-C10).

"Parent Heteroaromatic Ring System" refers to a parent aromatic ring system in which one or more carbon atoms are each independently replaced with the same or different heteroatoms or heteroatomic groups. Typical heteroatoms or heteroatomic groups to replace the carbon atoms include, but are not limited to, N, NH, P, O, S, S(O), S(O)$_2$, Si, etc. Specifically included within the definition of "parent heteroaromatic ring systems" are fused ring systems in which one or more of the rings are aromatic and one or more of the rings are saturated or unsaturated, such as, for example, benzodioxan, benzofuran, chromane, chromene, indole, indoline, xanthene, etc. Also included in the definition of "parent heteroaromatic ring system" are those recognized rings that include common substituents, such as, for example, benzopyrone and 1-methyl-1,2,3,4-tetrazole. Typical parent heteroaromatic ring systems include, but are not limited to, acridine, benzimidazole, benzisoxazole, benzodioxan, benzodioxole, benzofuran, benzopyrone, benzothiadiazole, benzothiazole, benzotriazole, benzoxaxine, benzoxazole, benzoxazoline, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Heteroaryl" by itself or as part of another substituent refers to a monovalent heteroaromatic group having the stated number of ring atoms (e.g., "5-14 membered" means from 5 to 14 ring atoms) derived by the removal of one hydrogen atom from a single atom of a parent heteroaromatic ring system. Typical heteroaryl groups include, but are not limited to, groups derived from acridine, benzimidazole, benzisoxazole, benzodioxan, benzodiaxole, benzofuran, benzopyrone, benzothiadiazole, benzothiazole, benzotriazole, benzoxaxine, benzoxazole, benzoxazoline, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like, as well as the various hydro isomers thereof. In preferred embodiments, the heteroaryl group is a 5-14 membered heteroaryl, with 5-10 membered heteroaryl being particularly preferred.

"Heteroaryl-Heteroaryl" by itself or as part of another substituent refers to a monovalent heteroaromatic group derived by the removal of one hydrogen atom from a single atom of a ring system in which two or more identical or non-identical parent heteroaromatic ring systems are joined directly together by a single bond, where the number of such direct ring junctions is one less than the number of parent heteroaromatic ring systems involved. Typical heteroaryl-heteroaryl groups include, but are not limited to, bipyridyl, tripyridyl, pyridylpurinyl, bipurinyl, etc. Where the number of atoms are specified, the numbers refer to the number of atoms comprising each parent heteroaromatic ring systems. For example, 5-15 membered heteroaryl-heteroaryl is a heteroaryl-heteroaryl group in which each parent heteroaromatic ring system comprises from 5 to 15 atoms, e.g., bipyridyl, tripuridyl, etc. Preferably, each parent heteroaromatic ring system is independently a 5-15 membered heteroaromatic, more preferably a 5-10 membered heteroaromatic. Also preferred are heteroaryl-heteroaryl groups in which all of the parent heteroaromatic ring systems are identical.

"Biheteroaryl" by itself or as part of another substituent refers to a heteroaryl-heteroaryl group having two identical parent heteroaromatic ring systems joined directly together by a single bond. Typical biheteroaryl groups include, but are not limited to, bipyridyl, bipurinyl, biquinolinyl, and the like. Preferably, the heteroaromatic ring systems are 5-15 membered heteroaromatic rings, more preferably 5-10 membered heteroaromatic rings.

"Heteroarylalkyl" by itself or as part of another substituent refers to an acyclic alkyl group in which one of the hydrogen atoms bonded to a carbon atom, typically a terminal or sp$^3$ carbon atom, is replaced with a heteroaryl group. Where specific alkyl moieties are intended, the nomenclature heteroarylalkanyl, heteroarylakenyl and/or heteroarylalkynyl is used. In preferred embodiments, the heteroarylalkyl group is a 6-21 membered heteroarylalkyl, e.g., the alkanyl, alkenyl or alkynyl moiety of the heteroarylalkyl is (C1-C6) alkyl and the heteroaryl moiety is a 5-15-membered heteroaryl. In particularly preferred embodiments, the heteroarylalkyl is a 6-13 membered heteroarylalkyl, e.g., the alkanyl, alkenyl or alkynyl moiety is (C1-C3) alkyl and the heteroaryl moiety is a 5-10 membered heteroaryl.

"Halogen" or "Halo" by themselves or as part of another substituent, unless otherwise stated, refer to fluoro, chloro, bromo and iodo.

"Haloalkyl" by itself or as part of another substituent refers to an alkyl group in which one or more of the hydrogen atoms is replaced with a halogen. Thus, the term "haloalkyl" is meant to include monohaloalkyls, dihaloalkyls, trihaloalkyls, etc. up to perhaloalkyls. For example, the expression "(C1-C2) haloalkyl" includes fluoromethyl, difluoromethyl, trifluoromethyl, 1-fluoroethyl, 1,1-difluoroethyl, 1,2-difluoroethyl, 1,1,1-trifluoroethyl, perfluoroethyl, etc.

The above-defined groups may include prefixes and/or suffixes that are commonly used in the art to create additional well-recognized substituent groups. As examples, "alkyloxy" or "alkoxy" refers to a group of the formula —OR", "alkylamine" refers to a group of the formula —NHR" and "dialkylamine" refers to a group of the formula —NR"R", where each R" is independently an alkyl. As another example, "haloalkoxy" or "haloalkyloxy" refers to a group of the formula —OR'", where R'" is a haloalkyl.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3$^{rd}$ Ed., 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPPS groups), glycol ethers, such as ethylene glycol and propylene glycol derivatives and allyl ethers.

Throughout the following descriptions, it should be understood that where particular double bonding is depicted, it is intended to include both cis and trans configurations. Exemplary formulae are provided with specific configurations, but for completeness, the double bonds can be varied. Not every structural isomer is shown in efforts to maintain brevity of the specification. However, this should not be considered limiting in nature. Additionally, where synthetic schemes are provided, it should be understood that all cis/trans configurational isomers are also contemplated and are within the scope and purview of the synthesis. Again, particular double bonding is depicted in exemplary manner.

The hydroxyl(s) in the lipoxin analogs can be protected by various protecting groups (P), such as those known in the art. An artisan skilled in the art can readily determine which protecting group(s) may be useful for the protection of the hydroxyl group(s). Standard methods are known in the art and are more fully described in literature. For example, suitable protecting groups can be selected by the skilled artisan and are described in Green and Wuts, "Protecting Groups in Organic Synthesis", John Wiley and Sons, Chapters 5 and 7, 1991, the teachings of which are incorporated herein by reference. Preferred protecting groups include methyl and ethyl ethers, TMS or TIPPS groups, acetate (esters) or propionate groups and glycol ethers, such as ethylene glycol and propylene glycol derivatives.

For example, one or more hydroxyl groups can be treated with a mild base, such as triethylamine in the presence of an acid chloride or silyl chloride to facilitate a reaction between the hydroxyl ion and the halide. Alternatively, an alkyl halide can be reacted with the hydroxyl ion (generated by a base such as lithium diisopropyl amide) to facilitate ether formation.

It should also be understood that for the lipoxin analogs, not all hydroxyl groups need be protected. One, two or all three hydroxyl groups can be protected. This can be accomplished by the stoichiometric choice of reagents used to protect the hydroxyl groups. Methods known in the art can be used to separate the di- or tri-protected hydroxy compounds, e.g., HPLC, LC, flash chromatography, gel permeation chromatography, crystallization, distillation, etc.

It should be understood that there are one or more chiral centers in each of the above-identified compounds. It should understood that the present invention encompasses all stereochemical forms, e.g., enantiomers, diastereomers and racemates of each compound. Where asymmetric carbon atoms are present, more than one stereoisomer is possible, and all possible isomeric forms are intended to be included within the structural representations shown. Optically active (R) and (S) isomers may be resolved using conventional techniques known to the ordinarily skilled artisan. The present invention is intended to include the possible diastereiomers as well as the racemic and optically resolved isomers.

Where carbon-carbon double bonds exist, the configurational chemistry can be either cis (Z) or trans (E) and the depictions throughout the specification are not meant to be limiting. The depictions are, in general, presented based upon the configurational chemistry of related AA compounds, and although not to be limited by theory, are believed to possess similar configuration chemistry.

Throughout the specification carbon-carbon bonds in particular have been "distorted" for ease to show how the bonds may ultimately be positioned relative one to another. For example, it should be understood that acetylenic portions of the lipoxins actually do include a geometry of approximately 180 degrees, however, for aid in understanding of the synthesis and relationship between the final product(s) and starting materials, such angles have been obfuscated to aid in comprehension.

It should be understood that hydrogenation of acetylenic portions of the lipoxin analog may result in one or more products.

It is intended that all possible products are included within this specification. For example, hydrogenation of acetylenic lipoxin analogs can produce a mixture of products—monoethylene products (cis or trans "monoene"-acetylene; acetylene-cis or trans "monoene". All products can be separated and identified by HPLC, GC, MS, NMR, IR.

Known techniques in the art can be used to convert the carboxylic acid/ester functionality of the lipoxin into carboxamides, thioesters, nitrile, carbamates, thiocarbamates, etc. and are incorporated herein. The appropriate moieties, such as amides, can be further substituted as is known in the art.

In general, the lipoxin analogs of the invention are bioactive as alcohols. Enzymatic action or reactive oxygen species attack at the site of inflammation or degradative metabolism. Such interactions with the hydroxyl(s) of the lipoxin molecule can eventually reduce physiological activity as depicted below:

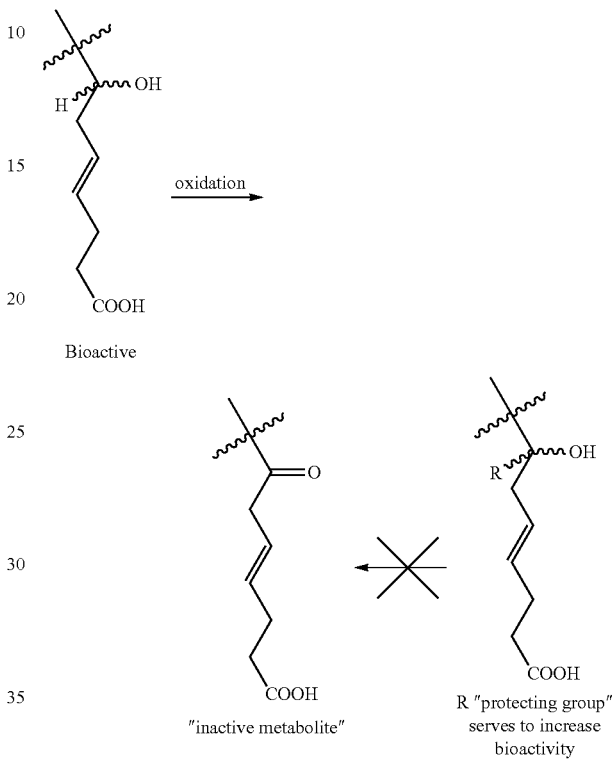

The use of "R" groups with secondary bioactive alcohols, in particular, serves to increase the bioavailability and bioactivity of the lipoxin by inhibiting or diminishing the potential for oxidation of the alcohol to a ketone producing an inactive metabolite. The R "protecting groups" include, for example, linear and branched, substituted and unsubstituted alkyl groups, aryl groups, alkylaryl groups, phenoxy groups, and halogens.

Generally the use of "R protection chemistry" is not necessary with vicinal diols within the lipoxin. Typically vicinal diols are not as easily oxidized and therefore, generally do not require such protection by substitution of the hydrogen atom adjacent to the oxygen atom of the hydroxyl group. Although it is generally considered that such protection is not necessary, it is possible to prepare such compounds where each of the vicinal diol hydroxyl groups, independently, could be "protected" by the substitution of the hydrogen atom adjacent to the oxygen atom of the hydroxyl group with an "R protecting group" as described above.

Suitable lipoxin analogs, including ATLs, $LXA_4s$ and $LXB_4s$ encompassed by the present invention include those having the following characteristics.

The instant lipoxins comprising an "active region" and a "metabolic transformation region" as both terms are defined herein are generally of the following structure: wherein $R_1$ can be wherein $R_1$ can be

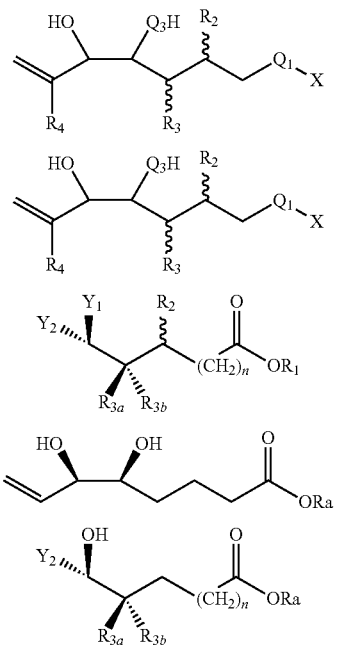

and $R_2$ can be

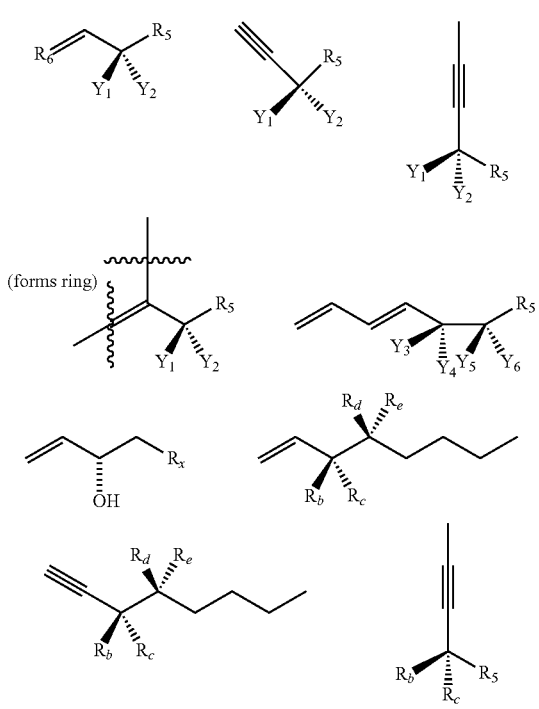

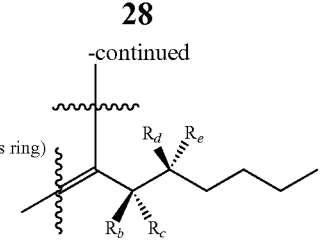

In one embodiment, the lipoxin analogs of this invention have the following structural formula I:

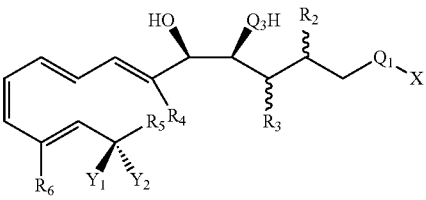

wherein X is $R_1$, $OR_1$, or $SR_1$;
wherein $R_1$ is
(i) a hydrogen atom;
(ii) an alkyl of 1 to 8 carbons atoms, inclusive, which can be straight chain or branched;
(iii) a cycloalkyl of 3 to 10 carbon atoms, inclusive;
(iv) an aralkyl of 7 to 12 carbon atoms;
(v) phenyl;
(vi) substituted phenyl

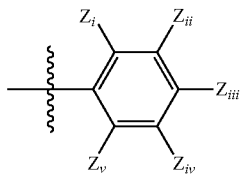

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which can be a straight chain or branched, and hydroxyl;
(vii) a detectable label molecule; or
(viii) a straight or branched chain alkenyl of 2 to 8 carbon atoms, inclusive;
wherein $Q_1$ is (C=O), $SO_2$ or (CN);
wherein $Q_3$ is O, S or NH;
wherein one of $R_2$ and $R_3$ is a hydrogen atom and the other is
(a) a hydrogen atom;
(b) an alkyl of 1 to 8 carbon atoms, inclusive, which can be straight chain or branched;
(c) a cycloalkyl of 3 to 6 carbon atoms, inclusive;
(d) an alkenyl of 2 to 8 carbon atoms, inclusive, which can be straight chain or branched; or
(e) $R_aQ_2R_b$
wherein $Q_2$ is —O— or —S—;
wherein $R_a$ is alkylene of 0 to 6 carbons atoms, inclusive, which can be straight chain or branched; and wherein $R_b$ is alkyl of 0 to 8 carbon atoms, inclusive, which can be straight chain or branched;

wherein R$_4$ is (a) a hydrogen atom;

(b) an alkyl of 1 to 6 carbon atoms, inclusive, which can be straight chain or branched;

wherein Y$_1$ or Y$_2$ is —OH, methyl, or —SH and wherein the other is (a) a hydrogen atom (b) CH$_a$Z$_b$ where a+b=3, a=0 to 3, b=0 to 3; and each Z, independently, is a cyano, a nitro, or a halogen atom;

(c) an alkyl of 2 to 4 carbon atoms, inclusive, straight chain or branched; or (d) an alkoxy of 1 to 4 carbon atoms, inclusive;

or Y$_1$ and Y$_2$ taken together are (a) =NH; or (b) =O;

wherein R$_5$ is (a) an alkyl of 1 to 9 carbon atoms which can be straight chain or branched;

(b) —(CH$_2$)$_n$—R$_i$ wherein n=0 to 4 and R$_i$ is (i) a cycloalkyl of 3 to 10 carbon atoms, inclusive;

(ii) a phenyl; or (iii) substituted phenyl

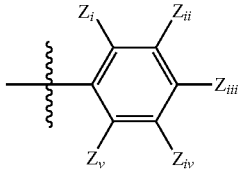

wherein Z$_i$, Z$_{ii}$, Z$_{iii}$, Z$_{iv}$ and Z$_v$ are each independently selected from —NO$_2$, —CN, —C(=O)—R$_1$, —SO$_3$H, a hydrogen atom, halogen, methyl, —OR$_x$, wherein R$_x$ is 1 to 8 carbon atoms, inclusive, which can be a straight chain or branched, and hydroxyl;

(c) R$_a$Q$_a$R$_b$ wherein Q$_a$ is O or S;

wherein R$_a$ is alkylene of 0 to 6 carbons atoms, inclusive, which can be straight chain or branched;

wherein R$_b$ is alkyl of 0 to 8 carbon atoms, inclusive, which can be straight chain or branched;

(d) —C(R$_{iii}$)(R$_{iv}$)—R$_i$, wherein R$_{iii}$ and R$_{iv}$ are each, independently:

(i) a hydrogen atom;

(ii) CH$_a$Z$_b$ where a+b=3, a=0 to 3, b=0+3, and wherein each Z, independently, is a cyano, a nitro, or a halogen atom;

(e) a haloalkyl of 1 to 8 carbon atoms, inclusive, and 1 to 6 halogen atoms, inclusive, straight chain or branched; and wherein R$_6$ is (a) a hydrogen atom;

(b) an alkyl from 1 to 4 carbon atoms, inclusive, straight chain or branched;

(c) a halogen.

In one embodiment of this invention, the lipoxin analogs have the following structure II:

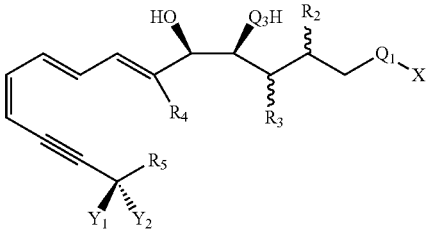

wherein X is R$_1$, OR$_1$, or SR$_1$; wherein R$_1$ is (i) a hydrogen atom;

(ii) an alkyl of 1 to 8 carbons atoms, inclusive, which can be straight chain or branched;

(iii) a cycloalkyl of 3 to 10 carbon atoms, inclusive;

(iv) an aralkyl of 7 to 12 carbon atoms;

(v) a phenyl;

(vi) substituted phenyl

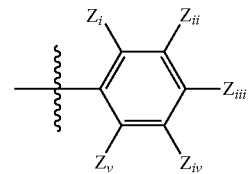

wherein Z$_i$, Z$_{ii}$, Z$_{iii}$, Z$_{iv}$ and Z$_v$ are each independently selected from —NO$_2$, —CN, —C(=O)—R$_1$, —SO$_3$H, a hydrogen atom, halogen, methyl, —OR$_x$, wherein R$_x$ is 1 to 8 carbon atoms, inclusive, which can be a straight chain or branched, and hydroxyl;

(vii) a detectable label molecule, such as but not limited to fluorescent labels; or (viii) an alkenyl of 2 to 8 carbon atoms, inclusive, straight chain or branched;

wherein Q$_1$ is (C=O), SO$_2$ or (C=N);

wherein Q$_3$ is O, S or NH;

wherein one of R$_2$ and R$_3$ is hydrogen and the other is (a) a hydrogen atom;

(b) an alkyl of 1 to 8 carbon atoms, inclusive, which can be straight chain or branched;

(c) a cycloalkyl of 3 to 6 carbon atoms, inclusive;

(d) an alkenyl of 2 to 8 carbon atoms, inclusive, which can be straight chain or branched; or (e) R$_a$Q$_2$R$_b$ wherein Q$_2$ is —O— or —S—;

wherein R$_a$ is alkylene of 0 to 6 carbons atoms, inclusive, which can be straight chain or branched;

wherein R$_b$ is alkyl of 0 to 8 carbon atoms, inclusive, which can be straight chain or branched;

wherein R$_4$ is (a) a hydrogen atom;

(b) alkyl of 1 to 6 carbon atoms, inclusive, which can be straight chain or branched;

wherein Y$_1$ or Y$_2$ is —OH, methyl, —H or —SH and wherein the other is (a) a hydrogen atom;

(b) CH$_a$Z$_b$ where a+b=3, a=0 to 3, b=0 to 3 wherein each Z, independently, is a cyano, a nitro, or a halogen atom;

(c) an alkyl of 2 to 4 carbon atoms, inclusive, straight chain or branched;

(d) an alkoxy of 1 to 4 carbon atoms, inclusive; or $Y_1$ and $Y_2$ taken together are
(a) =NH; or
(b) =O;
wherein $R_5$ is
(a) an alkyl of 1 to 9 carbon atoms which can be straight chain or branched;
(b) —(CH$_2$)$_n$—R$_i$
wherein n=0 to 4 and R$_i$ is
(i) a cycloalkyl of 3 to 10 carbon atoms, inclusive;
(ii) phenyl; or
(iii) substituted phenyl

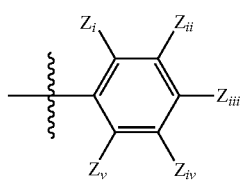

wherein $Z_i$, $Z_{ii}$, $Z_{iii}$, $Z_{iv}$ and $Z_v$ are each independently selected from —NO$_2$, —CN, —C(=O)—R$_1$, —SO$_3$H, a hydrogen atom, halogen, methyl, —OR$_x$, wherein R$_x$ is 1 to 8 carbon atoms, inclusive, which can be a straight chain or branched, and hydroxyl;
(c) R$_a$Q$_a$R$_b$
wherein Q$_a$ is —O— or —S—; and
wherein R$_a$ is alkylene of 0 to 6 carbons atoms, inclusive, which can be straight chain or branched;
wherein R$_b$ is alkyl of 0 to 8 carbon atoms, inclusive, which can be straight chain or branched;
(d) —C(R$_{iii}$)(R$_{iv}$)—R$_i$
wherein R$_{iii}$ and R$_{iv}$ are each independently:
(i) a hydrogen atom; or
(ii) CH$_a$Z$_b$ where a+b=3, a=0 to 3, b=0+3
wherein each Z, independently, is a cyano, a nitro, or a halogen atom,
(e) a haloalkyl of 1 to 8 carbon atoms, inclusive, and 1 to 6 halogen atoms, inclusive, straight chain or branched.

In one embodiment of this invention, the lipoxin analogs have the following structure III:

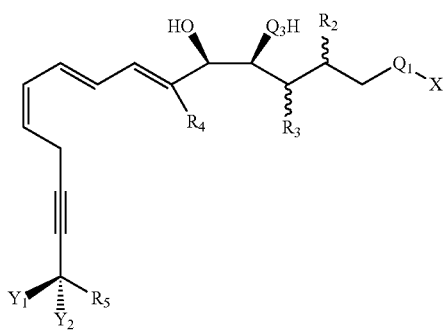

wherein X is R$_1$, OR$_1$, or SR$_1$; wherein R$_1$ is
(i) a hydrogen atom;
(ii) an alkyl of 1 to 8 carbons atoms, inclusive, which can be straight chain or branched;
(iii) a cycloalkyl of 3 to 10 carbon atoms, inclusive;
(iv) an aralkyl of 7 to 12 carbon atoms;
(v) phenyl;
(vi) substituted phenyl

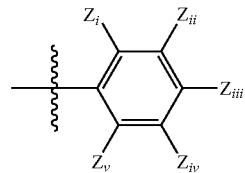

wherein $Z_i$, $Z_{ii}$, $Z_{iii}$, $Z_{iv}$ and $Z_v$ are each independently selected from —NO$_2$, —CN, —C(=O)—R$_1$, —SO$_3$H, a hydrogen atom, halogen, methyl, —OR$_x$, wherein R$_x$ is 1 to 8 carbon atoms, inclusive, which can be a straight chain or branched, and hydroxyl;
(vii) a detectable label molecule; or
(viii) an alkenyl of 2 to 8 carbon atoms, inclusive, straight chain or branched;
wherein Q$_1$ is (C=O), SO$_2$ or (C=N);
wherein Q$_3$ is O, S or NH;
wherein one of R$_2$ and R$_3$ is hydrogen atom and the other is
(a) a hydrogen atom;
(b) an alkyl of 1 to 8 carbon atoms, inclusive, which can be straight chain or branched;
(c) a cycloalkyl of 3 to 6 carbon atoms, inclusive;
(d) an alkenyl of 2 to 8 carbon atoms, inclusive, which can be straight chain or branched; or
(e) R$_a$Q$_2$R$_b$
wherein Q$_2$ is —O— or —S—;
wherein R$_a$ is alkylene of 0 to 6 carbons atoms, inclusive, which can be straight chain or branched;
wherein R$_b$ is alkyl of 0 to 8 carbon atoms, inclusive, which can be straight chain or branched;
wherein R$_4$ is
(a) a hydrogen atom; or
(b) an alkyl of 1 to 6 carbon atoms, inclusive, which can be straight chain or branched;
wherein $Y_1$ or $Y_2$ is hydroxyl, methyl, hydrogen or thiol and wherein the other is
(a) a hydrogen atom;
(b) CH$_a$Z$_b$
where a+b=3, a 0 to 3, b=0 to 3
wherein each Z, independently, is a cyano, a nitro, or a halogen atom;
(c) an alkyl of 2 to 4 carbon atoms, inclusive, straight chain or branched;
(d) an alkoxy of 1 to 4 carbon atoms, inclusive; or $Y_1$ and $Y_2$ taken together are
(a) =NH; or
(b) =O; and
wherein $R_5$ is
(a) an alkyl of 1 to 9 carbon atoms which can be straight chain or branched;
(b) —(CH$_2$)$_n$—R$_i$ wherein n=0 to 4 and $R_i$ is
(i) cycloalkyl of 3 to 10 carbon atoms, inclusive;
(ii) phenyl;
(iii) substituted phenyl

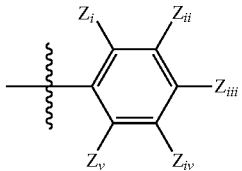

wherein $Z_i$, $Z_{ii}$, $Z_{iii}$, and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which can be a straight chain or branched, and hydroxyl;
(c) $R_aQ_aR_b$
wherein $Q_a$ is —O— or —S—;
wherein $R_a$ is alkylene of 0 to 6 carbons atoms, inclusive, which can be straight chain or branched;
wherein $R_b$ is alkyl of 0 to 8 carbon atoms, inclusive, which can be straight chain or branched; or
(d) —C($R_{iii}$)($R_{iv}$)—$R_i$
wherein $R_{iii}$ and $R_{iv}$ are each independently:
(i) a hydrogen atom; or
(ii) $CH_aZ_b$ where a+b=3, a=0 to 3, b=0+3
wherein each Z, independently, is a cyano, a nitro, or a halogen atom,
(e) a haloalkyl of 1 to 8 carbon atoms, inclusive, and 1 to 6 halogen atoms, inclusive, straight chain or branched.

In another embodiment of this invention, lipoxin analogs have the following structural formula IV:

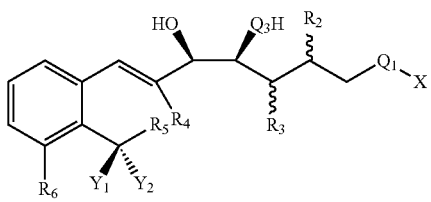

wherein X is $R_1$, $OR_1$, or $SR_1$; wherein $R_1$ is
(i) a hydrogen atom;
(ii) an alkyl of 1 to 8 carbons atoms, inclusive, which can be straight chain or branched;
(iii) a cycloalkyl of 3 to 10 carbon atoms, inclusive;
(iv) an aralkyl of 7 to 12 carbon atoms;
(v) phenyl;
(vi) substituted phenyl

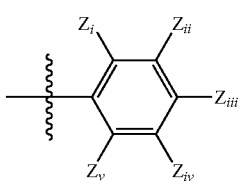

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which can be a straight chain or branched, and hydroxyl;
(vii) a detectable label molecule; or
(viii) an alkenyl of 2 to 8 carbon atoms, inclusive, straight chain or branched;
wherein $Q_1$ is (C=O), $SO_2$ or (CN);
wherein $Q_3$ is O, S or NH;
wherein one of $R_2$ and $R_3$ is hydrogen and the other is
(a) a hydrogen atom;
(b) an alkyl of 1 to 8 carbon atoms, inclusive, which can be straight chain or branched;
(c) a cycloalkyl of 3 to 6 carbon atoms, inclusive;
(d) an alkenyl of 2 to 8 carbon atoms, inclusive, which can be straight chain or branched; or
(e) $R_aQ_2R_b$
wherein $Q_2$ is —O— or —S—;
wherein $R_a$ is alkylene of 0 to 6 carbons atoms, inclusive, which can be straight chain or branched;
wherein $R_b$ is alkyl of 0 to 8 carbon atoms, inclusive, which can be straight chain or branched;
wherein $R_4$ is
(a) a hydrogen atom; or
(b) an alkyl of 1 to 6 carbon atoms, inclusive, which can be straight chain or branched;
wherein $Y_1$ or $Y_2$ is —OH, methyl, or —SH and wherein the other is
(a) a hydrogen atom;
(b) $CH_aZ_b$ where a+b=3, a=0 to 3, b=0 to 3, wherein each Z, independently, is a cyano, a nitro, or a halogen atom;
(c) an alkyl of 2 to 4 carbon atoms, inclusive, straight chain or branched; or
(d) an alkoxy of 1 to 4 carbon atoms, inclusive;
or $Y_1$ and $Y_2$ taken together are
(a) =NH; or
(b) =O;
wherein $R_5$ is
(a) an alkyl of 1 to 9 carbon atoms which can be straight chain or branched;
(b) —$(CH_2)_n$—$R_i$
wherein n=0 to 4 and $R_i$ is
(i) a cycloalkyl of 3 to 10 carbon atoms, inclusive;
(ii) phenyl; or
(iii) substituted phenyl

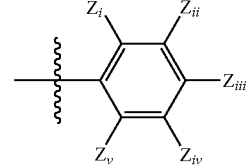

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which can be a straight chain or branched, and hydroxyl;
(c) $R_aQ_aR_b$
wherein $Q_a$ is —O— or —S—;
wherein $R_a$ is alkylene of 0 to 6 carbons atoms, inclusive, which can be straight chain or branched;
wherein $R_b$ is alkyl of 0 to 8 carbon atoms, inclusive, which can be straight chain or branched;
(d) —C($R_{iii}$)($R_{iv}$)—$R_i$ wherein $R_{iii}$ and $R_{iv}$ are each independently:
(i) a hydrogen atom; or
(ii) $CH_aZ_b$ where a+b=3, a=0 to 3, b=0+3 and
wherein each Z, independently, is a cyano, a nitro, or a halogen atom; or
(e) haloalkyl of 1 to 8 carbon atoms, inclusive, and 1 to 6 halogen atoms, inclusive, straight chain or branched; and
wherein $R_6$ is
(a) a hydrogen atom;
(b) an alkyl from 1 to 4 carbon atoms, inclusive, straight chain or branched; or
(c) a halogen atom.

In another embodiment of this invention, lipoxin analogs have the following structural formula V:

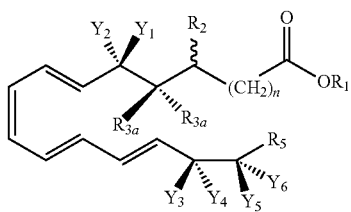

wherein $R_1$ is
(i) a hydrogen atom;
(ii) an alkyl of 1 to 8 carbons atoms, inclusive, which can be straight chain or branched;
(iii) a cycloalkyl of 3 to 10 carbon atoms, inclusive;
(iv) an aralkyl of 7 to 12 carbon atoms;
(v) phenyl;
(vi) substituted phenyl

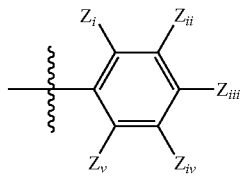

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which can be a straight chain or branched, and hydroxyl;
(vii) a detectable label molecule; or
(viii) an alkenyl of 2 to 8 carbon atoms, inclusive, straight chain or branched;
wherein n=1 to 10, inclusive;
wherein $R_2$, $R_{3a}$, and $R_{3b}$ are each independently:
(a) a hydrogen atom;
(b) an alkyl of 1 to 8 carbon atoms, inclusive, which can be straight chain or branched;
(c) a cycloalkyl of 3 to 6 carbon atoms, inclusive;
(d) an alkenyl of 2 to 8 carbon atoms, inclusive, which can be straight chain or branched; or
(e) $R_aQ_2R_b$
wherein $Q_2$ is —O— or —S—;
wherein $R_a$ is alkylene of 0 to 6 carbons atoms, inclusive, which can be straight chain or branched; and wherein $R_b$ is alkyl of 0 to 8 carbon atoms, inclusive, which can be straight chain or branched;
wherein $Y_1$ or $Y_2$ is —OH, methyl, hydrogen, or —SH and wherein the other is
(a) a hydrogen atom;
(b) $CH_aZ_b$
where a+b=3, a=0 to 3, b=0 to 3, and
wherein each Z, independently, is a cyano, a nitro, or a halogen atom;
(c) an alkyl of 2 to 4 carbon atoms, inclusive, straight chain or branched;
(d) an alkoxy of 1 to 4 carbon atoms, inclusive, straight chain or branched;
or $Y_1$ and $Y_2$ taken together are
(a) =NH; or
(b) =O;
wherein $Y_3$ or $Y_4$ is —OH, methyl, hydrogen, or —SH and wherein the other is
(a) a hydrogen atom;
(b) $CH_aZ_b$
wherein a+b=3, a=0 to 3, b=0 to 3,
and wherein each Z, independently, is a cyano, a nitro, or a halogen atom;
(c) an alkyl of 2 to 4 carbon atoms, inclusive, straight chain or branched;
(d) an alkoxy of 1 to 4 carbon atoms, inclusive, straight chain or branched;
or $Y_3$ and $Y_4$ taken together are
(a) =NH; or
(b) =O;
wherein $Y_5$ or $Y_6$ is —OH, methyl, hydrogen, or —SH and wherein the other is
(a) a hydrogen atom;
(b) $CH_aZ_b$
where a+b=3, a=0 to 3, b=0 to 3
wherein each Z, independently, is a cyano, a nitro, or a halogen atom;
(c) an alkyl of 2 to 4 carbon atoms, inclusive, straight chain or branched;
(d) an alkoxy of 1 to 4 carbon atoms, inclusive, straight chain or branched;
or $Y_5$ and $Y_6$ taken together are
(a) =NH; or
(b) =O;
wherein $R_5$ is
(a) an alkyl of 1 to 9 carbon atoms which can be straight chain or branched;
(b) —$(CH_2)_n$—$R_i$
wherein n=0 to 4 and $R_i$ is
(i) a cycloalkyl of 3 to 10 carbon atoms, inclusive;
(ii) phenyl; or
(iii) substituted phenyl

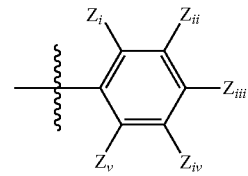

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which can be a straight chain or branched, and hydroxyl;
(c) —$R_aQ_aR_b$
wherein $Q_a$ is —O— or —S—; and wherein $R_a$ is alkylene of 0 to 6 carbons atoms, inclusive, which can be straight chain or branched;

wherein $R_b$ is either alkyl of 0 to 8 carbon atoms, inclusive, which can be straight chain or branched or substituted phenyl;

(d) —C($R_{iii}$)($R_{iv}$)—$R_i$ wherein $R_{iii}$ and $R_{iv}$ are each independently:
(i) a hydrogen atom; or
(ii) $CH_aZ_b$ where a+b=3, a=0 to 3, b=0+3, and
wherein each Z, independently, is a cyano, a nitro, or a halogen atom; or (e) haloalkyl of 1 to 8 carbon atoms, inclusive, and 1 to 6 halogen atoms, inclusive, straight chain or branched.

In another embodiment of this invention, lipoxin analogs have the structural formula VI:

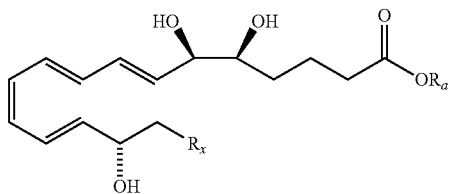

wherein $R_a$ is
(a) a hydrogen atom; or
(b) alkyl of 1 to 8 carbon atoms;
wherein $R_x$ is
(a) substituted phenyl

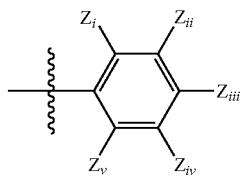

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which can be a straight chain or branched, and hydroxyl;

(b) a substituted phenoxy

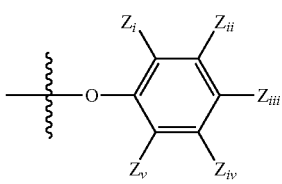

wherein $Z_i$ through $Z_v$ are as defined above; or

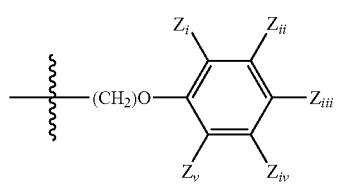

wherein $Z_i$ through $Z_v$ are as defined above.

In another preferred embodiment of this invention, lipoxin analogs have the following structural formula VII:

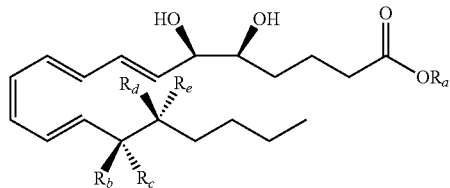

wherein $R_a$ is
(a) a hydrogen atom; or
(b) an alkyl of 1 to 8 carbon atoms;
wherein $R_b$ and $R_c$ are each independently:
(a) a hydrogen atom;
(b) a hydroxyl, or a thiol;
(c) a methyl or a halomethyl;
(d) a halogen;
(e) an alkoxy of 1 to 3 carbon atoms;
wherein $R_d$ and $R_e$ are each independently:
(a) a hydrogen atom;
(b) a hydroxyl, or thiol;
(c) a methyl or halomethyl;
(d) a halogen;
(e) an alkoxy of 1 to 3 carbon atoms; or
(f) an alkyls or haloalkyl of 2 to 4 carbon atoms, inclusive, which can be straight chain or branched.

In another preferred embodiment of this invention, the lipoxin analogs have the structural formula VIII:

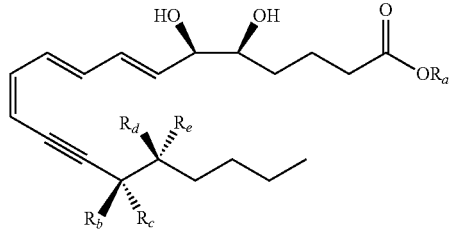

wherein $R_a$ is
(a) a hydrogen atom; or
(b) an alkyl of 1 to 8 carbon atoms;
wherein $R_b$ and $R_c$ are each independently:
(a) a hydrogen atom;
(b) a hydroxyl or a thiol;
(c) a halomethyl;
(d) a halogen;
(e) an alkyl of 1 to 3 carbon atoms, inclusive, straight chain or branched; or
(f) an alkoxy of 1 to 3 carbon atoms, inclusive;
wherein $R_d$ and $R_e$ are each independently:
(a) a hydrogen atom;
(b) a hydroxyl, or a thiol;
(c) a methyl or a halomethyl;
(d) a halogen;
(e) an alkoxy of 1 to 3 carbon atoms, inclusive; or
(f) an alkyl or haloalkyl of 2 to 4 carbon atoms, inclusive, which can be straight chain or branched.

In another embodiment of this invention, the lipoxin analogs have the structural formula IX:

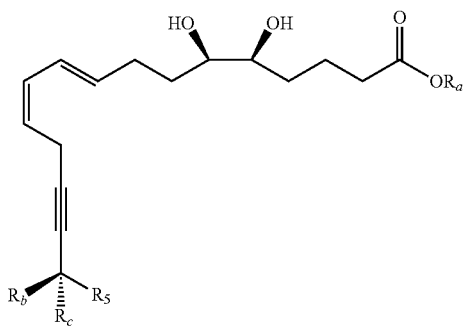

wherein $R_a$ is
  (a) a hydrogen atom; or
  (b) an alkyl of 1 to 8 carbon atoms;
wherein $R_b$ and $R_c$ are each independently:
  (a) a hydrogen atom;
  (b) a hydroxyl or thiol;
  (c) a halomethyl;
  (d) a halogen;
  (e) an alkyl of 1 to 3 carbon atoms, inclusive, straight chain or branched;
  (f) an alkoxy of 1 to 3 carbon atoms, inclusive; and
wherein $R_5$ is
  (a) an alkyl of 1 to 9 carbon atoms which can be straight chain or branched;
  (b) —$(CH_2)_n$—$R_i$
wherein n=0 to 4 and $R_i$ is
  (i) a cycloalkyl of 3 to 10 carbon atoms, inclusive;
  (ii) phenyl; or
  (iii) substituted phenyl

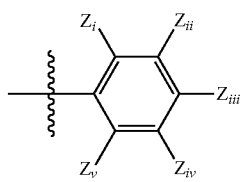

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which can be a straight chain or branched, and hydroxyl;
  (c) $R_a Q_a R_b$
  wherein $Q_a$ is —O— or —S—;
  wherein $R_a$ is alkylene of 0 to 6 carbons atoms, inclusive, which can be straight chain or branched;
  wherein $R_b$ is either alkyl of 0 to 8 carbon atoms, inclusive, which can be straight chain or branched or substituted phenyl;
  (d) —$C(R_{iii})(R_{iv})R_i$
  wherein $R_{iii}$ and $R_{iv}$ are each, independently:
    (i) a hydrogen atom; or
    (ii) $CH_a Z_b$ where a+b=3, a=0 to 3, b=0+3
  wherein each Z, independently, is a cyano, a nitro, or a halogen atom; or
  (e) haloalkyl of 1 to 8 carbon atoms, inclusive, and 1 to 6 halogen atoms, inclusive, straight chain or branched.

In another preferred embodiment, the compounds have the structural formula X:

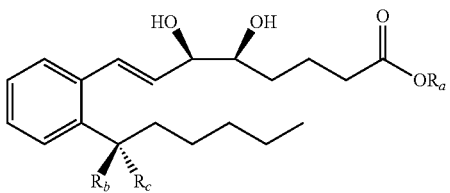

wherein $R_a$ is
  (a) a hydrogen atom; or
  (b) alkyl of 1 to 8 carbon atoms, inclusive, straight chain or branched; and
wherein $R_b$ and $R_c$ are each, independently:
  (a) a hydrogen atom;
  (b) a hydroxyl or a thiol;
  (c) a halomethyl;
  (d) a halogen;
  (e) an alkyl of 1 to 3 carbon atoms, inclusive, straight chain or branched;
  (f) an alkoxy of 1 to 3 carbon atoms, inclusive.

In another preferred embodiment, the compounds have the structural formula XI:

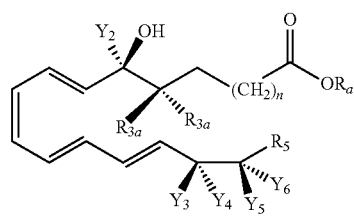

wherein $R_a$ is
  (i) a hydrogen atom;
  (ii) an alkyl of 1 to 8 carbons atoms, inclusive, which can be straight chain or branched; or
  (iii) a detectable label molecule;
wherein n=1 to 10, inclusive;
wherein $Y_2$, $R_3a$, and $R_3b$ are each, independently:
  (a) a hydrogen atom;
  (b) an alkyl of 1 to 8 carbon atoms, inclusive, which can be straight chain or branched;
  (c) a cycloalkyl of 3 to 6 carbon atoms, inclusive;
  (d) an alkenyl of 2 to 8 carbon atoms, inclusive, which can be straight chain or branched; or
  (e) $R_a Q_2 R_b$
  wherein $Q_2$ is —O— or —S—;
  wherein $R_a$ is alkylene of 0 to 6 carbons atoms, inclusive, which can be straight chain or branched; and wherein $R_b$ is alkyl of 0 to 8 carbon atoms, inclusive, which can be straight chain or branched;
wherein $Y_1$ is —OH, methyl, or —SH;
wherein $Y_2$ is
  (a) a hydrogen atom;
  (b) $CH_a Z_b$
where a+b=3, a=0 to 3, b=0 to 3
wherein each Z, independently, is a cyano, a nitro, or a halogen atom; or
  (c) an alkyl of 2 to 4 carbon atoms, inclusive, straight chain or branched;
wherein $Y_3$ and $Y_5$ are each independently:
  (a) a hydrogen atom;
  (b) $CH_a Z_b$ wherein a+b=3, a=0 to 3, b=0 to 3 and wherein each Z, independently, is a cyano, a nitro, or a halogen atom; or (c) an alkyl of 2 to 4 carbon atoms, inclusive, straight chain or branched;

wherein $Y_4$ and $Y_6$ are each, independently (a) a hydrogen atom;

(b) an alkyl of 2 to 4 carbon atoms, inclusive, straight chain or branched;

(c) an alkoxy of 1 to 4 carbon atoms, inclusive, straight chain or branched; or (d) a hydroxyl or thiol; and wherein $R_5$ is (a) an alkyl of 1 to 9 carbon atoms which can be straight chain or branched;

(b) —$(CH_2)_n$—$R_i$ wherein n=0 to 3 and $R_i$ is (i) a cycloalkyl of 3 to 10 carbon atoms, inclusive;

(ii) phenyl;

(iii) substituted phenyl

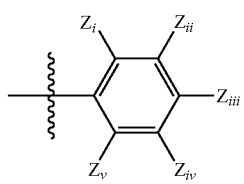

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which can be a straight chain or branched, and hydroxyl;

(c) $R_aQ_aR_b$ wherein $Q_a$ is —O— or —S—;

wherein $R_a$ is alkylene of 0 to 6 carbons atoms, inclusive, which can be straight chain or branched;

wherein $R_b$ is (a) a substituted phenyl

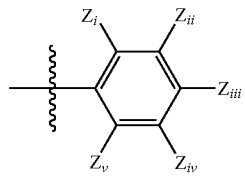

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which can be a straight chain or branched, and hydroxyl;

(b) a substituted phenoxy

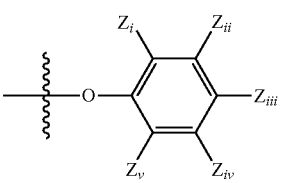

wherein $Z_i$ through $Z_v$ are as defined above; or

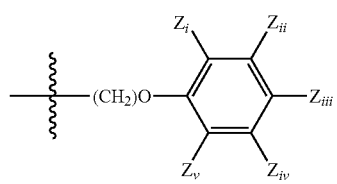

wherein $Z_i$ through $Z_v$ are as defined above;

(d) a haloalkyl of 1 to 8 carbon atoms, inclusive, and 1 to 6 halogen atoms, inclusive, straight chain or branched.

In certain embodiments of this invention, the compounds of this invention have the following structural formulas:

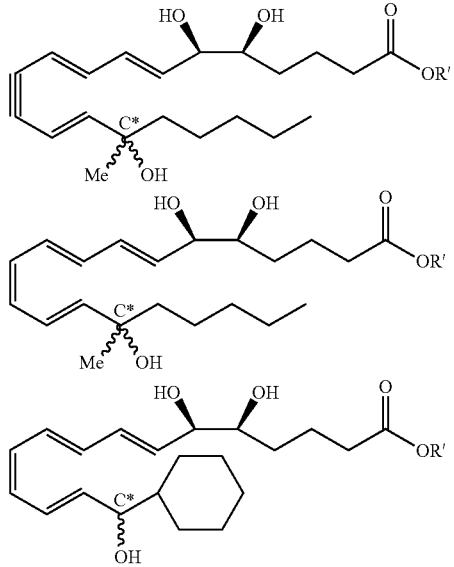

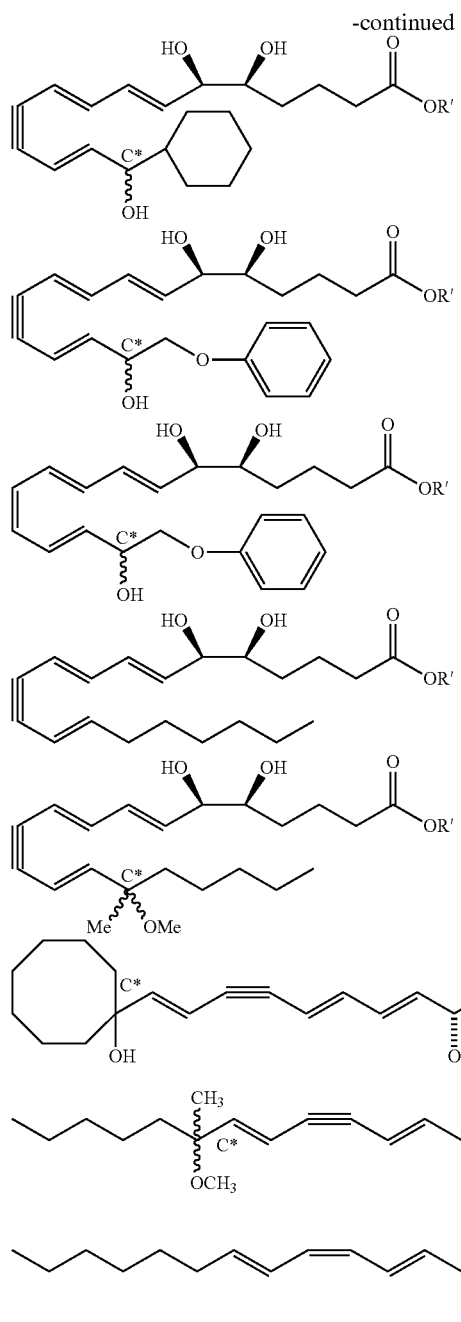
where R' is H or CH$_3$; and where the substituents at C* are in the R configuration.
In other preferred embodiments of this invention, the compounds of this invention have the following structural formulas:
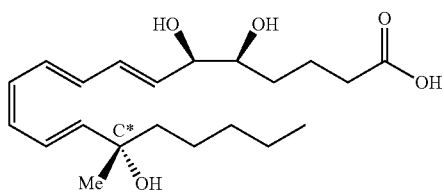
-continued
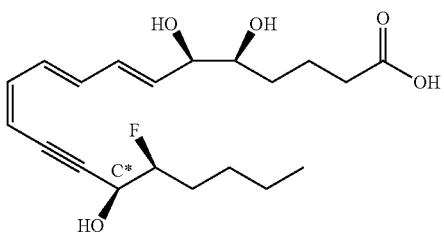

-continued

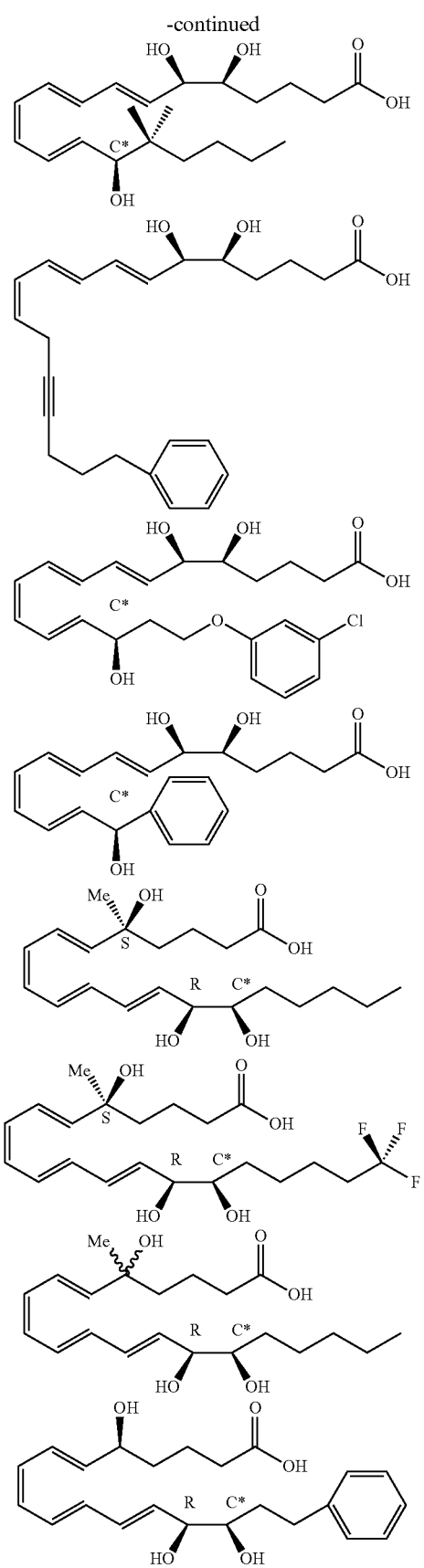

where the substituents at the C* are in the R configuration.

It is to be understood that the carboxylic acids and esters of the invention can be converted, if necessary, into pharmaceutically acceptable salts.

In certain embodiments of the invention, $LXB_4$ or the C5 and C14 and C15 alkanoates (acetates) of $LXB_4$ may be excluded.

Lipoxins Having Phenoxy or Thiophenoxy Substituents

In another aspect, lipoxins and lipoxin analogs useful as therapeutic agents in the treatment of the maladies, disease states or conditions described throughout the specification has the formula:

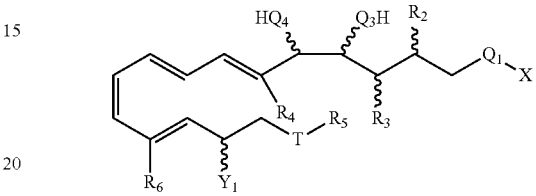

wherein X is $R_1$, $OR_1$, or $SR_1$;
wherein $R_1$ is
(i) a hydrogen atom;
(ii) an alkyl of 1 to 8 carbon atoms, inclusive, which may be straight chain or branched;
(iii) a cycloalkyl of 3 to 10 carbon atoms;
(iv) an aralkyl of 7 to 12 carbon atoms;
(v) phenyl;
(vi) substituted phenyl

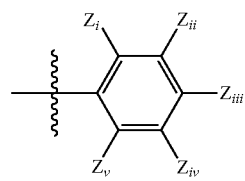

wherein $Z_i$, $Z_{ii}$, $Z_{iii}$, $Z_{iv}$ and $Z_v$ are each independently selected from $-NO_2$, $-CN$, $-C(=O)-R_1$, $-SO_3H$, a hydrogen atom, halogen, methyl, $-OR_x$, wherein $R_x$ is 1 to 8 carbon atoms, inclusive, which may be a straight chain or branched, and hydroxyl;
(vii) a detectable label molecule; or
(viii) a straight or branched chain alkenyl of 2 to 8 carbon atoms, inclusive;
wherein $Q_1$ is $(C=O)$, $SO_2$ or $(CN)$, provided when $Q_1$ is CN, then X is absent;
wherein $Q_3$ and $Q_4$ are each independently O, S or NH;
wherein one of $R_2$ and $R_3$ is a hydrogen atom and the other is
(a) H;
(b) an alkyl of 1 to 8 carbon atoms, inclusive, which may be a straight chain or branched;
(c) a cycloalkyl of 3 to 6 carbon atoms, inclusive;
(d) an alkenyl of 2 to 8 carbon atoms, inclusive, which may be straight chain or branched; or
(e) $R_aQ_2R_b$, wherein $Q_2$ is $-O-$ or $-S-$; wherein $R_a$ is alkylene of 0 to 6 carbon atoms, inclusive, which may be straight chain or branched and wherein $R_b$ is alkyl of 0 to 8 carbon atoms, inclusive, which may be straight chain or branched, provided when $R_b$ is 0, then $R_b$ is a hydrogen atom;

wherein R$_4$ is
(a) H;
(b) an alkyl of 1 to 6 carbon atoms, inclusive, which may be a straight chain or branched;
wherein R$_5$ is

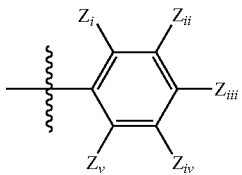

wherein Z$_i$, Z$_{ii}$, Z$_{iii}$, Z$_{iv}$ and Z$_v$ are each independently selected from —NO$_2$, —CN, —C(=O)—R$_1$, —SO$_3$H, a hydrogen atom, halogen, methyl, —OR$_x$, wherein R$_x$ is 1 to 8 carbon atoms, inclusive, which may be a straight chain or branched, and hydroxyl or a substituted or unsubstituted, branched or unbranched alkyl group;
wherein Y$_1$ is —OH, methyl, —SH, an alkyl of 2 to 4 carbon atoms, inclusive, straight chain or branched, an alkoxy of 1 to 4 carbon atoms, inclusive, or CH$_a$Z$_b$ where a+b=3, a=0 to 3, b=0 to 3 and Z is cyano, nitro or a halogen;
wherein R$_6$ is
(a) H;
(b) an alkyl from 1 to 4 carbon atoms, inclusive, straight chain or branched;
wherein T is O or S, and pharmaceutically acceptable salts thereof.

In yet another aspect, lipoxins and lipoxin analogs useful as therapeutic agents in the treatment of the maladies, disease states or conditions described throughout the specification has the formula:

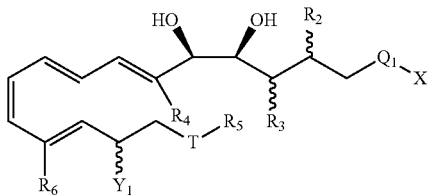

wherein X is R$_1$, OR$_1$, or SR$_1$;
wherein R$_1$ is
(i) a hydrogen atom;
(ii) an alkyl of 1 to 8 carbon atoms, inclusive, which may be straight chain or branched;
(iii) a cycloalkyl of 3 to 10 carbon atoms;
(iv) an aralkyl of 7 to 12 carbon atoms;
(v) phenyl;
(vi) substituted phenyl

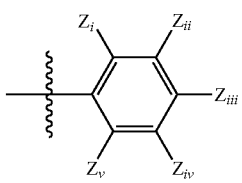

wherein Z$_i$, Z$_{ii}$, Z$_{iii}$, Z$_{iv}$ and Z$_v$ are each independently selected from —NO$_2$, —CN, —C(=O)—R$_1$, —SO$_3$H, a hydrogen atom, halogen, methyl, —OR$_x$, wherein R$_x$ is 1 to 8 carbon atoms, inclusive, which may be a straight chain or branched, and hydroxyl;

(vii) a detectable label molecule; or
(viii) a straight or branched chain alkenyl of 2 to 8 carbon atoms, inclusive;
wherein Q$_1$ is (C=O), SO$_2$ or (CN), provided when Q$_1$ is CN, then X is absent;
wherein one of R$_2$ and R$_3$ is a hydrogen atom and the other is
(a) H;
(b) an alkyl of 1 to 8 carbon atoms, inclusive, which may be a straight chain or branched;
(c) a cycloalkyl of 3 to 6 carbon atoms, inclusive;
(d) an alkenyl of 2 to 8 carbon atoms, inclusive, which may be straight chain or branched; or
(e) R$_a$Q$_2$R$_b$, wherein Q$_2$ is —O— or —S—; wherein R$_a$ is alkylene of 0 to 6 carbon atoms, inclusive, which may be straight chain or branched and wherein R$_b$ is alkyl of 0 to 8 carbon atoms, inclusive, which may be straight chain or branched, provided when R$_b$ is 0, then R$_b$ is a hydrogen atom;
wherein R$_4$ is
(a) H;
(b) an alkyl of 1 to 6 carbon atoms, inclusive, which may be a straight chain or branched;
wherein R$_5$ is

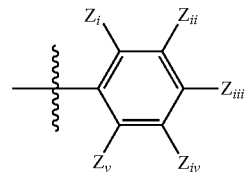

wherein Z$_i$, Z$_{ii}$, Z$_{iii}$, Z$_{iv}$ and Z$_v$ are each independently selected from —NO$_2$, —CN, —C(=O)—R$_1$, —SO$_3$H, a hydrogen atom, halogen, methyl, —OR$_x$, wherein R$_x$ is 1 to 8 carbon atoms, inclusive, which may be a straight chain or branched, and hydroxyl or a substituted or unsubstituted, branched or unbranched alkyl group;
wherein Y$_1$ is —OH, methyl, —SH, an alkyl of 2 to 4 carbon atoms, inclusive, straight chain or branched, an alkoxy of 1 to 4 carbon atoms, inclusive, or CH$_a$Z$_b$ where a+b=3, a=0 to 3, b=0 to 3 and Z is cyano, nitro or a halogen;
wherein R$_6$ is
(a) H;
(b) an alkyl from 1 to 4 carbon atoms, inclusive, straight chain or branched;
wherein T is O or S, and pharmaceutically acceptable salts thereof.

In still another aspect, lipoxins and lipoxin analogs useful as therapeutic agents in the treatment of the maladies, disease states or conditions described throughout the specification has the formula:

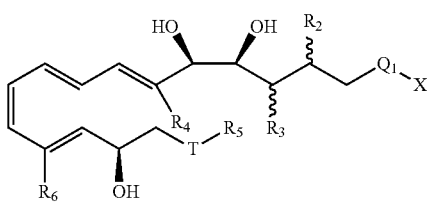

wherein X is $R_1$, $OR_1$, or $SR_1$;

wherein $R_1$ is (i) a hydrogen atom;

(ii) an alkyl of 1 to 8 carbon atoms, inclusive, which may be straight chain or branched;

(iii) a cycloalkyl of 3 to 10 carbon atoms;

(iv) an aralkyl of 7 to 12 carbon atoms;

(v) phenyl;

(vi) substituted phenyl

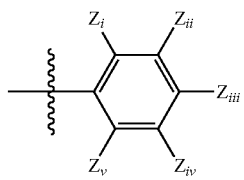

wherein $Z_i$, $Z_{ii}$, $Z_{iii}$, $Z_{iv}$ and $Z_v$ are each independently selected from $-NO_2$, $-CN$, $-C(=O)-R_1$, $-SO_3H$, a hydrogen atom, halogen, methyl, $-OR_x$, wherein $R_x$ is 1 to 8 carbon atoms, inclusive, which may be a straight chain or branched, and hydroxyl;

(vii) a detectable label molecule; or (viii) a straight or branched chain alkenyl of 2 to 8 carbon atoms, inclusive;

wherein $Q_1$ is (C=O), $SO_2$ or (CN), provided when $Q_1$ is CN, then X is absent;

wherein one of $R_2$ and $R_3$ is a hydrogen atom and the other is (a) H;

(b) an alkyl of 1 to 8 carbon atoms, inclusive, which may be a straight chain or branched;

(c) a cycloalkyl of 3 to 6 carbon atoms, inclusive;

(d) an alkenyl of 2 to 8 carbon atoms, inclusive, which may be straight chain or branched; or (e) $R_aQ_2R_b$ wherein $Q_2$ is $-O-$ or $-S-$; wherein $R_a$ is alkylene of 0 to 6 carbon atoms, inclusive, which may be straight chain or branched and wherein $R_b$ is alkyl of 0 to 8 carbon atoms, inclusive, which may be straight chain or branched, provided when $R_b$ is 0, then $R_b$ is a hydrogen atom;

wherein $R_4$ is (a) H;

(b) an alkyl of 1 to 6 carbon atoms, inclusive, which may be a straight chain or branched;

wherein $R_5$ is

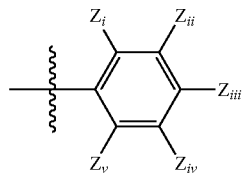

wherein $Z_i$, $Z_{ii}$, $Z_{iii}$, $Z_{iv}$ and $Z_v$ are each independently selected from $-NO_2$, $-CN$, $-C(=O)-R_1$, $-SO_3H$, a hydrogen atom, halogen, methyl, $-OR_x$, wherein $R_x$ is 1 to 8 carbon atoms, inclusive, which may be a straight chain or branched, and hydroxyl or a substituted or unsubstituted, branched or unbranched alkyl group;

wherein $R_6$ is (a) H;

(b) an alkyl from 1 to 4 carbon atoms, inclusive, straight chain or branched;

wherein T is O or S, and pharmaceutically acceptable salts thereof.

In yet another aspect, lipoxins and lipoxin analogs useful as therapeutic agents in the treatment of the maladies, disease states or conditions described throughout the specification has the formula:

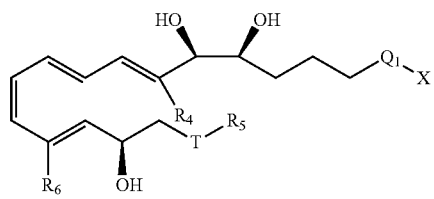

wherein X is $R_1$, $OR_1$, or $SR_1$;

wherein $R_1$ is (i) a hydrogen atom;

(ii) an alkyl of 1 to 8 carbon atoms, inclusive, which may be straight chain or branched;

(iii) a cycloalkyl of 3 to 10 carbon atoms;

(iv) an aralkyl of 7 to 12 carbon atoms;

(v) phenyl;

(vi) substituted phenyl

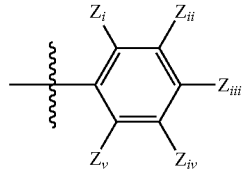

wherein $Z_i$, $Z_{ii}$, $Z_{iii}$, $Z_{iv}$ and $Z_v$ are each independently selected from $-NO_2$, $-CN$, $-C(=O)-R_1$, $-SO_3H$, a hydrogen atom, halogen, methyl, $-OR_x$, wherein $R_x$ is 1 to 8 carbon atoms, inclusive, which may be a straight chain or branched, and hydroxyl;

(vii) a detectable label molecule; or (viii) a straight or branched chain alkenyl of 2 to 8 carbon atoms, inclusive;

wherein $Q_1$ is (C=O), $SO_2$ or (CN), provided when $Q_1$ is CN, then X is absent;

wherein $R_4$ is
(a) H;
(b) an alkyl of 1 to 6 carbon atoms, inclusive, which may be a straight chain or branched;
wherein $R_5$ is

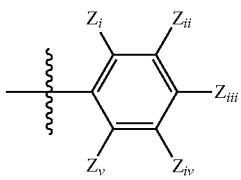

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which may be a straight chain or branched, and hydroxyl or a substituted or unsubstituted, branched or unbranched alkyl group;
wherein $R_6$ is
(a) H;
(b) an alkyl from 1 to 4 carbon atoms, inclusive, straight chain or branched;
wherein T is O or S, and pharmaceutically acceptable salts thereof.

In one aspect, lipoxins and lipoxin analogs useful as therapeutic agents in the treatment of the maladies, disease states or conditions described throughout the specification has the formula:

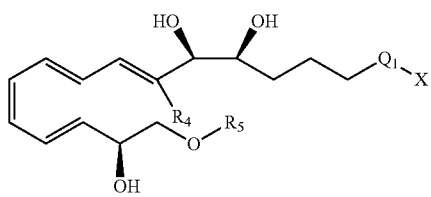

wherein X is $R_1$, $OR_1$, or $SR_1$;
wherein $R_1$ is
(i) a hydrogen atom;
(ii) an alkyl of 1 to 8 carbon atoms, inclusive, which may be straight chain or branched;
(iii) a cycloalkyl of 3 to 10 carbon atoms;
(iv) an aralkyl of 7 to 12 carbon atoms;
(v) phenyl;
(vi) substituted phenyl

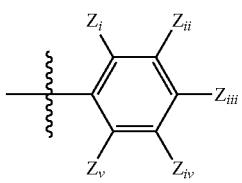

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which may be a straight chain or branched, and hydroxyl;

(vii) a detectable label molecule; or
(viii) a straight or branched chain alkenyl of 2 to 8 carbon atoms, inclusive;
wherein $R_4$ is
(a) H;
(b) an alkyl of 1 to 6 carbon atoms, inclusive, which may be a straight chain or branched;
wherein $R_5$ is

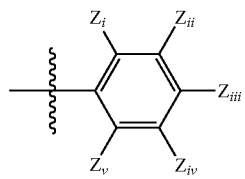

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which may be a straight chain or branched, and hydroxyl or a substituted or unsubstituted, branched or unbranched alkyl group; and pharmaceutically acceptable salts thereof.

In preferred embodiments, X is $OR_1$ wherein $R_1$ is a hydrogen atom, an alkyl group of 1 to 4 carbon atoms or a pharmaceutically acceptable salt, $Q_1$ is C=O, $R_2$ and $R_3$, if present, are hydrogen atoms, $R_4$ is a hydrogen atom or methyl, Q3 and $Q_4$, if present, are both O, $R_6$, if present, is a hydrogen atom, $Y_1$, if present, is OH, T is O and $R_5$ is a substituted phenyl, e.g.,

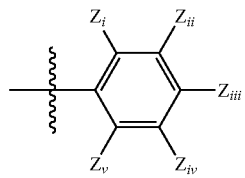

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which may be a straight chain or branched, and hydroxyl. In certain embodiments for $R_5$, para-fluorophenyl and/or unsubstituted phenyl are preferred, e.g., 15-epi-16-(para-fluoro)-phenoxy-$LXA_4$, 16-(para-fluoro)-phenoxy-$LXA_4$, 15-epi-16-phenoxy-$LXA_4$ or 16-phenoxy-$LXA_4$.

In still another aspect, the present invention is directed to pharmaceutical compositions including compounds having the formulae described throughout the specification and a pharmaceutically acceptable carrier. In one embodiment, a preferred compound is

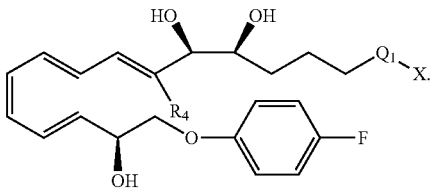

In one embodiment, $Q_1$ is a carbonyl, X is a hydroxyl or an —OR, wherein R is an alkyl group, i.e., methyl or ethyl groups, and $R_4$ is a hydrogen atom.

In other embodiments, $Y_1$ is a hydroxyl and the carbon bearing the hydroxyl can have an R or S configuration. In most preferred embodiments, the chiral carbon bearing the hydroxyl group, e.g., $Y_1$, is designated as a 15-epi-lipoxin as is known in the art.

In certain embodiments the chirality of the carbons bearing the $R_2$, $R_3$, $Q_3$ and $Q_4$ groups can each independently be either R or S. In preferred embodiments, $Q_3$ and $Q_4$ have the chiralities shown in above-referenced structures.

In preferred embodiments, $R_4$ is a hydrogen. In other preferred embodiments, $R_6$ is a hydrogen.

Additionally, $R_5$ can be a substituted or unsubstituted, branched or unbranched alkyl group having between 1 and about 6 carbon atoms, preferably between 1 and 4 carbon atoms, most preferably between 1 and 3, and preferably one or two carbon atoms. The carbon atoms can have substituents which include halogen atoms, hydroxyl groups, or ether groups.

The compounds useful in the present invention can be prepared by the following synthetic scheme:

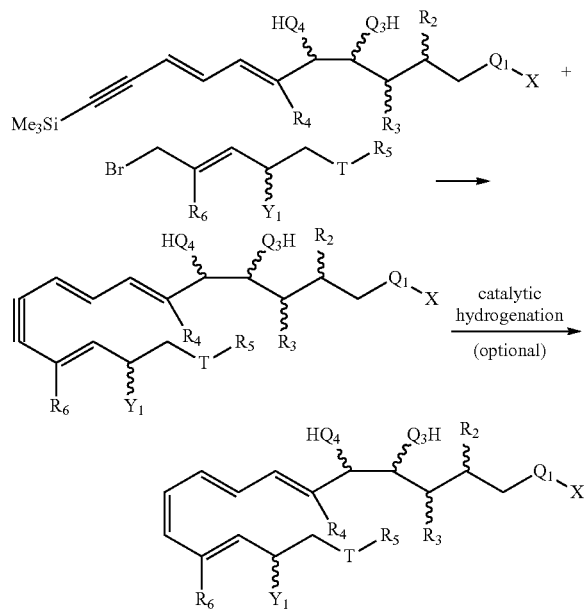

wherein X, $Q_1$, $Q_3$, $Q_4$, $R_2$, $R_3$, $R_4$, $R_5$, $R_6$, $Y_1$ and T are as defined above.

Suitable methods known in the art to can be used to produce each fragment. For example, the acetylenic fragment can be prepared by the methods discussed in Nicolaou, K. C. et al. (1991) Angew. Chem. Int. Ed. Engl. 30:1100; Nicolaou, K. C. et al. (1989) J. Org. Chem. 54:5527; Webber, S. E. et al. (1988) Adv. Exp. Med. Biol. 229:61; and U.S. Pat. No. 5,441,951. The second fragment can be prepared by the methods of Raduchel, B. and Vorbruggen, H. (1985) Adv. Prostaglandin Thromboxane Leukotriene Res. 14:263. As a consequence, the acetylenic intermediates are also encompassed by the present invention as being useful for the treatments of the various maladies described herein. Similar approaches can be taken to produce $LXB_4$ acetylenic compounds as described in, for example, U.S. Pat. No. 6,316,648.

A "lipoxin analog" shall mean a compound which has an "active region" that functions like the active region of a "natural lipoxin", but which has a "metabolic transformation region" that differs from natural lipoxin. Lipoxin analogs include compounds which are structurally similar to a natural lipoxin, compounds which share the same receptor recognition site, compounds which share the same or similar lipoxin metabolic transformation region as lipoxin, and compounds which are art-recognized as being analogs of lipoxin. Lipoxin analogs include lipoxin analog metabolites. The compounds disclosed herein may contain one or more centers of asymmetry. Where asymmetric carbon atoms are present, more than one stereoisomer is possible, and all possible isomeric forms are intended to be included within the structural representations shown. Optically active (R) and (S) isomers may be resolved using conventional techniques known to the ordinarily skilled artisan. The present invention is intended to include the possible diastereiomers as well as the racemic and optically resolved isomers.

The terms "corresponding lipoxin" and "natural lipoxin" refer to a naturally-occurring lipoxin or lipoxin metabolite. Where an analog has activity for a lipoxin-specific receptor, the corresponding or natural lipoxin is the normal ligand for that receptor. For example, where an analog is a $LXA_4$ specific receptor on differentiated HL-60 cells, the corresponding lipoxin is $LXA_4$. Where an analog has activity as an antagonist to another compound (such as leukotriene C4 and/or leukotriene D4), which is antagonized by a naturally-occurring lipoxin, that natural lipoxin is the corresponding lipoxin.

"Active region" shall mean the region of a natural lipoxin or lipoxin analog, which is associated with in vivo cellular interactions. The active region may bind the "recognition site" of a cellular lipoxin receptor or a macromolecule or complex of macromolecules, including an enzyme and its cofactor. For example, lipoxin $A_4$ analogs have an active region comprising $C_5$-$C_{15}$ of natural lipoxin $A_4$. Similarly, for example, lipoxin $B_4$ analogs have an active region comprising C5-C14 of natural lipoxin $B_4$.

The term "recognition site" or receptor is art-recognized and is intended to refer generally to a functional macromolecule or complex of macromolecules with which certain groups of cellular messengers, such as hormones, leukotrienes, lipoxins, must first interact before the biochemical and physiological responses to those messengers are initiated. As used in this application, a receptor may be isolated, on an intact or permeabilized cell, or in tissue, including an organ. A receptor may be from or in a living subject, or it may be cloned. A receptor may normally exist or it may be induced by a disease state, by an injury, or by artificial means. A compound of this invention may bind reversibly, irreversibly, competitively, noncompetitively, or uncompetitively with respect to the natural substrate of a recognition site.

The term "metabolic transformation region" is intended to refer generally to that portion of a lipoxin, a lipoxin metabolite, or lipoxin analog including a lipoxin analog metabolite, upon which an enzyme or an enzyme and its cofactor attempts to perform one or more metabolic transformations which that enzyme or enzyme and cofactor normally transform on lipoxins. The metabolic transformation region may or may not be susceptible to the transformation. Similarly, such regions are possibly located within ATL and $LXB_4$ analogs. A nonlimiting example of a metabolic transformation region of a lipoxin is a portion of $LXA_4$ that includes the C-13,14 double bond or the C-15 hydroxyl group, or both.

The term "detectable label molecule" is meant to include fluorescent, phosphorescent, and radiolabeled molecules used to trace, track, or identify the compound or receptor recognition site to which the detectable label molecule is bound. The label molecule may be detected by any of the several methods known in the art.

The term "labeled analog" is further understood to encompass compounds which are labeled with radioactive isotopes, such as but not limited to tritium ($^3$H), deuterium ($^2$H), carbon $^{14}$C) or otherwise labeled (e.g. fluorescently). The compounds of this invention may be labeled or derivatized, for example, for kinetic binding experiments, for further elucidating metabolic pathways and enzymatic mechanisms, or for characterization by methods known in the art of analytical chemistry.

The term "inhibits metabolism" means the blocking or reduction of activity of an enzyme which metabolizes a native eicosanoid. The blockage or reduction may occur by covalent bonding, by irreversible binding, by reversible binding which has a practical effect of irreversible binding, or by any other means which prevents the enzyme from operating in its usual manner on another lipoxin analog, including a lipoxin analog metabolite, a lipoxin, or a lipoxin metabolite. Similarly, this also applies to ATL and $LXB_4$ analogs.

The term "resists metabolism" is meant to include failing to undergo one or more of the metabolic degradative transformations by at least one of the enzymes which metabolize lipoxins, ATL or $LXB_4$ analogs. Two nonlimiting examples of $LXA_4$ analog that resists metabolism are 1) a structure which cannot be oxidized to the 15-oxo form, and 2) a structure which may be oxidized to the 15-oxo form, but is not susceptible to enzymatic reduction to the 13,14-dihydro form.

The term "more slowly undergoes metabolism" means having slower reaction kinetics, or requiring more time for the completion of the series of metabolic transformations by one or more of the enzymes which metabolize lipoxin, lipoxin analogs, ATL or $LXB_4$ analogs. A nonlimiting example of a $LXA_4$ analog which more slowly undergoes metabolism is a structure which has a higher transition state energy for C-15 dehydrogenation than does $LXA_4$ because the analog is sterically hindered at the C-16.

The term "tissue" is intended to include intact cells, blood, blood preparations such as plasma and serum, bones, joints, muscles, smooth muscles, and organs.

The term "halogen" is meant to include fluorine, chlorine, bromine and iodine, or fluoro, chloro, bromo, and iodo.

The invention is further illustrated by the following examples which in no way should be construed as being further limiting. The contents of all references, pending patent applications and published patent applications, cited throughout this application, including those referenced in the background section, are hereby incorporated by reference. It should be understood that the models used throughout the examples are accepted models and that the demonstration of efficacy in these models is predictive of efficacy in humans.

The term "subject" is intended to include living organisms susceptible to conditions or diseases caused or contributed bacteria, pathogens, disease states or conditions as generally disclosed, but not limited to, throughout this specification. Examples of subjects include humans, dogs, cats, cows, goats, and mice. The term subject is further intended to include transgenic species.

When the compounds of the present invention are administered as pharmaceuticals, to humans and mammals, they can be given per se or as a pharmaceutical composition containing, for example, 0.1 to 99.5% (more preferably, 0.5 to 90%) of active ingredient, i.e., at least one lipoxin, in combination with a pharmaceutically acceptable carrier.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting a compound(s) of the present invention within or to the subject such that it can perform its intended function. Typically, such compounds are carried or transported from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

In certain embodiments, the compounds of the present invention may contain one or more acidic functional groups and, thus, are capable of forming pharmaceutically acceptable salts with pharmaceutically acceptable bases. The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. These may include cations based on the alkali and alkaline earth metals, such as sodium, lithium, potassium, calcium, magnesium and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See, for example, Berge S. M., et al., "Pharmaceutical Salts," J. Pharm. Sci., 1977; 66:1-19 which is incorporated herein by reference).

The term "pharmaceutically acceptable esters" refers to the relatively non-toxic, esterified products of the compounds of the present invention. These esters can be prepared in situ during the final isolation and purification of the compounds, or by separately reacting the purified compound in its free acid form or hydroxyl with a suitable esterifying agent. Carboxylic acids can be converted into esters via treatment with an alcohol in the presence of a catalyst. The term is further intended to include lower hydrocarbon groups capable of being solvated under physiological conditions, e.g., alkyl esters, methyl, ethyl and propyl esters.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations of the present invention include those suitable for intravenous, oral, nasal, topical, transdermal, buccal, sublingual, rectal, vaginal and/or parenteral administration. The formulations may conveniently be presented in unit dosage form and may be prepared by any methods well known in the art of pharmacy. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention. Such solutions are useful for the treatment of the conditions described herein, such as NV, hemangiogenesis or angiogenesis of the corneal tissue.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

The preparations of the present invention may be given orally, parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Intravenous injection administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systematically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of ordinary skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous and subcutaneous doses of the compounds of this invention for a patient, when used for the indicated analgesic effects, will range from about 0.0001 to about 100 mg per kilogram of body weight per day, more preferably from about 0.01 to about 50 mg per kg per day, and still more preferably from about 0.1 to about 40 mg per kg per day. For example, between about 0.01 microgram and 20 micrograms, between about 20 micrograms and 100 micrograms and between about 10 micrograms and 200 micrograms of the compounds of the invention are administered per 20 grams of subject weight.

If desired, the effective daily dose of the active compound may be administered as two, three, four, five, six or more sub-doses administered separately at appropriate intervals throughout the day, optionally, in unit dosage forms.

The pharmaceutical compositions of the invention include a "therapeutically effective amount" or a "prophylactically effective amount" of one or more of the lipoxins of the invention. A "therapeutically effective amount" refers to an amount effective, at dosages and for periods of time necessary, to achieve the desired therapeutic result, e.g., a diminishment or prevention of effects associated with various disease states or conditions. A therapeutically effective amount of the lipoxin may vary according to factors such as the disease state, age, sex, and weight of the individual, and the ability of the therapeutic compound to elicit a desired response in the individual. A therapeutically effective amount is also one in which any toxic or detrimental effects of the therapeutic agent are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the lipoxin and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of a lipoxin of the invention is 0.1-20 mg/kg, more preferably 1-10 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

While it is possible for a compound of the present invention to be administered alone, it is preferable to administer the compound as a pharmaceutical composition.

The invention features an article of manufacture that contains packaging material and a lipoxin analog formulation contained within the packaging material. This formulation contains an at least one lipoxin and the packaging material contains a label or package insert indicating that the formulation can be administered to the subject to treat one or more conditions as described herein, in an amount, at a frequency, and for a duration effective to treat or prevent such condition(s). Such conditions are mentioned throughout the specification and are incorporated herein by reference. Suitable lipoxins are described herein.

More specifically, the invention features an article of manufacture that contains packaging material and at least one lipoxin contained within the packaging material. The packaging material contains a label or package insert indicating that the formulation can be administered to the subject to asthma in an amount, at a frequency, and for a duration effective treat or prevent symptoms associated with such disease states or conditions discussed throughout this specification.

Materials and Methods

Cell Culture

Human umbilical vein endothelial cells (HUVEC) were isolated by 0.1% collagenase digestion (Worthington Biochemical, Bedford, Mass.) and propagated on gelatin-coated (0.1%) tissue culture plates in medium 199 (Gibco BRL, Grand Island, N.Y.) supplemented with 20% heat-inactivated fetal bovine serum (BioWhittaker, Walkersville, Md.), 50 μg/ml of endothelial cell mitogen (Biomedical Technologies, Stoughton, Mass.), 8 U/ml heparin (APP, Los Angeles, Calif.), 50 U/ml penicillin and 15 μg/ml streptomycin. Only passages 2 and 3 were used in reported experiments.

Endothelial Cell Proliferation

HUVEC ($5 \times 10^3$) were plated in 96-well plates coated with 0.1% gelatin for 1 h at room temperature. After 24 h, the medium was removed and replaced with fresh medium 199 supplemented with 5% fetal bovine serum and different concentrations of recombinant human $VEGF_{165}$ (R&D Systems, Minneapolis, Minn.), $LTD_4$ or $LTB_4$. Endothelial cells were enumerated after 72 h using the MTT® assay (Sigma, St. Louis, Mo.) (15). ATL-1 was prepared as in Clish et al. (13). Percent inhibition was evaluated in a similar manner and included a 15 minute incubation (37° C.) with 15-epi-lipoxin $A_4$, 15-epi-16-(para-fluoro)-phenoxy-lipoxin $A_4$ methyl ester (ATL-1), $LXA_4$, 15-epi-$LXA_4$ or 15-R/S-methyl, $LXA_4$ prior to the addition of agonists. All incubations were performed in triplicate. Before each experiment the integrity and concentration of ATL-1, LXA$_4$, 15-epi-LXA$_4$ or 15-R/S-methyl, LXA$_4$ was assessed by physical methods including LC/MS/MS and UV (13).

Endothelial Cell Migration

VEGF, ATL-1 or vehicle were added to the lower wells of a 48-well chemotaxis chamber (NeuroProbe, Cabin John, Md.). The wells were overlaid with a 10 μm pore size polycarbonate filter coated with 0.1% gelatin. HUVEC (1×10$^6$) were placed in the upper wells and the chamber was incubated (37° C., 5% CO$_2$ for 12 h). Following incubations, filters were removed, scraped of cells from the upper surface, fixed and stained with Diff-Quik (Dade Behring, Newark, Del.). Cells that migrated across the filter toward the lower surface were enumerated by light microscopy; four fields were counted at high magnification (100×). Incubations were performed in triplicate. To assess inhibition, endothelial cells were suspended in media with vehicle or ATL-1 for 15 min before placement in the chamber.

Quantitative Determination of DNA Fragmentation

DNA fragmentation in individual apoptotic cells was quantitated using a photometric enzyme immunoassay (Apotosis detection kit: R&D Systems). HUVECs grown in 96-well microtiter plates (5×10$^3$ cells/well) were incubated for 3 days, fixed with 3.7% formaldehyde, and permeabilized with proteinase K before the labeling. Biotinylated nucleotides are incorporated onto the DNA fragments and detected by using steptavidin-horseradish peroxidase conjugate followed by the substrate TACS-Sapphire.

Inflammatory Angiogenesis

Angiogenesis was assessed with murine air pouches that were raised via subcutaneous injection of sterile air (3 ml) beneath the dorsal skin of anesthetized mice (BALB/c, male 6-8 wk). After 24 hrs, ATL-1 (10 μg/pouch) or vehicle was delivered locally, immediately before the injection of VEGF (1 μg/pouch). The vascular content was assessed by the formation of vascular casts (as in 16). Briefly, mice were anesthetized (at 144 h) and peripheral vasodilation was raised by placing the animals in a heated jacket (40° C., 10 min). Vascular casts were formed by the i.v. injection of 1 ml 5% carmine red (Sigma) in 5% gelatin solution warmed to 40° C. Air pouch linings were dissected and weighed. The tissue was then dissolved in 2 ml of 3 N NaOH solution for 0.5 h, 21° C. and completely digested in hot water (56° C.) for 10 min. Digested samples were centrifuged (2500 rpm, 15 min) and filtered through a 0.45 μm filter. The dye content was quantified employing a 96-well plate spectrophotometer at 530 nm using a calibration curve. The results were expressed as vascular index (VI) as micrograms carmine dye/milligram weight of tissue, for n=4 animals/group. For visualization of the vasculature, the dorsal surface of the pouches was excised and fixed in formalin for 48 h. The tissues were dehydrated with 100% ethanol (5 days, 4° C.) and cleared by immersion in cedar wood oil for 2 weeks. In another set of experiments, mice were anesthetized and injected i.v. with 200 μl of 0.05 g/ml fluorescein isothiocyanate-dextran (Sigma) in PBS at 144 h immediately before sacrifice. Dissected linings were fixed, mounted on glass slides and examined for fluorescence (Nikon Eclipse model E600). In both protocols, the observers were not blinded to the treatments.

Immunohistochemistry

Air pouch membranous tissues were fixed in 10% buffered formalin overnight and processed for paraffin embedding. Five-micrometer paraffin sections of membrane tissue cut on face were used for immunohistochemistry for CD31 expression. Briefly, slides were deparaffinized and pretreated in 0.25% trypsin (Sigma Chemical) for 20 min at 37° C., followed by washing in distilled water. All further steps were performed at room temperature in a hydrated chamber. Slides were pretreated with Peroxidase Block (DAKO, Carpinteria, Calif.) for 5 min to quench endogenous peroxidase activity, followed by a 1:5 dilution of goat serum in 50 Mm Tris-Cl, pH 7.4, for 20 min to block nonspecific binding sites. Primary rat anti-murine CD31 antibody (BD PharMingen, San Diego, Calif.) was applied at a 1:100 dilution in 50 mMTris-Cl, pH 7.4, with 3% goat serum for 1 h. After washing in 50 mM Tris-Cl, pH 7.4, secondary rabbit anti-rat antibody (DAKO) was applied at a 1:200 dilution in 50 mM Tris-Cl, pH 7.4, with 3% goat serum for 30 min. Slides were washed again in 50 mM Tris-Cl, pH 7.4, and goat anti-rabbit horseradish peroxidase-conjugated antibody (Envision detection kit: DAKO) was applied for 30 min. After further washing, immunoperoxidase staining was developed using a DAB chromogen kit (DAKO) per the manufacturer and counterstained with hematoxylin.

Statistical Analysis

Results are presented as means±S.E.M. Statistical evaluation of the results was performed by analysis of variance, and values of P<0.05 were taken to represent statistically significant differences between group means.

Results and Discussion

The aspirin-triggered lipoxin A$_4$ stable analog (denoted ATL-1) proved a potent inhibitor of VEGF-stimulated proliferation of HUVECs (IC$_{50}$ of ~3 nM) (FIG. 1) Inhibition was concentration-dependent and maximal plateau at 10 nM and was partially reversed (from 38.0±2.5 to 78.0±6.21% of VEGF-stimulated proliferation, P<0.05) by incubating the cells with genistein, an inhibitor of tyrosine kinase activity (50 μM, 5 min, 37° C., n=3). Even at high concentrations (100 nM), the ATL-1 analog alone had no apparent actions on HUVEC proliferation (FIG. 1 inset). In sharp contrast, LXB$_4$ stable analogs increased proliferation. Because these are related structures, the separate actions of ATL and LXB$_4$ analogs with these cells indicate that the ATL-1 response is highly stereoselective. Also, a direct comparison of ATL-1 with native LXA$_4$ and 15-epi-LXA$_4$ at equimolar concentrations (10 nM) in a representative experiment showed that ATL-1>15-epi-LXA$_4$>LXA$_4$ in rank order of activity (e.g., 63.3±3.3, 59.8±1.8 and 38.1±2.0% inhibition, respectively). After exposure of the cells to ATL-1, ~98% of the HUVEC remained viable, as determined by trypan blue exclusion assay, indicating that the compound was not cytotoxic. In addition to being an endothelial cell-specific mitogen, VEGF is also an endothelial cell survival factor, thus promoting angiogenesis not only by stimulating cell proliferation but also by inhibiting endothelial cell apoptosis (17).

To determine whether this new inhibitory action of ATL-1 on HUVEC proliferation involved apoptosis, DNA fragments were quantitated (under Materials and Methods). Neither the ATL-1 (100 nM) alone nor in combination with VEGF (3 ng/ml) affected DNA fragmentation pattern (n=2, d=3), suggesting that the antiproliferative actions of the ATL-1 analog were not a results of induction of apoptosis in endothelial cells. Binding of αv integrins by endothelial cells is accompanied by a decrease in the tumor-suppressor p53 activity and inhibition of apoptotic pathways, thereby facilitating the formation of new blood vessels (18). Along these lines, it was recently shown that p53 can up-regulate human 15-lipoxygenase promoter activity, providing the first link between this enzyme's activity and an established tumor-suppressor gene (19). Also of interest, over-expression of 15-lipoxygenase enhances endogenous LXA$_4$ formation that in turn inhibits progression of glomerulonephritis (20). Both ATL and LXA$_4$ share sites of action that are receptor cell type, and tissue-specific, and together with their stable analogs display potent anti-inflammatory actions (21, 23 and 14).

Figure 2A:
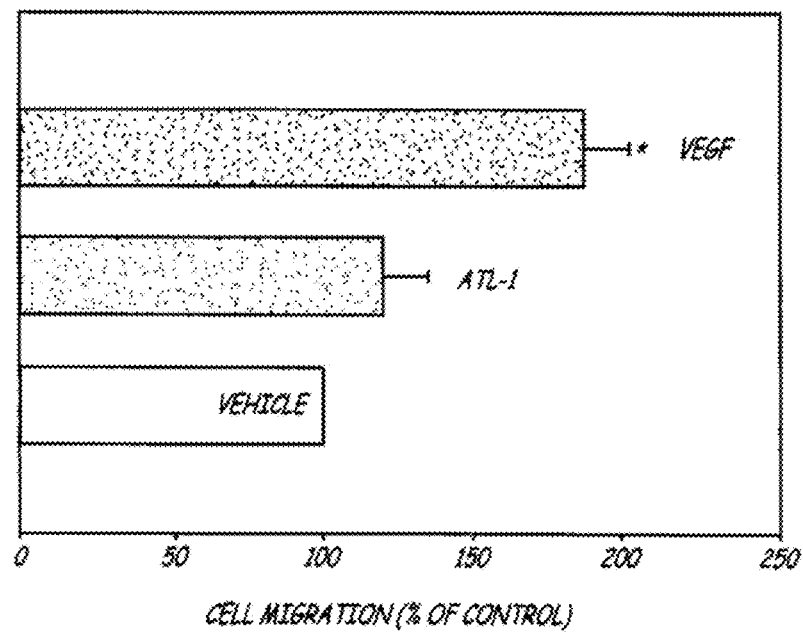
FIGS. 2A-B, demonstrate that ATL-1, as well as $LXA_4$, 15-epi-$LXA_4$ and 15-R/S-methyl, $LXA_4$ each inhibit endothelial cell chemotaxis. 2A, Chemotaxis was initiated by addition of VEGF (3 ng/ml) or ATL-1 (100 nM) to the lower compartment of a 48-well chemotaxis chamber. Results are expressed as percent of cell migration compared to vehicle alone and represent mean±SE for three independent experiments performed in triplicate ($P<0.05$). 2B, HUVEC were incubated with vehicle or indicated concentrations of ATL-1 (15 min, 37° C.) and added to the upper compartment of the microchamber ($1\times10^6$/well). Chemotaxis was initiated by addition of VEGF (3 ng/ml) to the lower compartment. Results are expressed as percent inhibition of migration relative to VEGF for a representative experiment performed in triplicate.
Figure 2B:
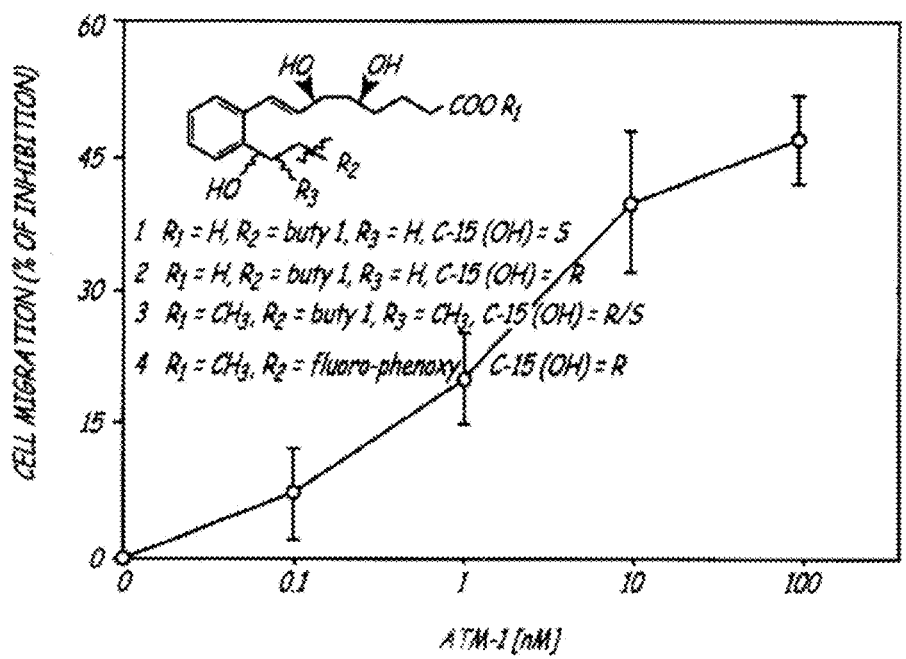

Endothelial cell migration is an essential component of the angiogenic process, providing directionality for the budding capillary toward the angiogenic stimulus (3). Therefore, endothelial migration was assessed with ATL. VEGF (3 ng/ml) was added to the lower compartment of a chemotaxis chamber and cell migration across a 10-µm pore-size gelatin-coated filter was quantitated (FIG. 2). Results in FIG. 2B showed that ATL-1, LXA$_4$, 15-epi-LXA$_4$ and 15-R/S-methyl, LXA$_4$ (ATL-1 shown as representative) gave concentration-dependent inhibition of VEGF-stimulated HUVEC migration with a maximum level of inhibition (~45%) at 10 nM ATL. As observed with proliferation assays, ATL-1, LXA$_4$, 15-epi-LXA$_4$ or 15-R/S-methyl, LXA$_4$ alone, even at higher concentrations (100 nM), did not induce endothelial cell migration (FIG. 2A), findings which suggest that ATL, LXA$_4$, 15-epi-LXA$_4$ or 15-R/S-methyl, LXA$_4$ play a role in blocking the early stages of cell migration to sites of neovascularization.

Figure 3A:
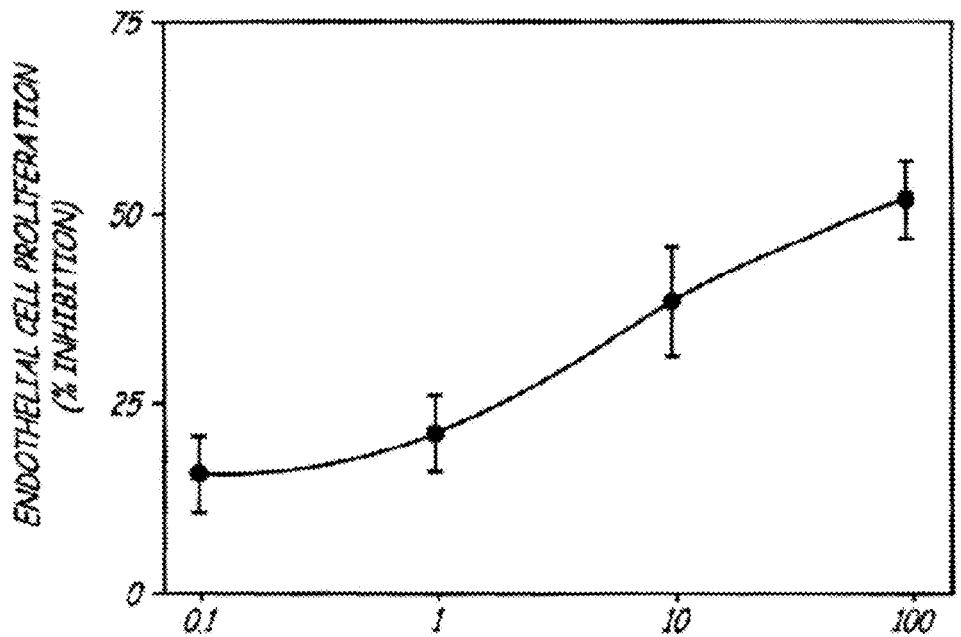
FIGS. 3A-B, are graphical representations demonstrating inhibition of HUVEC proliferation. 3A, ATL-1 inhibits $LTD_4$-stimulated HUVEC proliferation. HUVECs ($5\times10^3$) were plated in 96-well culture plates, cell proliferation was stimulated with 10 nM $LTD_4$, and cell numbers were determined after 3 days using MTT. 3B, concentration dependent cell proliferation induced by $LTD_4$ and $LTB_4$. Results are expressed as mean±S.E. for four independent experiments performed in triplicate.
Figure 3B:
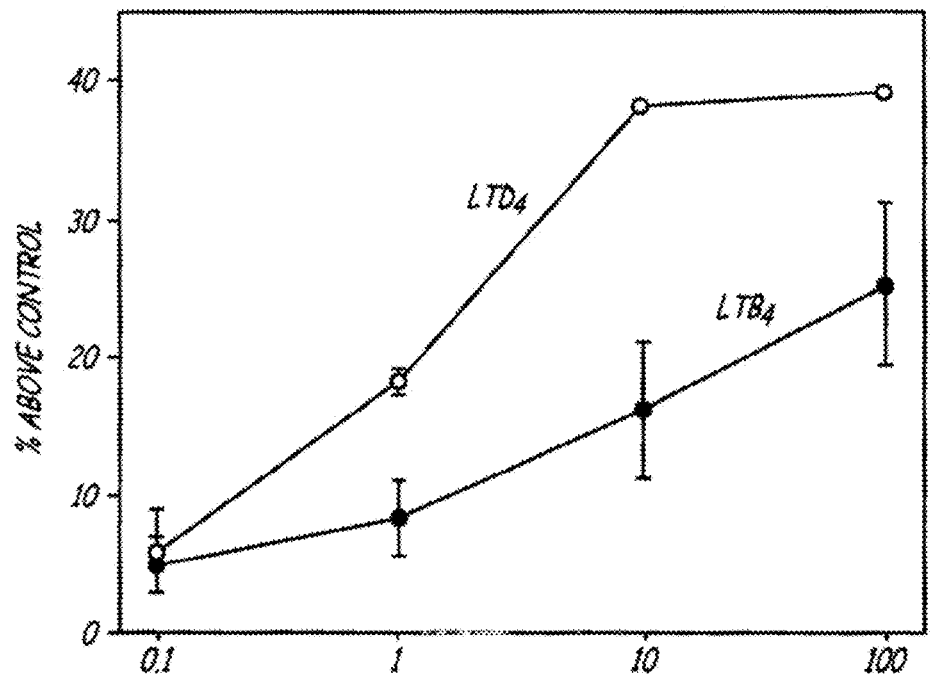

Like VEGF (FIG. 1), LTD$_4$ also stimulated proliferation of HUVEC (42±1.2%) with a maximum at 10 nM, similar to the response obtained with VEGF (52.7±1.6%)). In contrast, LTB$_4$ at 10 nM did not give a significant response with these cells (FIG. 3B). The mitogenic action of LTD$_4$ (10 nM) was antagonized by exposure of the cells to ATL-1 (0.1-100 nM) with an IC$_{50}$ of ~3 nM (FIG. 3A). LTD$_4$ did not enhance or inhibit the VEGF-stimulated proliferation.

The antiproliferative actions of native lipoxins were first found with the human lung adenocarcinoma cell line (23) and recently with human renal mesangial cells (24). The present findings, together with endothelial cell results, draw attention to the potential regulatory role for endogenous ATL in proliferative diseases. The actions of LX, ATL and stable analogs are transduced by a high affinity transmembrane receptor (ALXR) identified in several cell types (for a review, see Chiang et al. (25)). In mesangial cells, LXA$_4$ interacts with its own high affinity receptor (i.e., ALXR) as well as with a subclass of peptido-leukotriene receptors (cysLT$_1$), where LXA$_4$ is a partial agonist (24). In this regard, LXA$_4$ and its bioactive stable analogs effectively displace [$^3$H]LTD$_4$ specific binding to vascular endothelial cells (26). Also, recent findings provide the first evidence that ATL specifically antagonizes LTD$_4$ specific binding at recombinant human cysLT$_1$ cloned from endothelial cells, as well as acts at specific LXA$_4$ receptors (21). Since ATL-1 proved to be a potent inhibitor of HUVEC proliferation (FIGS. 1, 2 and 3), it was determined whether ATL affected angiogenesis in vivo.

Figure 4A:
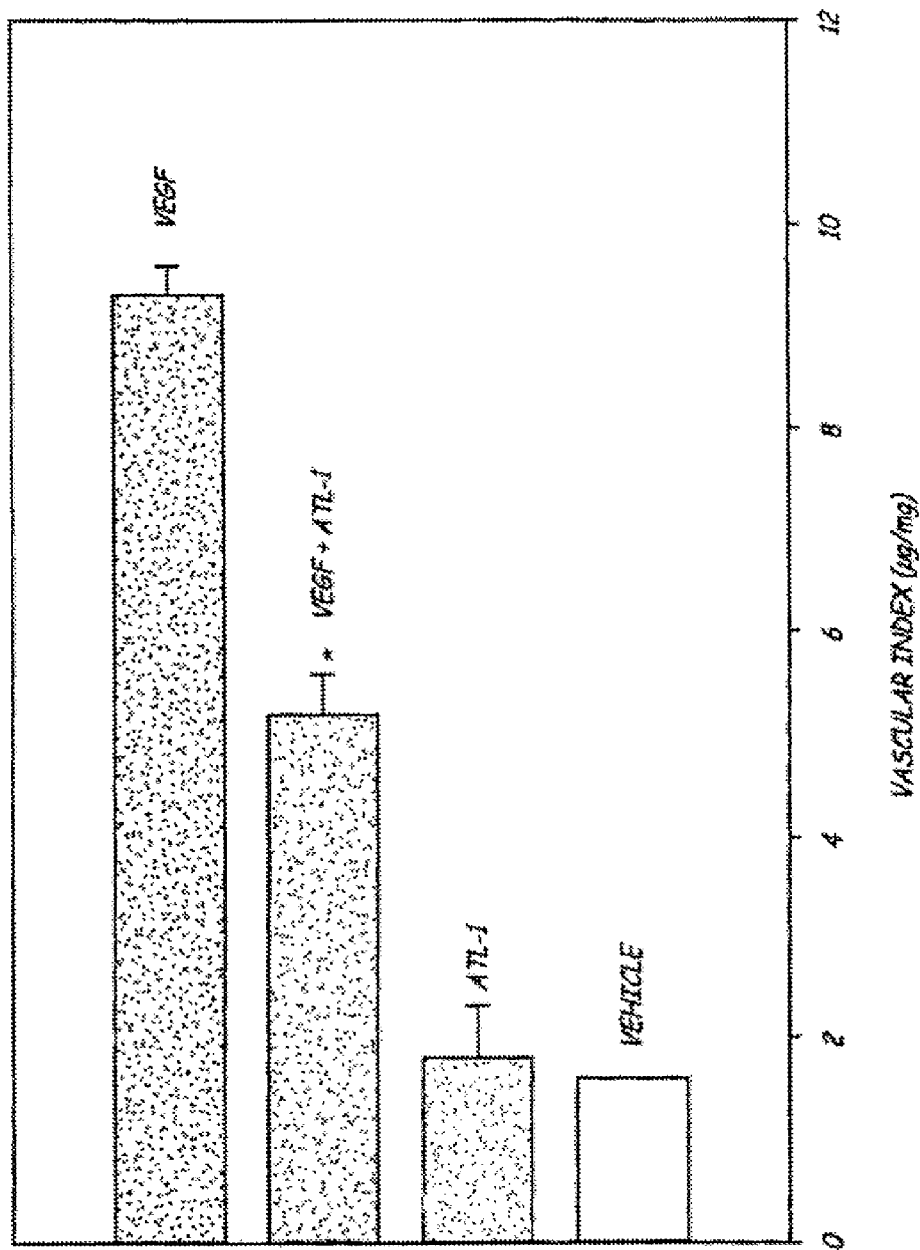
FIGS. 4A-B, demonstrate that ATL-1 inhibits angiogenic phenotype in vivo. 4A, Vascular index (VI=mg carmine dye/mg weight of tissue) in day-6 murine air pouch. Animals received a local injection of ATL-1 (10 µg/pouch) or vehicle immediately before VEGF (1 µg/pouch), 24 h after raising the pouch. Results are expressed as the mean±SE for n=4 animals per group. *Denotes statistically significant difference ($P<0.05$) from VEGF alone.

During chronic inflammation, new vessels are required not only for the maintenance of tissue perfusion, but also to allow increased cellular traffic (27). Therefore, to this end angiogenesis was assessed in vivo using a well established murine chronic granulomatous air pouch model, and the 6-day time interval was selected because it was shown to give near maximal vascular density (16). ATL-1 injected locally (10 µg/pouch) immediately before the administration of VEGF (1 µg/pouch) gave a ~48% reduction in the vascular index (FIG. 4A). For comparison, ATL-1 (10 µg/mouse or 0.4 mg/kg mouse) proved to be much more potent than other described anti-angiogenic agents that required much higher doses, including steroids at 1-3 mg/kg (16), or the COX-2 inhibitors, which require 1-6 mg/kg (28).

Figure 4B:
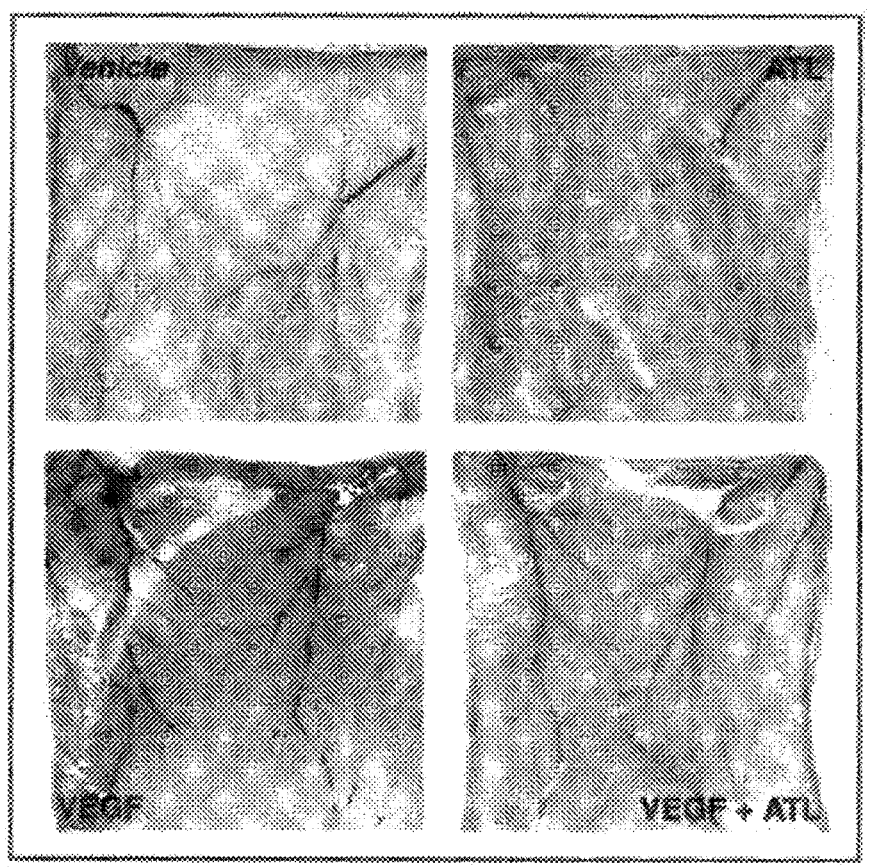

FIG. 4B shows representative vascular casts from typical day 6 air pouch linings. In the mice given VEGF (FIG. 4B, bottom left panel), there is an established neovasculature with an extremely high degree of vascular density compared to only slightly dilated capillaries in the ATL-treated animals, where there was routinely clearly reduced vascular density (FIG. 4B, bottom right panel). In another set of experiments, fluorescein isothiocyanate-dextran was used to visualize the vessels in this region. In sharp contrast to the actions of ATL-1, when LTB$_4$, another lipoxygenase pathway product, was given alone at the same dose as ATL-1 (10 µg LTB$_4$/pouch), LTB$_4$ stimulated neovascularization (n=2).

Figure 5:
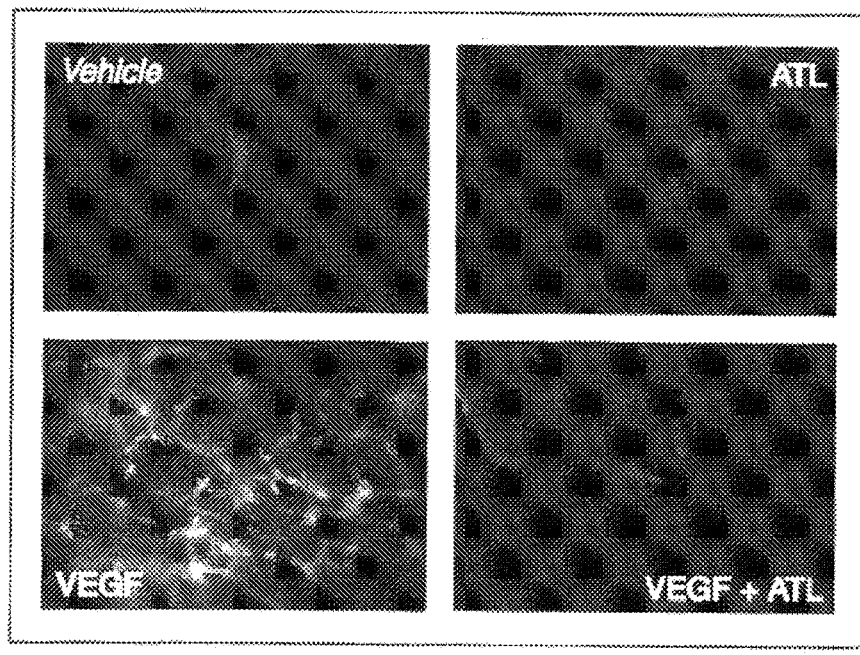
FIG. 5 depicts Anti-angiogenic action of ATL-1: fluorescent microscopy. Representative fluorescence photomicrographs showing the anti-angiogenic action of ATL-1 (10 µg/pouch) in the murine air pouch (see methods).

FIG. 5 shows photomicrographs of the dorsal linings dissected at day 6. Again, profound angiogenesis was demonstrated with extensive vascular networks in VEGF-treated pouch (FIG. 5, bottom left panel). Here too, treatment with ATL-1 (10 µg/pouch) gave striking reduction of VEGF-elicited vasculature, as exemplified by the lack of visible fine capillaries (FIG. 5, bottom right panel).

Figure 6:
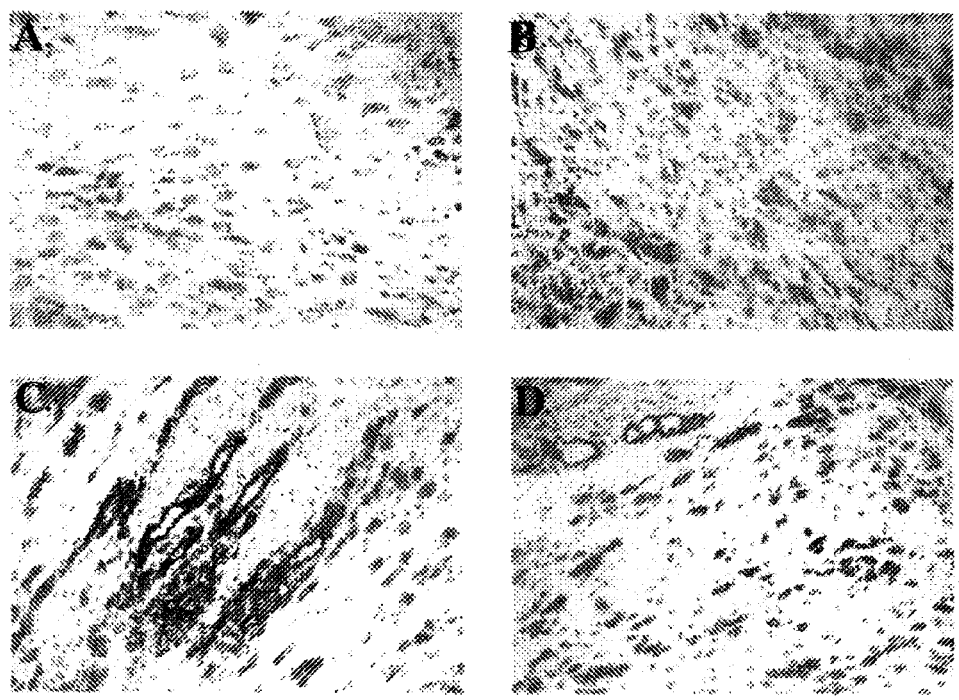
FIGS. 6A-D, are photomicrographs of a murine air pouch. Immunohistochemistry for murine air pouch CD31. Paraffin-embedded air pouch sections were stained for CD31 from mice as in FIGS. 4 and 5 and treated with vehicle alone (A), analog alone (B), VEGF-treated mice (C), and VEGF plus ATL-treated mice (D). Results are representative of eight separate mice each in duplicate. Magnification is 200× power and horseradish peroxidase with hematoxylin counterstain.

It is important to note that ATL-1 at this dose (10 µg/mouse i.v.) does not evoke apparent changes in mean arterial pressure, excluding a possible action of ATL-1 at the level of vascular tone. This is particularly noteworthy because, at high doses, LXA$_4$ can stimulate vasodilation in certain vascular beds. The present in vivo experiments were performed in separate series to evaluate histology and the presence of a vascular marker by using immunohistochemical staining of the murine air pouch with the vascular endothelial cell marker CD31 (FIG. 6).

Platelet/endothelial cell adhesion molecule-1 (or CD31) is a member of the Ig superfamily that is strongly expressed at the endothelial cell-cell junction, is present on platelets as well as leukocytes, and is held to play a role in angiogenesis and in transendothelial migration of leukocytes. Immunohistochemical staining for CD31 in the pouches showed that, in the VEGF-treated mice, strong specific endothelial cell staining was present and identified a prominent vascular network (FIG. 6C). In contrast, a marked diminution of vessels was observed in VEGF-treated mice that were also treated with the LXA$_4$ analog (FIG. 6D). The levels of mild nonspecific staining associated with these air pouches were essentially identical to those of the air pouch sections from mice treated with either vehicle alone (FIG. 6A) or with LX analog alone (FIG. 6B), namely, mild nonspecific staining of inflammatory cells, predominantly leukocytes and macrophages, that are known to be associated with these air pouches created from murine skin. Taken together, these findings indicate that ATL reduced VEGF-stimulated angiogenesis in vivo, suggesting that LXA$_4$ and 15-epi-LXA$_4$ can regulate these actions in vivo.

Results from many clinical and laboratory studies have demonstrated protective effects of aspirin in several forms of human cancer, including lung, colon and breast cancer, yet its potential anti-cancer mechanism is not clear (see Ref. 9). ASA is thought to act, in part, via reduction of angiogenesis, which might be related to the ability of ASA to inhibit prostanoid biosynthesis (7). More recently, ASA was found to trigger a novel switch in eicosanoid biosynthesis as the acetylation of COX-2 enables the enzyme to produce 15R-HETE that is converted to 15-epi-lipoxins, also known as ATL, during cell-cell interactions in vitro and in vivo (11, 12, 14). ATLs as well as their stable bioactive analogs are potent inhibitors of several key events in acute inflammation, such as PMN chemotaxis and transmigration across both endothelial and epithelial cells, as well as diapedesis from postcapillary venules (13, 14). The analogs of ATL mimic both endogenous ATL and LX actions and were designed to resist rapid enzymatic inactivation in vivo. Bioactive analogs of 15-epi-LXA$_4$ were also found to complete at both the ALXR on leukocytes and the cysLT$_1$ receptor present on vascular endothelial cells. In addition, these novel aspirin-triggered mediators inhibit cytokine release and can act at the gene transcriptional level (29) to redirect local cytokine-chemokine axis (30), actions that are both of interest in the angiogenic process (3). It should be noted that most if not all other eicosanoids examined to date are pro-angiogenic including leukotrienes (e.g., LTD$_4$ and LTB$_4$, see the following table and FIG. 3) (5, 6, 28). In view of this, it was surprising that ATL-1, LXA$_4$, 15-epi-LXA$_4$ and 15-R/S-methyl, LXA$_4$ possessed antiangiogenic activity.

| LXB$_4$-induced HUVEC Proliferation | |
|---|---|
| Compound | Percent of Proliferation |
| 14-epi-LXB$_4$ 0.1 nM | 15.5 ± 1.0 |
| 14-epi-LXB$_4$ 1.0 nM | 18.3 ± 1.6 |
| 14-epi-LXB$_4$ 10 nM | 27.0 ± 5.0 |
| 14-epi-LXB$_4$ 100 nM | 27.7 ± 1.3 |
| 15-epi-LXB$_4$ 0.1 nM | 20.1 ± 1.2 |
| 15-epi-LXB$_4$ 1.0 nM | 26.1 ± 2.8 |
| 15-epi-LXB$_4$ 10 nM | 34.0 ± 2.5 |
| 15-epi-LXB$_4$ 100 nM | 35.2 ± 5.2 |
| 15-epi-LXB$_4$-acetylenic 0.1 nM | 18.7 ± 1.6 |
| 15-epi-LXB$_4$-acetylenic 1.0 nM | 23.7 ± 0.4 |
| 15-epi-LXB$_4$-acetylenic 10 nM | 36.4 ± 3.7 |
| 15-epi-LXB$_4$-acetylenic 100 nM | 37.4 ± 5.3 |

VEGF-induced proliferation: 50.4 ± 4.0

Results

LipoxinA4 Receptor Expression in the Cornea

The expression of the receptor for ATLa in corneal tissue by RT-PCR was determined. In the normal corneas, Fpr-rs2 (one of the murine LXA$_4$ receptors), but not Fpr11 (another murine LXA$_4$ receptor), were present in both the epithelial and stromal-endothelial layers (FIG. 1).

Figure 7A:
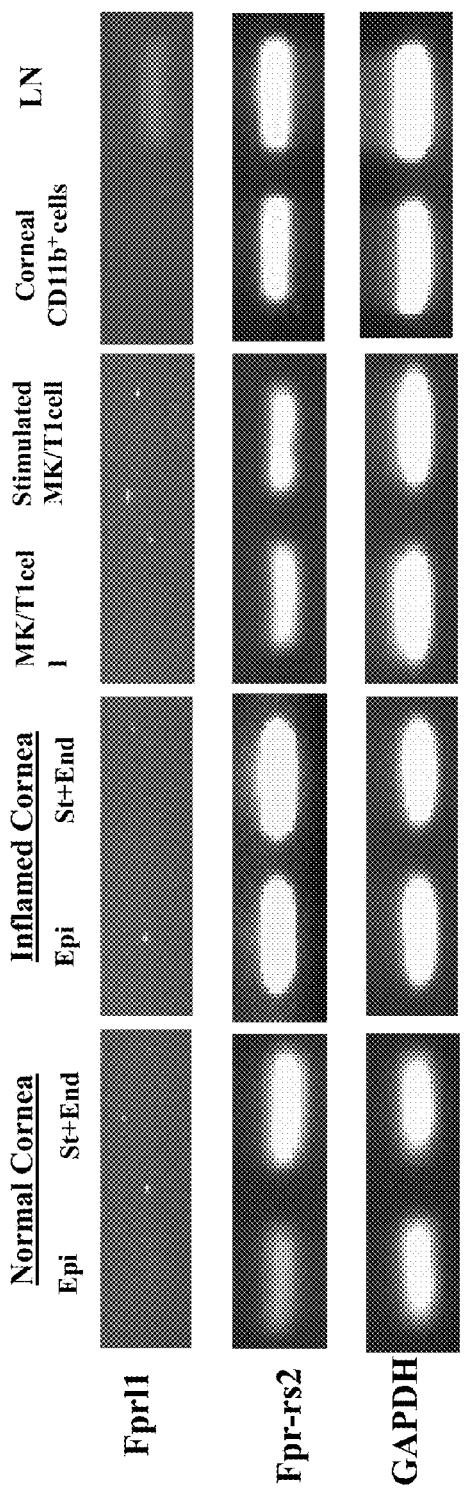
FIGS. 7A-B, Expression of receptor: Fpr-rs2 in Inflamed Corneas. 7A, RT-PCR was used to analyze expression of Fpr11 and Fpr-rs2 (ALX, $LXA_4$ receptors. Corneas of normal or inflamed eyes (10 corneas pooled per group) were collected and the epithelium was subsequently separated from the subjacent stroma-endothelium in the respective groups. RNA was isolated from these tissues, as well as from MK/T-1 cells (corneal keratocyte cell line) with or without TNF-α and IL-1β stimulation, or FACS-sorted CD11b+ cells from inflamed corneas. In addition, RNA was isolated from lymph nodes as a positive control. This experiment was repeated 3 times. 7B. The mean density of each band was measured by using NIH image J software. The densities of Fpr-rs2 band were normalized with the density of the corresponding GAPDH band. Data is shown as a mean of 3 experiments, and error bars represent SEM.
Figure 7B:
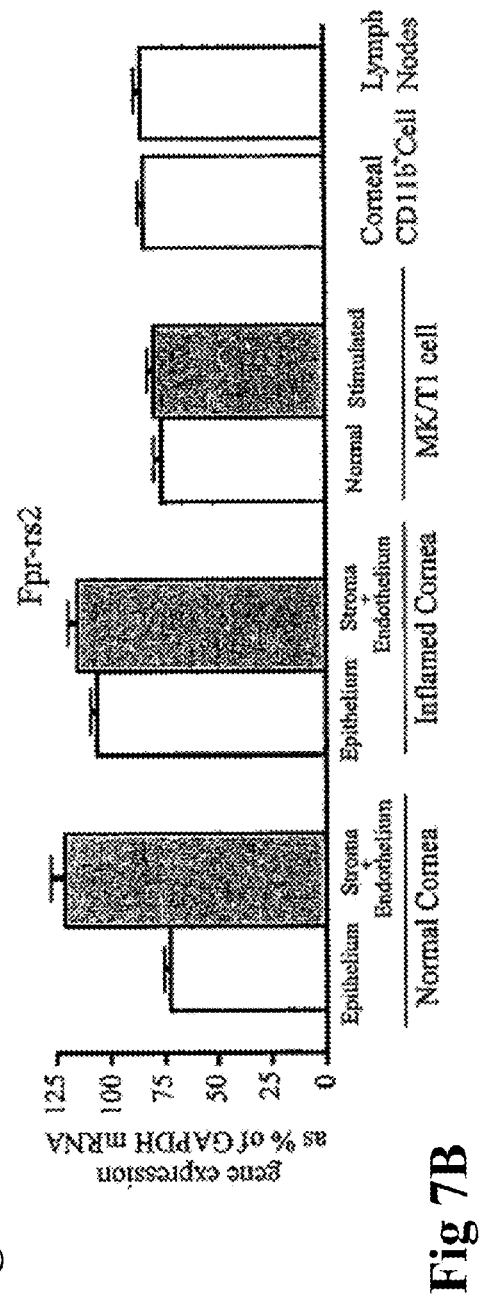

To further delineate whether corneal keratocytes versus immunocytic CD11b$^+$ cells (i.e., macrophages and dendritic cells) in the corneal stroma express these receptors, MK/T-1 cells (an immortalized corneal keratocyte cell line) were cultured and stimulated with TNF-α and IL-1β to mimic in situ corneal inflammation. RT-PCR results showed Fpr-rs2 was expressed by MK/T-1 cells irrespective of cytokine stimulation. In addition, the infiltrated CD11b$^+$ cells, sorted from the inflamed corneas, also expressed high levels of Fpr-rs2 (FIGS. 7A and B).

Application with ATLa Reduces Neutrophil and Macrophage Infiltration

Figure 8:
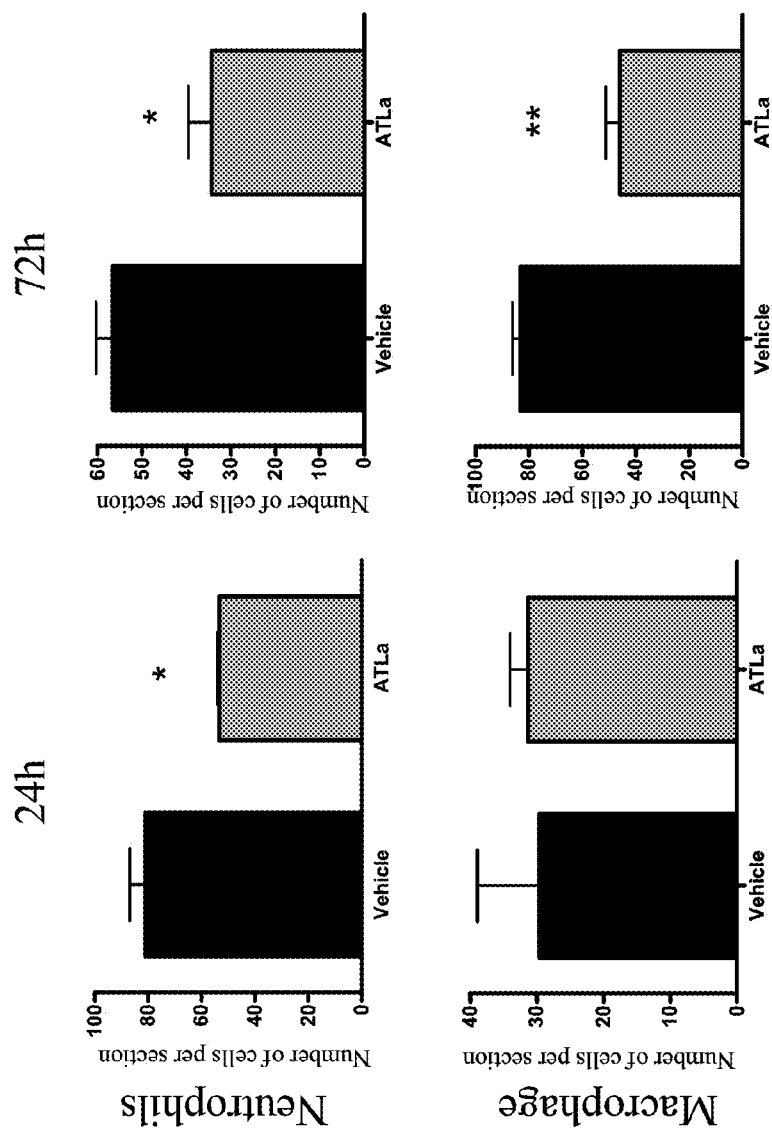
FIG. 8, Lipoxin Reduces Neutrophil and Macrophage Infiltration in Inflamed Corneas. ATLa or vehicle was subconjunctivally injected at 0 h and 48 h after suture placement. For each compound treatment, eyes were enucleated from a group of mice at 24 h, and another group at 72 h after suture placement (3 eyes per group). Cross-sections were stained with anti-neutrophil (NIMP-R14) or anti-macrophage (F4/80) Ab, and 12 sections were used to enumerate the respective leukocyte populations. Results represent the mean (±SEM) of 3 eyes per group (*$P<0.05$, ** $P<0.001$ vs vehicle-treated group, t-test), and data are representative of two independent experiments.

Next, inflamed corneas were treated with ATLa to assess the action of the lipid mediator on the infiltration of neutrophils and macrophages (FIG. 8). An approximate 30% inhibition of neutrophils recruitment (p<0.05) into the inflamed corneas was observed at 24 and 72 h with the administration of ATLa (neutrophils; 24 h: 53±1 cells/section, 72 h: 34±5 cells/section, n=3), compared to the vehicle-treated group (neutrophils; 24 h: 81±6 cells/section, 72 h: 57±4 cells/section, n=3). Similarly, macrophage infiltration was also reduced, but this was only observed at 72 h after suture placement: ATLa (macrophage; 46±5 cells/section, n=3) resulted in a 25-40% (p<0.05) reduction in macrophage infiltration compared to the vehicle control group (macrophage; 83±3 cells/section, n=3).

Application with ATLa Reduces Inflammatory Cytokine Expression

Figure 9:
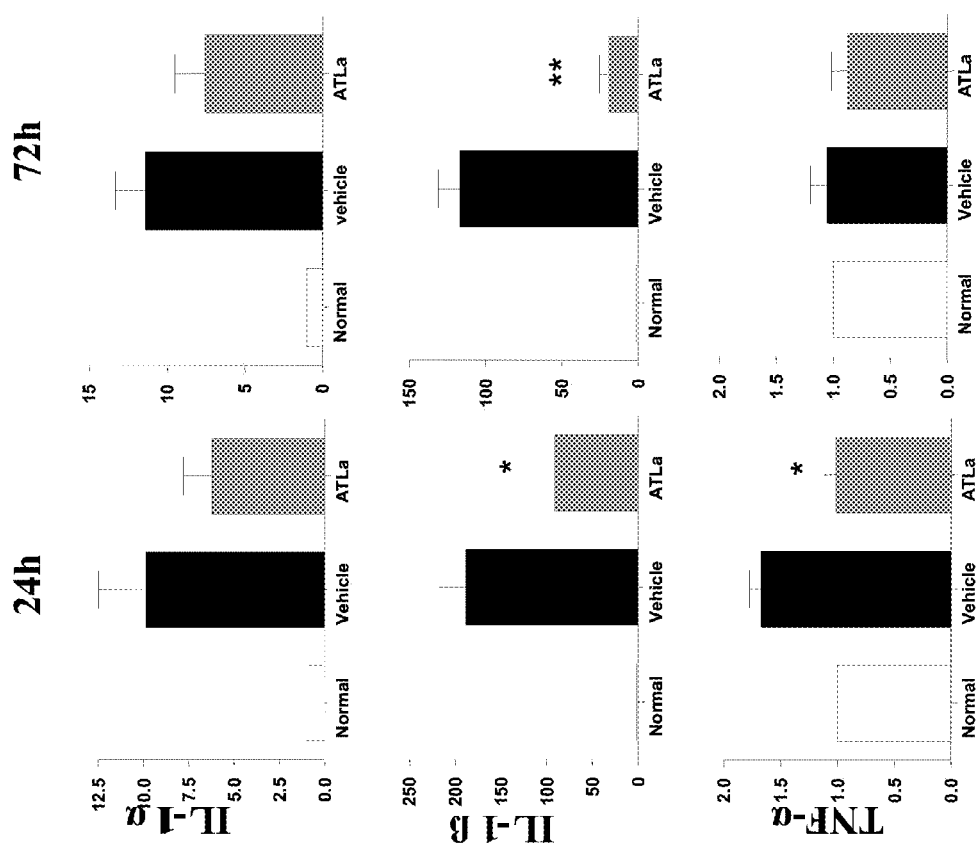
FIG. 9, Lipoxin Reduces Cytokine mRNA Expressions in Inflamed Corneas. ATLa or vehicle was subconjunctivally injected at 0 h and 48 h after suture placement. For each compound treatment, corneas were harvested from a group of mice at 24 h, and another group at 72 h after suture placement, as well as from normal untreated control corneas (6 corneas per group). mRNA levels of inflammatory cytokines (including IL-1α, IL-1β, and TNF-α) were determined by real-time PCR. Data were normalized to GAPDH mRNA and values were expressed as the fold change over normal control corneas. Results represent the mean (±SEM) of three samples per group (each sample consisted of 2 pooled corneas), and data are representative of two independent experiments (* $P<0.05$, ** $P<0.001$ vs vehicle-treated group, t-test).
Figure 13:
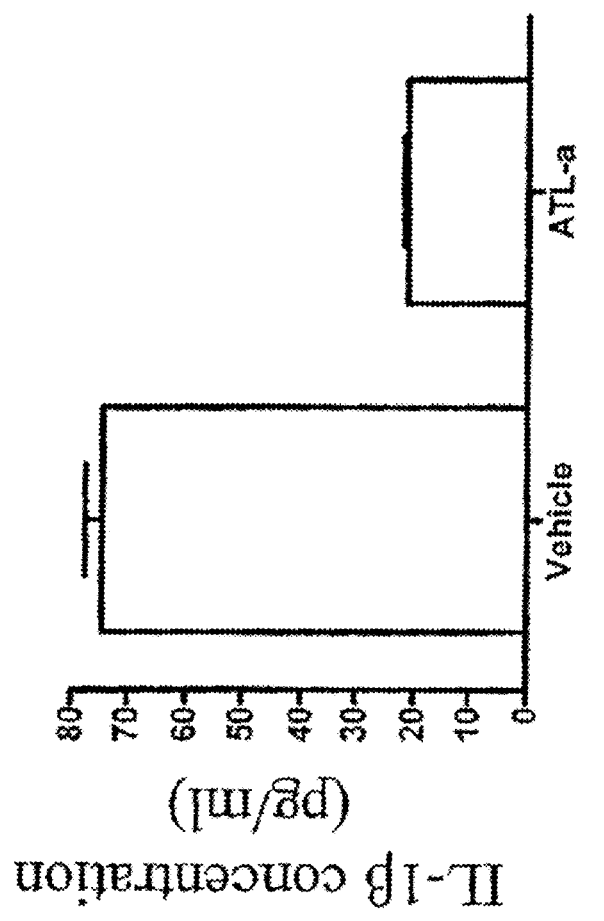
FIG. 13, ATLa Regulates IL-1β. Mice were treated at 0 h and 48 h after suture-placement with ATLa or vehicle. Whole corneas were excised at 72 h, and subsequently freeze-thawed 3 times. Cornea was then homogenized using a pellet pestile motor with additional protease inhibitors. Homogenates were centrifuged at 12,000 rpm for 5 minutes and the supernatant was assayed for mouse IL-1 beta via ELISA (eBioscience, USA) according to the manufacturer's instructions. In this experiment, it was that found 74.5±3.1 pg/ml of IL-1 beta in corneas from the vehicle-treated group (n=4), while a significantly lower amount of 21.3±0.8 pg/ml ($p<0.0001$) was found in corneas from the ATLa treated group (n=4).

The mRNA levels of inflammatory cytokines, IL-1α, IL-1β, and TNF-α, were monitored by real-time PCR at 24 h and 72 h after suture placement (FIG. 9). Treatment with ATLa led to a more than 50% reduction in the increase of IL-1β expression levels compared to the vehicle-treated controls (p<0.05) after induction of corneal inflammation. Increases in TNF-α expression were also significantly suppressed by the mediator at 24 h, but not at 72 h. The expression of IL-1α was not significantly altered by the lipid mediator (FIG. 9). It was also confirmed protein levels of inflammatory cytokine IL-1β using ELISA in the different treatment groups. Similar to RNA levels, ATLa-treated group shows 70% decrease in IL-1β protein level compared to vehicle-treated group (P<0.001, FIG. 13).

ATLa Impacts the Expression of VEGFs and VEGFRs

Figure 10A:
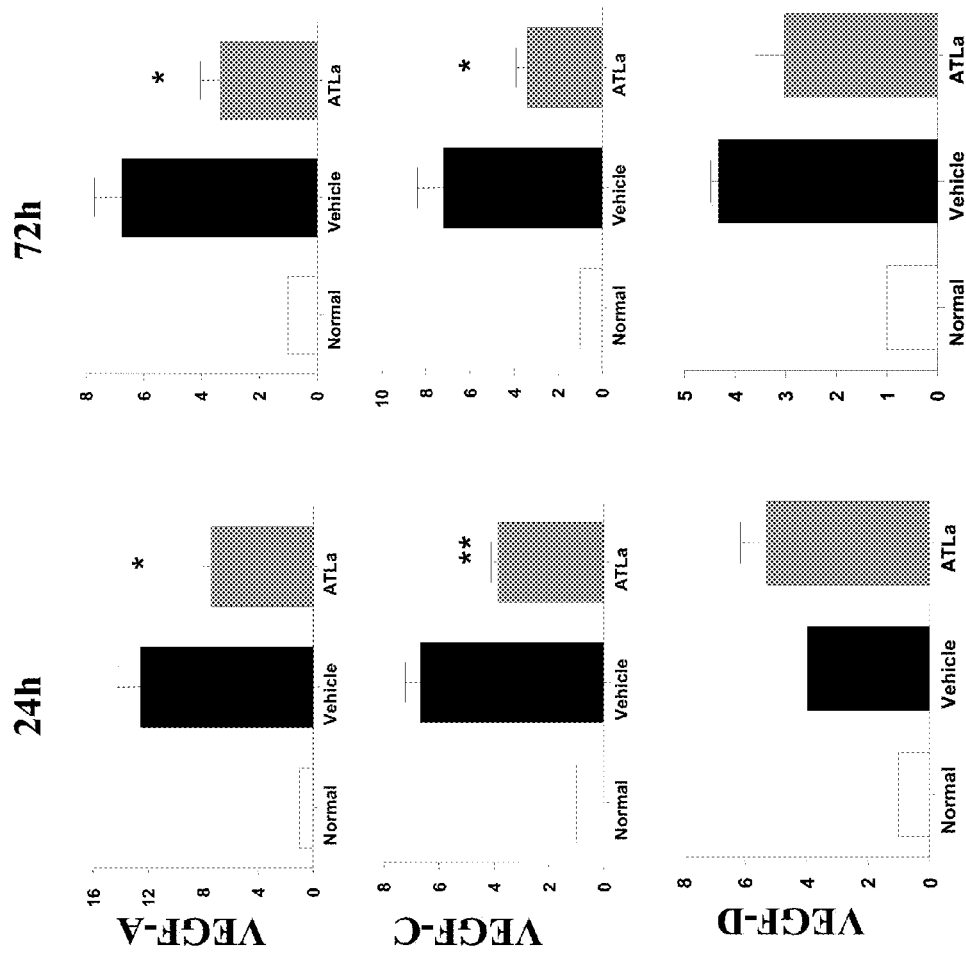
FIGS. 10A-B, The Impact of Lipoxin on the mRNA Expression of VEGFs and VEGFRs in Inflamed Corneas. ATLa or vehicle was subconjunctivally injected at 0 h and 48 h after suture placement. For each compound treatment, corneas were harvested from a group of mice at 24 h, and another group at 72 h after suture placement, as well as from normal untreated control corneas (6 corneas per group).
Figure 10B:
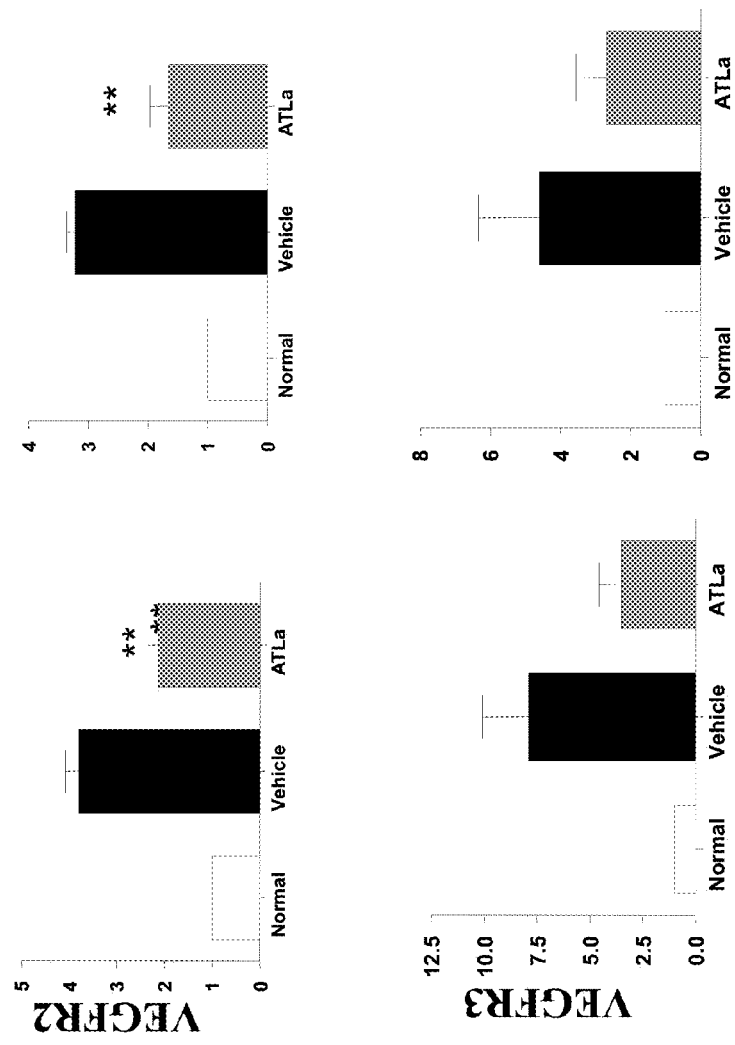

To determine the effect of ATLa in modulation of angiogenesis, mRNA expression was measured for the critical ligands (VEGF-A, C, D) and receptors (VEGFR-2, 3) involved in angiogenesis (FIGS. 10A and B). In contrast to the vehicle-treated group, the ATLa application group had lower mRNA expressions of the angiogenic growth factors, VEGF-A, C and their receptor, VEGFR-2, at 24 h and 72 h after suture placement. However, the mRNA expression for the lymphangiogeneic growth factor, VEGF-D and its receptor, VEGFR-3, were not significantly altered in the ATLa group relative to the vehicle-treated controls.

Evaluation of Clinical Corneal NV and Histological Assessment of HA and LA

Figure 11A:
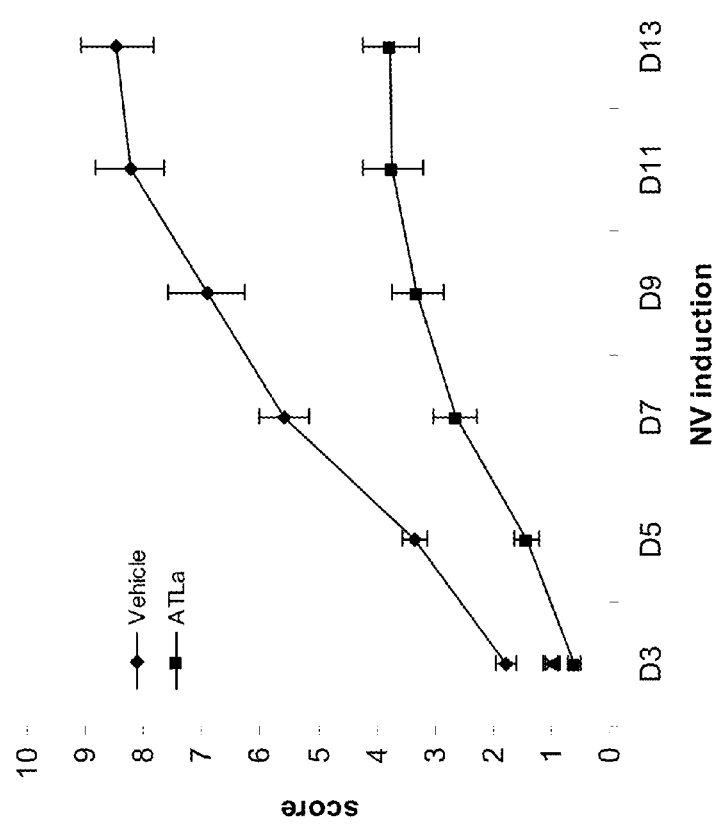
FIGS. 11A-C, Suture-induced Corneal HA is Reduced with Lipoxin. ATLa or vehicle was subconjunctivally injected every 48 h from 0 to 14 days after suture placement.
Figure 11B:
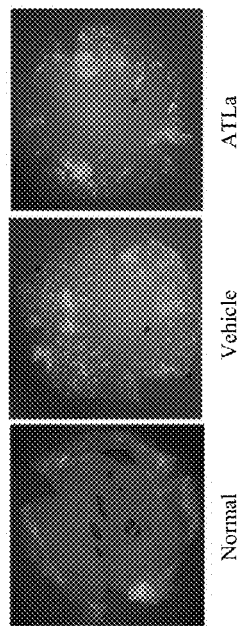
Figure 11C:
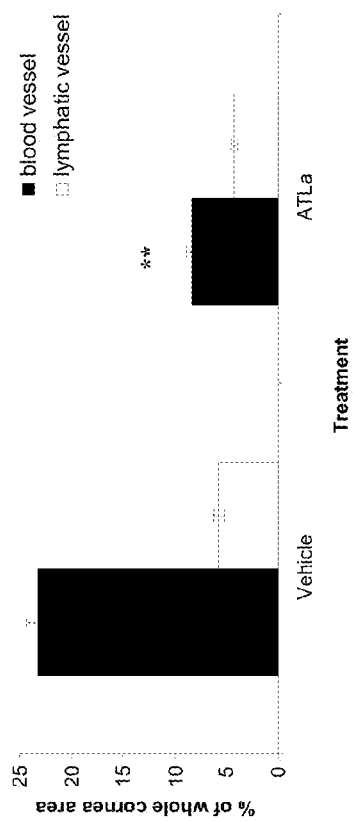

The growth of corneal neovessels was measured over a 2-week time course via slit lamp biomicroscopy. Use of corneal sutures in this model induces inflammatory NV within 2 days and peaks approximately 2 weeks post manipulation as described previously.[43] It was observed that application with the lipid mediator led to significant suppression of the angiogenic response, relative to the vehicle control (FIGS. 11A-C). It was further compared the density of the blood vessels (BV) and lymphatic vessels (LV) using whole-mounted corneas harvested from the different groups, and co-stained these with anti-CD31 and anti-LYVE-1 (BV are CD31$^{high}$/LYVE-1$^-$, while the LV are CD31$^{low}$LYVE-1$^{high}$). Consistent with slit-lamp observations, by day 14 after suture placement the BV density was significantly suppressed with ATLa (8.26±0.63%, n=6) application, relative to vehicle application (23.18±1.12%, n=6). Interestingly, significant changes in the density of lymphatic vessels among the lipid mediator groups relative to the vehicle controls were not observed.

ATLa Regulation of IL-β and VEGF-A Induced-HA

Figures 12A, 12B:
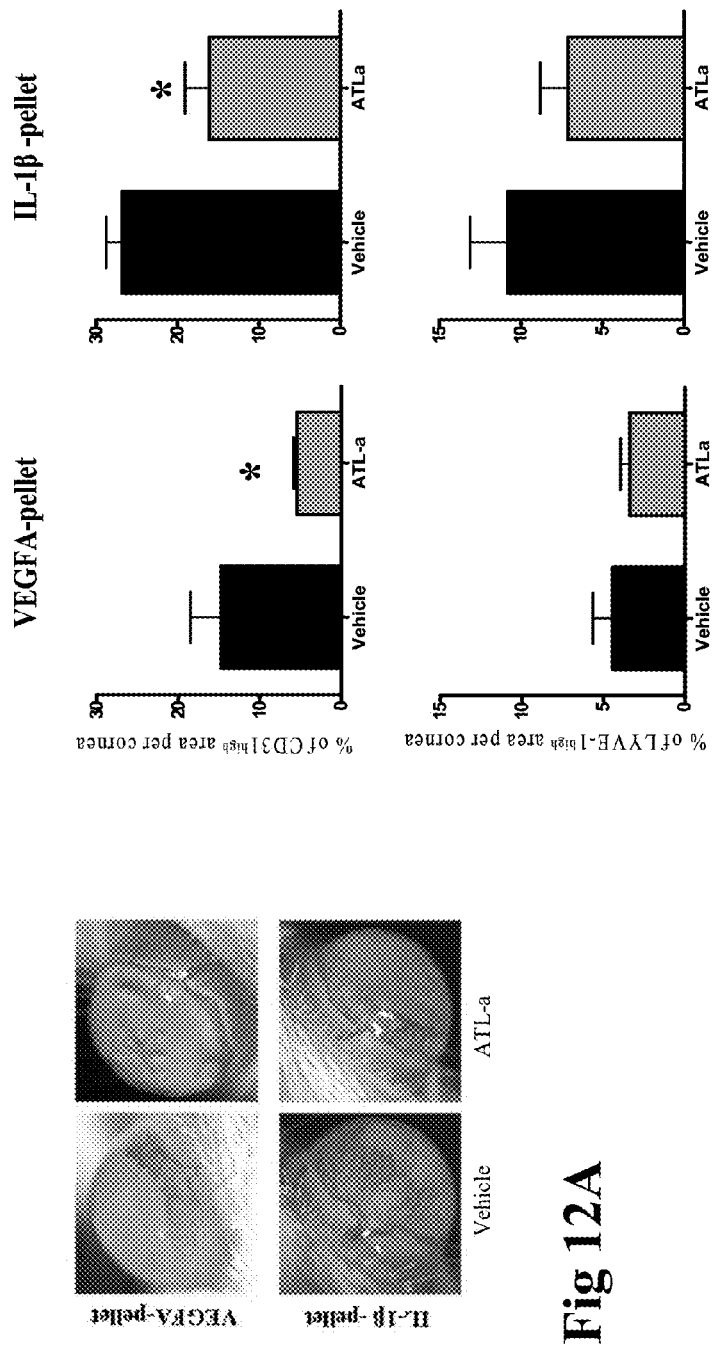
FIGS. 12A-B, ATLa Regulate IL-1β- and VEGF-A-induced Corneal HA and LA. Hydron pellets containing IL-1β or VEGF-A were implanted into the corneas on day 0. ATLa or vehicle was subconjunctivally injected every 48 h from 0 to 7 days after pellet implantation (4 corneas per treatment, for each pellet-type). 12A. Slit-lamp examination was performed on day 7 and representative images are shown. 12B. The density of blood vessels ($CD31^{high}$/LYVE-1$^-$) or lymphatic vessels ($CD31^{low}$LYVE-1$^{high}$) covering each cornea was analyzed. Values are expressed as the mean (±SEM) of each treatment group (4 corneas per group) and the data are representative of two independent experiments (* $P<0.05$ vs vehicle-treated group, t-test).

To further dissect the direct regulatory actions of these lipid mediators on VEGF-A-induced angiogenesis versus a more 'indirect' inhibitory effect on angiogenesis via suppression of innate immune responses, HA and LA were measured after intrastromal placement of micropellets loaded with IL-1β- or VEGF-A. Quantitative analysis of corneal flat-mounts harvested from VEGF-A micropellet stimulation showed that the BV density in the group treated with ATLa (5.9±0.4%, n=4) was significantly lower relative to vehicle treatment (14.75±3.8%, n=4). Vessel growth stimulated by IL-1β-micropellets was more marked than that with VEGF-A stimulation. Nonetheless, treatment with ATLa (BV density; 16.1±3.0%, n=4) significantly impaired IL-1β-induced BV growth, relative to vehicle treatment (BV density; 26.8±2.0%, n=4). Interestingly, and corroborating with previous observations in suture-induced corneal NV, no significant reduction of LA stimulated by either IL-1β- or VEGF-A was observed with any of these mediator treatments (FIGS. 12A-B).

Discussion

The present invention provides that the lipid mediator, ATLa regulates VEGF-A/-C and VEGFR2 and as a result, significantly reduces the development of NV in the inflamed cornea, in addition to their resolving effects on innate immunity. The present invention also provides that corneal tissues and infiltrating innate immune cells express Fpr-rs2 (the LXA$_4$ receptor); the ligation of which directly suppress angiogenesis. In the aggregate, these results in a model of surgically induced corneal inflammation and angiogenesis confirm the functions of ATLa as potent dual anti-inflammatory and pro-resolution molecules that can also effectively stop angiogenesis.

The neutrophil is the most prominent and earliest cell to migrate into the cornea in the early stages of inflammation, and anti-inflammatory lipid mediators can promote resolution by shortening the duration of neutrophil tissue infiltration.(54) In line with this current understanding, the present invention provides that the administration of ATLa indeed blocked neutrophil infiltration of the cornea at 24 h and 72 h post insult-a time point which coincided with the down-regulation of proinflammatory cytokine (e.g., TNF-α, IL-1-α, and IL-1-β expression known to be secreted by innate immunocytes, in particular neutrophils. Moreover, the data also show that macrophage infiltration is also reduced significantly after local administration of ATLa. These results highlight the importance of neutrophil infiltration in the local chemotaxis of subsequent immunocyte populations such as the macrophage. It has been shown that ATLa can also increase macrophage phagocytosis (e.g. of apoptotic neutrophils) and this may also contribute to the resolution of inflammation following treatments.(55) Taken together, local administration of these lipid mediators to the cornea control local innate immune cell infiltration and enhance the resolution of inflammation.

While the healthy or normal cornea is avascular, local inflammation can stimulate the ingrowth of neovessels from the surrounding limbal and conjunctival areas through secretion of pro-angiogenesis factors by local vascular endothelial and inflammatory cells. Cytokines such as IL-1β, IL-1α, and TNF-α, are known to enhance the expression of angiogenic factors.(56-58) Among all the angiogenic factors, the VEGF species play a pivotal role in vascular development. Ligation of VEGFR2 by VEGF-A is critical in vascular EC proliferation and differentiation in hemangiogenesis. On the other hand, binding of VEGF-C/-D to VEGFR3 stimulates the development of lymphatic vessels. In addition, VEGF-C can also bind and activate VEGFR2,(30,31) and thereby contribute to HA, despite having a weaker binding affinity than VEGF-A.(32) Interestingly, the present invention provides that treatments with ATLa significantly reduced the gene expression levels of VEGF-A, VEGF-C and their receptor VEGFR2, but not VEGF-D or VEGFR3. This indicates that such treatments selectively regulate HA, rather than LA, and this was further supported by immunohistochemistry.

While IL-1 secretion can stimulate VEGF expression and thereby promote angiogenesis, administration of exogenous VEGF-A can achieve a similar effect (possibly independent of other downstream effectors resulting from IL-1 signaling). The present invention determined whether the suppression of corneal NV by ATLa is due to suppression of IL-1β and/or VEGF-A stimulation.

Interestingly, however, the present invention indicated that ATLa treatment not only reduced IL-1β induced corneal angiogenesis, but also that induced by VEGF-stimulation. The exclusive ability to suppress VEGF-A-induced angiogenesis by ATLa treatment, could be in part, result from impairment in the early stage of EC migration.(64) It is also noteworthy that relative to the other treatments, ATLa is thought to be active for a longer duration as it is a stable analog of $LXA_4$/ATL which resists local inactivation.(65) Moreover, ATLa exerts its inhibitory effects on multiple steps of the VEGF-A-induced angiogenesis, such as inhibition of EC adhesion, (67,68) and suppression of VEGF-A-induced EC proliferation. (69) These factors explain the actions of ATLa and its demonstrable higher potency in suppressing angiogenesis.

$LXA_4$'s anti-inflammation and pro-resolution functions are related to the receptor ALX/FPRL1, which has been identified on neutrophils, monocytes, macrophages, dendritic cells, epithelial cells and keratocyte in humans. This function is subserved by multiple receptors in the murine system, including Lxa4r/Fprl1 and Fpr-rs2 which share 89% and 83% homology at the nucleotide and protein levels, respectively. (66) The present invention provides that Fpr-rs2 but not Lxa4r/Fprl1, are expressed by the infiltrating $CD11b^+$ cells (which include macrophages, and monocytic dendritic cells, and a subset of neutrophils) in the cornea. These results suggest that ATLa activation of Fpr-rs2 on these $CD11b^+$ immunocytes stops their local migration and cytokine production into cornea.

Finally, it is noteworthy that while the expression of ALX in the cornea has been implicated in epithelial cell proliferation in a wound healing model, (70,71) the location of ALX in the cornea had not been established to date. Here, for the first time, the present invention distinguished the distribution of Fpr-rs2 in the cornea, which include epithelial cells and stromal keratocytes in both normal and inflammatory conditions. In conclusion, ATLa effectively resolves corneal inflammation and angiogenesis by controlling innate inflammation via marked reduction of proinflammatory cytokine secretion and inhibiting VEGF/VEGFR expression. These novel lipid mediators offer a potentially new therapeutic strategy in controlling corneal angiogenesis, a leading cause of visual blindness worldwide.

Methods

Animals

Six to eight-week-old male BALB/c (Taconic Farms, Germantown, N.Y.) mice were used in all experiments. All experimental protocols were approved by the Schepens Eye Research Institute Animal Care and Use Committee, and all animals were treated according to the Association for Research in Vision and Ophthalmology Statement for the Use of Animals in Ophthalmic and Vision Research.

Suture-Induced Inflammatory Corneal Angiogenesis

The standard model for induction of inflammatory corneal NV is associated with development of intrastromal vessels in close association with a mixed-cell (primarily neutrophilic) infiltrate. (43,44) Three interrupted sutures (11-0 nylon, Sharpoint; Vanguard, Houston, Tex.) were placed intrastromally with two stromal incursions extending over 120° of the corneal circumference each to induce inflammatory corneal NV, which is also associated with significant LA, as described previously. (43) The corneas were followed by slit-lamp biomicroscopy for corneal NV development. NV was graded between 0 and 3, with increments of 0.5, using a grid system per each corneal quadrant based on the centripetal extent of the neovascular branches from the limbus. Scores for each quadrant then summed to derive the NV index (range 0 to 12) for each eye, as previously described. (43)

Corneal Micropocket Assay

The corneal micropocket assay in mice and quantification of the resultant NV has been described previously. (45,46) In brief, 0.3 µl of hydron pellets (IFN Sciences, New Brunswick, N.J.) containing 30 ng of murine IL-1β (R&D Systems, Minneapolis, Minn.) or 200 ng of VEGF-A (gift from BRB Preclinical Repository, National Cancer Institute) were prepared and implanted into the corneal stroma of male BALB/c mice. After 7 days the animals were sacrificed and the corneas were harvested for quantitative analysis of HA and LA.

Ocular Administration of Compounds

BALB/c mice were randomized to receive ATLa, or vehicle (normal saline) by subconjunctival injection in a masked fashion after suture or hydron pellet placement. The compounds were administered at a dose of 100 ng/10 µl per mouse every 48 h after suture or pellet placed. ATLa was synthesized as described previously. (49) The physical properties were monitored routinely via LC/MS/MS matching the reported biological and physical properties prior to analysis in present experiments.

RNA Isolation and Reverse Transcriptase (RT)-PCR

Corneas were carefully dissected to ensure that the conjunctival and iris tissues were not included. To extract mRNA from whole-thickness corneas, two corneas were pooled as a sample in each group. To extract mRNA from corneal epithelial and stroma-endothelial layers separately, intact corneas were placed in 30 µl of RNA stabilization reagent (RNAlater, Qiagen, Valencia, Calif.) at 4° C. overnight and then stored at −30° C. for 2-3 days. After incubated in 250 µl 20 mM EDTA (sterile, pH 7.4) at 37° C. for 30 minutes, the epithelial layers were peeled off the stroma-endothelial layers before mRNA isolation. Ten corneal epithelial layers or stroma-endothelial layers were pooled as a sample in each group. The mRNA isolated from submandibular lymph nodes were used as positive controls.

A combined-method for total RNA isolation was employed, using Trizol (Invitrogen Corp., Carlsbad, Calif.) and RNeasy MinElute Spin Columns (Qiagen, Valencia, Calif.), as described previously. (50) Reverse transcription of total RNA was conducted using oligo(dT)$_{20}$ primer and Superscript™ III Reverse Transcriptase (Invitrogen, Carlsbad, Calif.). PCR was conducted using primer pairs for Fprl1 (sense GATGCTAGAGGGGATGTGCAC, antisense TCTTCAGGAAGTGAAGCC, 530 bp), Fpr-rs2 (sense tgctgtcaagatcaacagaag, antisense tgccaggaggtgaagtagaac, 359 bp) and GAPDH (sense GAAGGGCATCTTGGGCTACAC, antisense GCAGCGAACTTTATTGATGGTATT, 373 bp). The PCR conditions were 35 cycles at 95° C. for 30 seconds, 56° C. for 30 seconds, and 72° C. for 1 minute, followed by finial extension at 72° C. for 10 minutes. PCR products were observed by agarose gel electrophoresis. The mean density of each band was measured by using NIH image J software. The density of each receptor band was divided by the density of the corresponding GAPDH band to obtain the normalized band density.

Real-Time PCR

1 µl of total cDNA, synthesized from 400 ng total RNA with random hexamers using Superscript™ III Reverse Transcriptase (Invitrogen, Carlsbad, Calif.), was loaded in each well and assays were performed in triplicates. Quantitative PCR was performed with Taqman Universal PCR Mastermix and FAM-MGB dye labeled predesigned primers (Applied Biosystems, Foster City, Calif.) for IL-1α (Mm99999060_m1), TNF-α(Mm99999068_m1), IL-1β (Mm00434228_m1), VEGFR2 (Mm00440099_m1), VEGFR3 (Mm00433337_m1), VEGFA (Mm00437304_m1), VEGFC (Mm00437313_m1). PCR conditions were 2 minutes at 50° C., 10 minutes at 95° C., followed by 35 cycles of 15 second at 95° C. and 60° C. for 1 minute using an ABI PRISM 7900 HT (Applied Biosystems, CA). PCR amplification of the house-keeping gene encoding GAPDH (Mm999999915_g1) was performed during each run for each sample to allow normalization between samples. A nontemplate control was included in all the experiments to evaluate DNA contamination of isolated RNA and reagents. The results were analyzed by comparative threshold cycle ($C_T$) method. The relative expression level of each sample was expressed as fold change from normal control.

Isolation of Cornea-infiltrating Cells

Forty corneas were pooled, teased with scissors, and digested with collagenase D (Roche Applied Science, 11088874103) at 37° C. for 1 h in a humidified atmosphere of 5% $CO_2$. After incubation, corneas were disrupted by grinding with a syringe plunger. (51-52) Total cells were then collected after passing through a steel mesh. Upon blockade by anti-FcRmAb, these cells were labeled with FITC-conjugated rat anti-mouse CD11b (granulocyte/monocyte/macrophage marker, BD Pharmingen, San Diego, Calif.) at 4° C. for 30 minutes. CD11b$^+$ cells were sorted from total cells by using MoFlo® High-Performance Cell Sorter (Cytomation, Fort Collins, Colo.).

MK/T-1 Cell Culture and Stimulation

MK/T-1 cells, immortalized keratocytes from the corneal stroma of C57BL/6 mouse (gift from R. L. Gendron [Memorial University of Newfoundland, St. John's, Newfoundland, Canada]), were used to identify the expression of lipid mediator receptors on the corneal keratocytes. MK/T-1 cells were grown in low-glucose Dulbecco's minimum essential medium supplemented with 10% fetal bovine serum and 1 mM α-glutamine at 37° C. in 5% $CO_2$. To stimulate MK/T-1 cells, 10 ng/µl TNF-α (R&D Systems, Minneapolis, Minn.) and 10 ng/µl IL-1β were added in the culture medium.

Immunohistochemical Studies

Full thickness corneal tissue or 8 µm-frozen sections were fixed in acetone for 15 minutes at room temperature. To block non-specific staining, anti-FcR mAb (CD16/CD31, FcγIII/II receptor) or 10% goat serum was used before primary antibodies or isotype-matched control antibodies were applied at 4° C. overnight. Thereafter, samples were incubated with secondary antibodies at RT. Each step was followed by three thorough washings in PBS for 5-10 minutes. Finally, the samples were covered with mounting medium (Vector Laboratories, Burlingame, Calif.) and analyzed by epifluorescence microscopy (Eclipse E800; Nikon, Tokyo, Japan). The following antibodies were used: FITC-conjugated rat anti-mouse CD31 (Santa Cruz Biotechnology, Santa Cruz, Calif.), purified rat anti-mouse neutrophil (NIMP-R14, Abcam, Cambridge, Mass.), purified rat anti-mouse F4/80 (Novus Biologicals, Littleton, Colo.) and purified rabbit anti-mouse LYVE-1 (Abcam, Cambridge, Mass.). The secondary antibodies were Rodamine-conjugated donkey anti-rabbit IgG and Rodamine-conjugated goat anti-rat IgG (Santa Cruz Biotechnology, Santa Cruz, Calif.). Isotype controls included FITC-conjugated rat IgG2a, purified rat IgG2b, and purified rabbit IgG (Santa Cruz Biotechnology, Santa Cruz, Calif.).

To quantify corneal angiogenesis, digital pictures of corneal flat-mounts were taken using an image analysis system (Spot Image Analysis, Diagnostic Instruments, Sterling Heights, Mich.). The areas covered by $CD31^{high}/LYVE-1^-$-vessels (blood vessels) or $CD31^{low}LYVE-1^{high}$ vessels (lymphatics) were measured morphometrically using NIH Image J software (version 1.34s; http://rsb.info.nih.gov/ij). The total corneal area was outlined using the inner-most vessel of the limbal arcade as the border. The vessel density was calculated by the proportion of neovascularized area to the whole corneal area.

Statistics

All data are expressed as means±SEM. Statistical significance between the vehicle and each lipid mediator group was analyzed by the two-tailed t-test with Prism (version 4.0; GraphPad, San Diego, Calif.).

The present invention is drawn to methods for treating disease states or conditions that are associated with inflammation. The recruitment of neutrophils, leukocytes and/or cytokines are included within the general scope of NV, hemangiogenesis and/or angiogenic condition(s) of corneal tissue that can be treated by unexpectedly lipoxins.

Given the cellular origins of the different chambers of the eye, it is not possible to assume that the same targets are present in the front or cornea of the eye versus the retina or any other part of the eye; each need to be established separately both in experimental laboratory settings in animals and with the rigor of clinical trials in human studies.

The eye, being a highly specialized sensory organ, has cells in the anterior chamber that differ in their origin from cells in the posterior chamber. Therefore, therapeutic approaches and current treatments of the cornea vs. retinal layer and sclera retinal-glial scleral layer are not and cannot be assumed to be the same.

Because of the anatomical structural and functional differences in each section of the eye, therapeutics need to be targeted to precise locations within the eye, for example, cornea vs. retina, in order to achieve appropriate therapeutic interventions. The cell types and their pathologies in these sections of the human eye are different.

A point of fact that the cornea versus the retina are physiologically of a different ilk has given rise to very different study groups at the national level as currently considered by the NIH. For example, the anterior portion of the eye and associated structures, e.g. the cornea, canal of Schlemm, lens, etc. are addressed by a specific study section at the level of the NIH, whereas structures of the posterior chamber and section of the eye including retina, optic nerve, etc. are addressed by a separate study section. This is because the tissue and cell types from the posterior of the eye are largely of neural origin or highly specialized non-photosensitive epithelial layers, such as in the retina, whereas cells in the cornea are nonvascular, non-refractive epithelial cells. It is these cell type differences and anatomical differences that give rise to different treatment distinctions.

Agents that act on cells of the human retina (anti-VEGF therapies, etc.) do not have specific targeted actions within the healthy human cornea per se and current therapies along these lines need to be injected within the vitreous body posterior chamber of the eye. These treatments include, for example, anti-VEGF therapies.

The present surprisingly demonstrates the unique suture model of angiogenesis in the cornea and lipoxins are able to protect from neovascularization of corneal tissues. Without this experimental evidence put forth in the specification, this could not be anticipated or was predictable.

More importantly, limited therapeutics are available to topically treat inflammation in the cornea that are also able to regulate unwanted neovascularization of the corneal tissue. Current anti-inflammatories for topical treatments in the eye, i.e., applied directly to the cornea, include steroids, which are well appreciated by the clinical community to have long-term deleterious side effects.

The current findings that lipoxins are anti-inflammatory topically as well as prevent neovascularization in a cornea suture model is an ideal example of novel dual-pronged actions of the lipoxins in cornea. In the cornea, neovascularization is un wanted as it can limit vision.

Corneal replacements are routinely carried out and can be associated in humans with suture-induced/initiated local inflammation. Topical application of lipoxins as demonstrated for the first time in direct comparison from the present results could be useful in the treatment of this currently unmet clinical need.

In summary, the present results demonstrate that an aspirin-triggered-lipoxin, 15-epi-LXA$_4$ analog, is a potent inhibitor of angiogenesis and of endothelial cell proliferation in vivo. Together these results reveal a novel action of 15-epi-lipoxins and suggest a role for the aspirin-triggered lipoxin circuit (14) as a potential mechanism that can contribute to aspirin's recognized anti-angiogenic and anti-inflammatory properties (2, 7, 10). With increasing insight into the fundamental role of angiogenesis within a broad range of physiological as well as disease processes (1-3), the modulation of vascular growth could be a previously unappreciated and important strategic action for ATL, the natural endogenous lipoxin mimetic and their synthetic analogs.

REFERENCES

1. Folkman, J., and Y. Shing. 1992. Angiogenesis. *J. Biol. Chem.* 267:10931-10934.
2. Folkman, J. 1995. Angiogenesis in cancer, vascular, rheumatoid and other disease. *Nature Med.* 1:27-31.
3. Arenberg, D. A., and R. M. Strieter. 1999. Angiogenesis. In Inflammation: Basic Principles and Clinical Correlates. J. I. Gallin and R. Snyderman, editors. Lippincott Williams & Wilkins, Philadelphia. 851-864.
4. Höper, M. M., N. F. Voelkel, T. O. Bates, J. D. Allard, M. Horan, D. Shepherd, and R. M. Tuder. 1997. Prostaglandins induce vascular endothelial growth factor in a human monocytic cell line and rat lungs via cAMP. *Am. J. Respir. Cell Mol. Biol.* 17:748-756.
5. Nie, D., K. Tang, C. Diglio, and K. V. Honn. 2000. Eicosanoid regulation of angiogenesis: role of endothelial arachidonate 12-lipoxygenase. *Hemost. Thromb. Vasc. Biol.* 95:2304-2311.
6. Stoltz, R. A., N. G. Abraham, and M. L. Schwartzman. 1996. The role of NF-kB in the angiogenic response of coronary microvessel endothelial cells. *Proc. Natl. Acad. Sci. USA* 93:2832-2837.
7. Hla, T., A. Ristimäki, S. Appleby, and J. G. Barriocanal. 1993. Cyclooxygenase gene expression in inflammation and angiogenesis. *Ann. N.Y. Acad. Sci.* 696:197-204.
8. Jones, M. K., H. Wang, B. M. Peskar, E. Levin, R. M. Itani, I. J. Sarfeh, and A. S. Tarnawski. 1999. Inhibition of angiogenesis by nonsteroidal anti-inflammatory drugs: Insight into mechanisms and implications for cancer growth and ulcer healing. *Nature Med.* 5:1418-1423.
9. Marcus, A. J. 1995. Aspirin as prophylaxis against colorectal cancer. *N. Engl. J. Med.* 333, no. September 7:656-658.
10. Vane, J. 2000. Aspirin and other anti-inflammatory drugs. *Thorax* 55 (Suppl. 2):53.
11. Clària, J., and C. N. Serhan. 1995. Aspirin triggers previously undescribed bioactive eicosanoids by human endothelial cell-leukocyte interactions. *Proceedings of the National Academy of Sciences of the United States of America* 92, no. 21:9475-9479.
12. Chiang, N., T. Takano, C. B. Clish, N. A. Petasis, H.-H. Tai, and C. N. Serhan. 1998. Aspirin-triggered 15-epi-lipoxin A$_4$ (ATL) generation by human leukocytes and murine peritonitis exudates: Development of a specific 15-epi-LXA$_4$ ELISA. *J. Pharmacol. Exp. Ther.* 287:779-790.
13. Clish, C. B., J. A. O'Brien, K. Gronert, G. L. Stahl, N. A. Petasis, and C. N. Serhan. 1999. Local and systemic delivery of a stable aspirin-triggered lipoxin prevents neutrophil recruitment in vivo. *Proc. Natl. Acad. Sci. USA* 96:8247-8252.

14. Serhan, C. N. 1997. Lipoxins and novel aspirin-triggered 15-epi-lipoxins (ATL): a jungle of cell-cell interactions or a therapeutic opportunity? *Prostaglandins* 53:107-137.
15. Marshall, N. J., C. J. Goodwin, and S. J. Holt. 1995. A critical assessment of the use of microculture tetrazolium assays to measure cell growth and function. *Growth Regulation* 5:69-84.
16. Colville-Nash, P. R., C. A. S. Alam, I. Appleton, J. R. Brown, M. P. Seed, and D. A. Willoughby. 1995. The pharmacological modulation of angiogenesis in chronic granulomatous inflammation. *J. Pharmacol. Exp. Ther.* 274:1463-1472.
17. Gupta, K., S. Kshirsagar, W. Li, L. Gui, S. Ramakrishnan, P. Gupta, P. Y. Law, and R. P. Hebbel. 1999. VEGF prevents apoptosis of human microvascular endothelial cells via opposing effects on MAPK/ERK and SAPK/JNK signaling. *Exp. Cell Res.* 247:495-504.
18. Eliceiri, B. P., and D. A. Cheresh. 1999. The role of av integrins during angiogenesis: insights into potential mechanisms of action and clinical development. *J. Clin. Invest.* 103:1227-1230.
19. Kelavkar, U. P., and K. F. Badr. 1999. Effects of mutant p53 expression on human 15-lipoxygenase-promoter activity and murine 12/15-lipoxygenase gene expression: Evidence that 15-lipoxygenase is a mutator gene. *Proc. Natl. Acad. Sci. USA* 96:4378-4383.
20. Munger, K. A., A. Montero, M. Fukunaga, S. Uda, T. Yura, E. Imai, Y. Kaneda, J. M. Valdivielso, and K. F. Badr. 1999. Transfection of rat kidney with human 15-lipoxygenase suppresses inflammation and preserves function in experimental glomerulonephritis. *Proc. Natl. Acad. Sci. USA* 96:13375-13380.
21. Gronert, K., T. Martinsson-Niskanen, S. Ravasi, N. Chiang, and C. N. Serhan. 2001. Selectivity of recombinant human leukotriene $D_4$, leukotriene $B_4$, and lipoxin $A_4$ receptors with aspirin-triggered 15-epi-$LXA_4$ and regulation of vascular and inflammatory responses. *Am. J. Pathol.* 158:3-9.
22. Sodin-Semrl, S., B. Taddeo, D. Tseng, J. Varga, and S. Fiore. 2000. Lipoxin $A_4$ inhibits IL-1 beta-induced IL-6, IL-8, and matrix metalloproteinase-3 production in human synovial fibroblasts and enhances synthesis of tissue inhibitors of metalloproteinases. *J. Immunol.* 164:2660-2666.
23. Clària, J., M. H. Lee, and C. N. Serhan. 1996. Aspirin-triggered lipoxins (15-epi-LX) are generated by the human lung adenocarcinoma cell line (A549)-neutrophil interactions and are potent inhibitors of cell proliferation. *Molecular Medicine* 2:583-596.
24. McMahon, B., C. Stenson, F. McPhillips, A. Fanning, H. R. Brady, and C. Godson. 2000. Lipoxin $A_4$ antagonizes the mitogenic effects of leukotriene $D_4$ in human renal mesangial cells: Differential activation of MAP kinases through distinct receptors. *J. Biol. Chem.* 275:27566-27575.
25. Chiang, N., K. Gronert, F.-H. Qiu, and C. N. Serhan. 2000. Lipoxin $A_4$ receptor. In Cytokine Reference. J. J. Oppenheim, M. Feldmann, S. K. Durum, T. Hirano, J. Vilcek and N. A. Nicola, editors. Academic Press, London. 2219-2233.
26. Takano, T., S. Fiore, J. F. Maddox, H. R. Brady, N. A. Petasis, and C. N. Serhan. 1997. Aspirin-triggered 15-epi-lipoxin $A_4$ and $LXA_4$ stable analogs are potent inhibitors of acute inflammation: Evidence for anti-inflammatory receptors. *J. Exp. Med.* 185:1693-1704.
27. Cotran, R. S., V. Kumar, and T. Collins, editors. 1999. *Robbins Pathologic Basis of Disease.* 6th ed. W.B. Saunders Co., Philadelphia.
28. Masferrer, J. L., A. Koki, and K. Seibert. 1999. COX-2 inhibitors: a new class of antiangiogenic agents. *Ann. N.Y. Acad. Sci.* 889:84-86.
29. Gewirtz, A. T., B. McCormick, A. S, Neish, N. A. Petasis, K. Gronert, C. N. Serhan, and J. L. Madara. 1998. Pathogen-induced chemokine secretion from model intestinal epithelium is inhibited by lipoxin $A_4$ analogs. *J. Clin. Invest.* 101:1860-1869.
30. Hachicha, M., M. Pouliot, N. A. Petasis, and C. N. Serhan. 1999. Lipoxin $(LX)A_4$ and aspirin-triggered 15-epi-$LXA_4$ inhibit tumor necrosis factor 1a-initiated neutrophil responses and trafficking: regulators of a cytokine-chemokine axis. *J. Exp. Med.* 189:1923-1929.
31. Edelman J L, Castro M R, Wen Y. Correlation of VEGF expression by leukocytes with the growth and regression of blood vessels in the rat cornea. *Invest Ophthalmol Vis Sci.* 1999; 40:1112-1123.
32. Naldini A, Carraro F. Role of inflammatory mediators in angiogenesis. *Curr Drug Targets Inflamm Allergy.* 2005; 4:3-8.
33. Benelli R, Morini M, Carrozzino F, et al. Neutrophils as a key cellular target for angiostatin: implications for regulation of angiogenesis and inflammation. *FASEB J.* 2002; 16:267-269.
34. Sterescu A E, Rousseau-Harsany E, Farrell C, Powell J, David M, Dubois J. The potential efficacy of omega-3 fatty acids as anti-angiogenic agents in benign vascular tumors of infancy. *Med. Hypotheses.* 2006; 66:1121-1124.
35. Serhan C N, Chiang N, Van Dyke T E. Resolving inflammation: dual anti-inflammatory and pro-resolution lipid mediators. *Nat Rev Immunol.* 2008; 8:349-361.
36. Serhan C N, Clish C B, Brannon J, Colgan S P, Chiang N, Gronert K. Novel functional sets of lipid-derived mediators with antiinflammatory actions generated from omega-3 fatty acids via cyclooxygenase 2-nonsteroidal antiinflammatory drugs and transcellular processing. *J Exp Med.* 2003; 192:1197-1204.
37. Serhan C N, Hong S, Gronert K, et al. Resolvins: a family of bioactive products of omega-3 fatty acid transformation circuits initiated by aspirin treatment that counter proinflammation signals. *J Exp Med.* 2002; 196:1025-1037.
38. Brink C, Dahlén S E, Drazen J, et al. International Union of Pharmacology XXXVII. Nomenclature for leukotriene and lipoxin receptors. *Pharmacol Rev.* 2003; 55:195-222.
39. Bandeira-Melo C, Bozza P T, Diaz B L, et al. Cutting edge: Lipoxin (LX) A4 and aspirin-triggered 15-epi-$LXA_4$ block allergen-induced eosinophil trafficking. *J Immunol.* 2002; 164:2267-2271.
40. Levy B D, De Sanctis G T, Devchand P R, et al. Multi-pronged inhibition of airway hyper-responsiveness and inflammation by lipoxin A4. *Nat. Med.* 2002; 8:1018-1023.
41. Karp C L, Flick L M, Park K W, et al. Defective lipoxin-mediated anti-inflammatory activity in the cystic fibrosis airway. *Nat. Immunol.* 2004; 5:388-392.
42. Serhan C N, Jain A, Marleau S, et al. Reduced inflammation and tissue damage in transgenic rabbits overexpressing 15-lipoxygenase and endogenous anti-inflammatory lipid mediators. *J Immunol.* 2003; 71:6856-6865.
43. Dana M R, Zhu S N, Yamada J. Topical modulation of interleukin-1 activity in corneal neovascularization. *Cornea.* 1998; 17:403-409.
44. Dana M R, Streilein J W. Loss and restoration of immune privilege in eyes with corneal neovascularization. *Invest Ophthalmol V is Sc.i* 1996; 37:2485-2494.
45. Williams C S, Tsujii M, Reese J, Dey S K, DuBois R N. Host cyclooxygenase-2 modulates carcinoma growth. *J Clin Invest.* 2005; 105:1589-1594.

46. Fõld M, Zhu L X, Sharma S, et al. Cyclooxygenase-2-dependent expression of angiogenic CXC chemokines ENA-78/CXC ligand (CXCL) 5 and interleukin-8/CXCL8 in human non-small cell lung cancer. *Cancer Res.* 2004; 64:1853-1860.
47. Arita M, Bianchini F, Aliberti J, et al. Stereochemical assignment, antiinflammatory properties, and receptor for the omega-3 lipid mediator resolvin E1. *J Exp Med.* 2005; 201:713-722.
48. Sun Y P, Oh S F, Uddin J, et al. Resolvin D1 and its aspirin-triggered 17R epimer. Stereochemical assignments, anti-inflammatory properties, and enzymatic inactivation. *J Biol. Chem.* 2007; 282:9323-9334.
49. Serhan C N, Maddox J F, Petasis N A, et al. Design of lipoxin A4 stable analogs that block transmigration and adhesion of human neutrophils. *Biochemistry.* 1995; 34:14609-14615.
50. Jin Y, Shen L, Chong E M, et al. The chemokine receptor CCR7 mediates corneal antigen-presenting cell trafficking. *Mol. Vis.* 2007; 13:626-634.
51. Deshpande S, Zheng M, Lee S, et al. Bystander activation involving T lymphocytes in herpetic stromal keratitis. *J Immunol.* 2001; 167:2902-2910.
52. Biswas P S, Banerjee K, Zheng M, et al. Counteracting corneal immunoinflammatory lesion with interleukin-1 receptor antagonist protein. *J Leukoc Biol.* 2004; 76:868-875.
53. Sonoda K, Sakamoto T, Yoshikawa H, et al Inhibition of corneal inflammation by the topical use of Ras farnesyltransferase inhibitors: selective inhibition of macrophage localization. *Invest Ophthalmol V is Sci.* 1998; 39:2245-2251.
54. Serhan C N, Savill J. Resolution of inflammation: the beginning programs the end. *Nat. Immunol.* 2005; 12:1191-1197.
55. Schwab J M, Chiang N, Arita M, Serhan C N. Resolvin E1 and protectin D1 activate inflammation-resolution programmes. *Nature.* 2007; 447:869-874.
56. Torisu H, Ono M, Kiryu H, et al. Macrophage infiltration correlates with tumor stage and angiogenesis in human malignant melanoma: possible involvement of TNFalpha and IL-1alpha. *Int J Cancer.* 2000; 85:182-188.
57. Ryuto M, Ono M, Izumi H, et al. Induction of vascular endothelial growth factor by tumor necrosis factor alpha in human glioma cells. Possible roles of SP-1. *J Biol. Chem.* 1996; 271:28220-28228.
58. Yoshida S, Ono M, Shono T, et al. Involvement of interleukin-8, vascular endothelial growth factor, and basic fibroblast growth factor in tumor necrosis factor alpha-dependent angiogenesis. *Mol Cell Biol.* 1997; 17:4015-4023.
59. Joukov V, Pajusola K, Kaipainen A, et al. A novel vascular endothelial growth factor, VEGF-C, is a ligand for the Flt4 (VEGFR-3) and KDR (VEGFR-2) receptor tyrosine kinases. *EMBO J.* 1996; 15:290-298.
60. Baldwin M E, Roufail S, Halford M M, Alitalo K, Stacker S A, Achen M G. Multiple forms of mouse vascular endothelial growth factor-D are generated by RNA splicing and proteolysis. *J Biol. Chem.* 2001; 276:44307-44414.
61. Fierro I M. Angiogenesis and lipoxins. *Prostaglandins Leukot Essent Fatty Acids.* 2005; 73:271-275.
62. Connor K M, SanGiovanni J P, Lofqvist C, et al. Increased dietary intake of omega-3-polyunsaturated fatty acids reduces pathological retinal angiogenesis. *Nat. Med.* 2007; 13:868-873.
63. Nakao S, Kuwano T, Tsutsumi-Miyahara C, et al. Infiltration of COX-2-expressing macrophages is a prerequisite for IL-1 beta-induced neovascularization and tumor growth. *J Clin Invest.* 2005; 115:2979-2991.
64. Fierro I M, Kutok J L, Serhan C N. Novel lipid mediator regulators of endothelial cell proliferation and migration: aspirin-triggered-15R-lipoxin A(4) and lipoxin A(4). *J Pharmacol Exp Ther.* 2002; 300:385-392.
64. Clish C B, O'Brien J A, Gronert K, Stahl G L, Petasis N A, Serhan C N. Local and systemic delivery of a stable aspirin-triggered lipoxin prevents neutrophil recruitment in vivo. *Proc Natl Acad. Sci.* 1999; 96:8247-8252.
66. Chiang N, Serhan C N, Dahlen S E, et al. The lipoxin receptor ALX: potent ligand-specific and stereoselective actions in vivo. *Pharmacol Rev.* 2006; 58:463-487.
67. Cezar-de-Mello P F, Nascimento-Silva V, Villela C G, Fierro I M. Aspirin-triggered Lipoxin A4 inhibition of VEGF-induced endothelial cell migration involves actin polymerization and focal adhesion assembly. *Oncogene.* 2006; 25:122-129.
68. Cezar-de-Mello P F, Vieira A M, Nascimento-Silva V, Villela C G, Barja-Fidalgo C, Fierro I M. ATL-1, an analogue of aspirin-triggered lipoxin A(4), is a potent inhibitor of several steps in angiogenesis induced by vascular endothelial growth factor. *Br J Pharmacol.* 2008; 153:956-965.
69. Wittamer V, Franssen J D, Vulcano M, et al. Specific recruitment of antigen-presenting cells by chemerin, a novel processed ligand from human inflammatory fluids. *J Exp Med.* 2003; 198:977-985.
70. Gronert K, Gewirtz A, Madara J L, Serhan C N. Identification of a human enterocyte lipoxin A4 receptor that is regulated by interleukin (IL)-13 and interferon gamma and inhibits tumor necrosis factor alpha-induced IL-8 release. *J Exp Med.* 1998; 187:1285-1294.
71. Gronert K, Maheshwari N, Khan N, Hassan I R, Dunn M, Laniado Schwartzman M. A role for the mouse 12/15-lipoxygenase pathway in promoting epithelial wound healing and host defense. *J Biol. Chem.* 2005; 280:15267-15278.

Those skilled in the art will know, or be able to ascertain, using no more than routine experimentation, many equivalents to the specific embodiments of the invention described herein. These and all other equivalents are intended to be encompassed by the following claims. All publications and references cited herein, including those in the background section, are expressly incorporated herein by reference in their entirety.

What is claimed is:

1. A method to treat corneal neovascularization comprising administering a composition comprising a lipoxin compound to the corneal tissue of a subject in need thereof, wherein the lipoxin compound comprises the formula

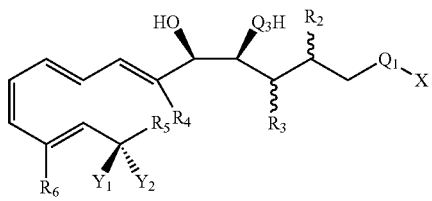

wherein X is R1, OR.1, or SR1;
wherein R1 is
(i) a hydrogen atom;
(ii) an alkyl of 1 to 8 carbons atoms, inclusive, which can be straight chain or branched;
(iii) a cycloalkyl of 3 to 10 carbon atoms, inclusive;

(iv) an aralkyl of 7 to 12 carbon atoms;
(v) phenyl;
(vi) substituted phenyl

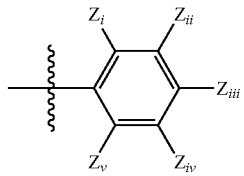

wherein Zi, Zii, Ziii, Ziv and Zv are each independently selected from —NO2, —CN, —C(=O)—R1, —SO3H, a hydrogen atom, halogen, methyl, —ORx, wherein Rx is 1 to 8 carbon atoms, inclusive, which can be a straight chain or branched, and hydroxyl;
or
(vii) a straight or branched chain alkenyl of 2 to 8 carbon atoms, inclusive;
wherein Q1 is (C=O), SO2 or (CN);
wherein Q3 is O, S or NH;
wherein one of R2 and R3 is a hydrogen atom and the other is
(a) a hydrogen atom;
(b) an alkyl of 1 to 8 carbon atoms, inclusive, which can be straight chain or branched;
(c) a cycloalkyl of 3 to 6 carbon atoms, inclusive;
(d) an alkenyl of 2 to 8 carbon atoms, inclusive, which can be straight chain or branched; or
(e) Ra Q2Rb
wherein Q2 is —O— or —S—;
wherein Ra is alkylene of 0 to 6 carbons atoms, inclusive, which can be straight chain or branched; and wherein Rb is alkyl of 0 to 8 carbon atoms, inclusive, which can be straight chain or branched;
wherein R4 is
(a) a hydrogen atom;
(b) an alkyl of 1 to 6 carbon atoms, inclusive, which can be straight chain or branched;
wherein Y1 or Y2 is —OH, methyl, or —SH and wherein the other is
(a) a hydrogen atom
(b) CHaZb
where a+b=3, a=0 to 3, b=0 to 3; and
each Z, independently, is a cyano, a nitro, or a halogen atom;
(c) an alkyl of 2 to 4 carbon atoms, inclusive, straight chain or branched; or
(d) an alkoxy of 1 to 4 carbon atoms, inclusive;
or Y1 and Y2 taken together are
(a) =NH; or
(b) =O;
wherein R5 is
(a) an alkyl of 1 to 9 carbon atoms which can be straight chain or branched;

(b) —(CH2)n-Ri
wherein n=0 to 4 and Ri is
(i) a cycloalkyl of 3 to 10 carbon atoms, inclusive;
(ii) a phenyl; or
(iii) substituted phenyl

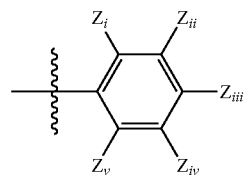

wherein Zi, Zii, Ziii, Ziv and Zv are each independently selected from —NO2, —CN, —C(=O)—R1, —SO3H, a hydrogen atom, halogen, methyl, —ORx, wherein Rx is 1 to 8 carbon atoms, inclusive, which can be a straight chain or branched, and hydroxyl;
(c) RaQaRb
wherein Qa is O or S;
wherein Ra is alkylene of 0 to 6 carbons atoms, inclusive, which can be straight chain or branched;
wherein Rb is alkyl of 0 to 8 carbon atoms, inclusive, which can be straight chain or branched;
(d) —C(Riii)(Riv)-Ri
wherein Riii and Riv are each, independently:
(i) a hydrogen atom;
(ii) CHaZb where a+b=3, a=0 to 3, b=0+3, and wherein each Z, independently, is a cyano, a nitro, or a halogen atom;
(e) a haloalkyl of 1 to 8 carbon atoms, inclusive, and 1 to 6 halogen atoms, inclusive, straight chain or branched; and
wherein R6 is
(a) a hydrogen atom;
(b) an alkyl from 1 to 4 carbon atoms, inclusive, straight chain or branched;
(c) a halogen.

2. The method of claim 1, wherein the lipoxin compound comprises the formula

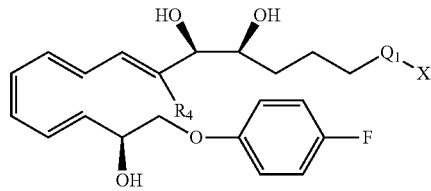

wherein $Q_1$ is a carbonyl;
X is a hydroxyl, an —OR, or a pharmaceutically acceptable salt of a carboxylic acid;
R, if present, is an alkyl group; and
$R_4$ is a hydrogen atom.

* * * * *